(12) United States Patent
Kuwajima et al.

(10) Patent No.: US 11,594,761 B2
(45) Date of Patent: Feb. 28, 2023

(54) ELECTROLYTIC SOLUTION, ELECTROCHEMICAL DEVICE, LITHIUM-ION SECONDARY CELL, AND MODULE

(71) Applicant: DAIKIN INDUSTRIES, LTD., Osaka (JP)

(72) Inventors: Yoshiko Kuwajima, Osaka (JP); Kotaro Hayashi, Osaka (JP); Hisako Nakamura, Osaka (JP); Takaya Yamada, Osaka (JP); Yuuki Suzuki, Osaka (JP); Shigeaki Yamazaki, Osaka (JP); Akiyoshi Yamauchi, Osaka (JP); Kenzou Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 244 days.

(21) Appl. No.: 16/762,574

(22) PCT Filed: Oct. 26, 2018

(86) PCT No.: PCT/JP2018/039910
§ 371 (c)(1),
(2) Date: May 8, 2020

(87) PCT Pub. No.: WO2019/093161
PCT Pub. Date: May 16, 2019

(65) Prior Publication Data
US 2020/0365945 A1    Nov. 19, 2020

(30) Foreign Application Priority Data

Nov. 9, 2017    (JP) .............................. JP2017-216708

(51) Int. Cl.
| H01M 10/0569 | (2010.01) |
| H01M 10/0525 | (2010.01) |
| C07C 69/36 | (2006.01) |
| H01G 11/58 | (2013.01) |

(52) U.S. Cl.
CPC ......... *H01M 10/0569* (2013.01); *C07C 69/36* (2013.01); *H01G 11/58* (2013.01); *H01M 10/0525* (2013.01); *H01M 2300/004* (2013.01)

(58) Field of Classification Search
None
See application file for complete search history.

(56) References Cited

U.S. PATENT DOCUMENTS

| 2004/0258996 A1 | 12/2004 | Kim et al. | |
| 2015/0372349 A1* | 12/2015 | Shikita .................. | C07C 309/65 558/56 |
| 2016/0285131 A1 | 9/2016 | Yamauchi et al. | |
| 2016/0329599 A1* | 11/2016 | Kim .................. | H01M 10/0567 |

FOREIGN PATENT DOCUMENTS

| JP | 2002-367674 A | 12/2002 |
| JP | 2007-066864 A | 3/2007 |
| JP | 2007-112737 A | 5/2007 |
| JP | 4050251 B2 | 2/2008 |
| JP | 2009-117383 A | 5/2009 |
| JP | 2010-262800 A | 11/2010 |
| JP | 2010262800 | * 11/2010 |
| JP | 2011-238373 A | 11/2011 |
| JP | PCT/JP2018/039907 | 10/2018 |
| KR | 10-2015-0072188 A | 6/2015 |
| WO | 2015/083747 A1 | 6/2015 |
| WO | PCT/JP2018/039903 | 10/2018 |
| WO | 2019/093159 A1 | 5/2019 |
| WO | 2019/093160 A1 | 5/2019 |

OTHER PUBLICATIONS

JP 2011238373 English translation. Ihara et al. Japan. Nov. 24, 2011. (Year: 2011).*

(Continued)

*Primary Examiner* — Christopher P Domone
(74) *Attorney, Agent, or Firm* — Sughrue Mion, PLLC

(57) ABSTRACT

An electrolyte solution containing at least one selected from a compound represented by the following formula (1-1) (wherein $Rf^{111}$s are the same as or different from each other and are each a C2-C4 fluorinated alkenyl group), a compound represented by the following formula (1-2) (wherein $R^{121}$ is a C1-C4 alkyl group; and $Rf^{121}$ is a C2-C4 fluorinated alkenyl group), and a compound represented by the following formula (1-3) (wherein $Rf^{131}$ is a C1-C3 fluorinated alkyl group; and $R^{131}$ is a C6-C12 aryl group):

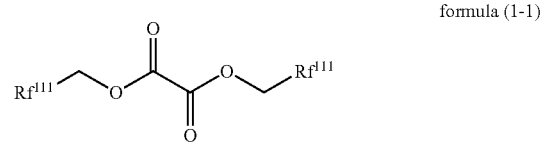

formula (1-1)

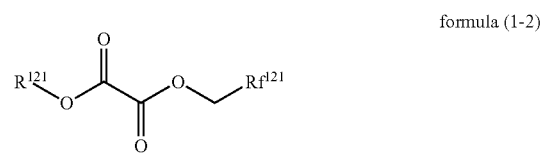

formula (1-2)

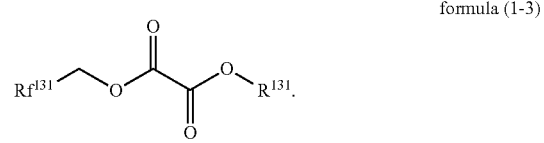

formula (1-3)

8 Claims, No Drawings

(56) References Cited

OTHER PUBLICATIONS

International Preliminary Report in Patentability dated May 12, 2020 with Written Opinion in International Application No. PCT/JP2018/039903.
International Preliminary Report in Patentability dated May 12, 2020 with Written Opinion in International Application No. PCT/JP2018/039907.
International Preliminary Report in Patentability dated May 12, 2020 with Written Opinion in International Application No. PCT/JP2018/039910.
Partial European Search Report dated Jun. 17, 2021 from the European Patent Office in counterpart Application No. 18876381.7.
International Search Report for PCT/JP2018/039910 dated Jan. 22, 2019 [PCT/ISA/210].
Extended European Search Report dated Oct. 11, 2021 from the European Patent Office in counterpart EP application No. 18876381.7.

* cited by examiner

ELECTROLYTIC SOLUTION, ELECTROCHEMICAL DEVICE, LITHIUM-ION SECONDARY CELL, AND MODULE

CROSS REFERENCE TO RELATED APPLICATIONS

This application is a National Stage of International Application No. PCT/JP2018/039910 filed Oct. 26, 2018, claiming priority based on Japanese Patent Application No. 2017-216708 filed Nov. 9, 2017.

TECHNICAL FIELD

The invention relates to electrolyte solutions, electrochemical devices, lithium ion secondary batteries, and modules.

BACKGROUND ART

Current electric appliances demonstrate a tendency to have a reduced weight and a smaller size, which leads to development of electrochemical devices such as lithium-ion secondary batteries having a high energy density. Further, electrochemical devices such as lithium-ion secondary batteries are desired to have improved characteristics as they are applied to more various fields. Improvement in battery characteristics will become more and more important particularly when lithium-ion secondary batteries are put in use for automobiles.

Patent Literature 1 discloses an electrolyte solution containing a lithium salt dissolved in a solvent mainly containing at least one non-aqueous solvent selected from a carbonate, ether, and lactone, wherein the solvent contains a dicarboxylic acid diester other than succinic diester or a derivative thereof and an aromatic compound having a molecular weight of 500 or lower.

Patent Literature 2 discloses a non-aqueous electrolyte solution containing an electrolyte salt dissolved in a non-aqueous solvent, wherein the non-aqueous electrolyte solution contains at least one ester compound having a specific structure.

Patent Literature 3 discloses a non-aqueous electrolyte solution secondary battery, wherein the non-aqueous electrolyte solution contains vinylene carbonate and di(2-propynyl)oxalate, the vinylene carbonate is in an amount of 0.1% by mass or more and 3% by mass or less relative to the mass of the non-aqueous electrolyte solution, the di(2-propynyl)oxalate is in an amount of 0.1% by mass or more and 2% by mass or less relative to the mass of the non-aqueous electrolyte solution, the non-aqueous electrolyte solution contains a solvent mixture of ethylene carbonate and a non-cyclic carbonate, and the ethylene carbonate is present at a proportion of 20% by volume or more and 40% by volume or less of the solvent mixture.

Patent Literature 4 discloses a secondary battery including a positive electrode, a negative electrode, and an electrolyte that contains a solvent and an electrolyte salt, wherein the solvent contains a dicarbonyl compound having a specific structure.

Patent Literature 5 discloses a secondary battery including a positive electrode and a negative electrode, as well as an electrolyte solution, wherein the electrolyte solution contains a combination of a non-aqueous solvent, an electrolyte salt, and a specific compound.

CITATION LIST

Patent Literature

Patent Literature 1: JP 2002-367674 A
Patent Literature 2: JP 2007-66864 A
Patent Literature 3: JP 2009-117383 A
Patent Literature 4: JP 2010-262800 A
Patent Literature 5: JP 2011-238373 A

SUMMARY OF INVENTION

Technical Problem

Conventional techniques fail to sufficiently improve the high-temperature storage characteristics and cycle characteristics of electrochemical devices.

The invention is made in view of the above state of the art, and aims to provide an electrolyte solution capable of improving the high-temperature storage characteristics and cycle characteristics of an electrochemical device, and an electrochemical device including the electrolyte solution.

The invention also aims to provide a novel oxalic acid ester compound.

Solution to Problem

The inventors found that the presence of a novel oxalic acid compound having a specific structure can improve the high-temperature storage characteristics and the cycle characteristics, completing the invention.

The invention relates to an electrolyte solution containing at least one selected from the group consisting of a compound represented by the following formula (1-1), a compound represented by the following formula (1-2), and a compound represented by the following formula (1-3).

The invention also relates to an electrochemical device including the electrolyte solution.

The invention also relates to a lithium ion secondary battery including the electrolyte solution.

The invention also relates to a module including the electrochemical device or the lithium ion secondary battery.

The invention also relates to a compound represented by the following formula (1-1).

The invention also relates to a compound represented by the following formula (1-2).

The invention also relates to a compound represented by the following formula (1-3).

The formula (1-1) is as follows:

[Chem. 1]

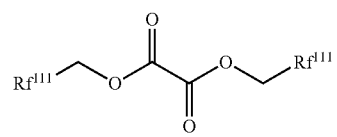

wherein $Rf^{111}$'s are the same as or different from each other and are each a C2-C4 fluorinated alkenyl group.

The formula (1-2) is as follows:

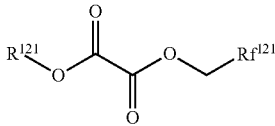

wherein $R^{121}$ is a C1-C4 alkyl group; and $Rf^{121}$ is a C2-C4 fluorinated alkenyl group.

The formula (1-3) is as follows:

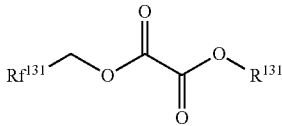

wherein $Rf^{131}$ is a C1-C3 fluorinated alkyl group; and $R^{11}$ is a C6-C12 aryl group.

Advantageous Effects of Invention

The electrolyte solution of the invention can improve the high-temperature storage characteristics and cycle characteristics of an electrochemical device. The electrochemical device including the electrolyte solution can have excellent high-temperature storage characteristics and cycle characteristics.

The compound of the invention can suitably be used as an additive of an electrolyte solution, for example.

DESCRIPTION OF EMBODIMENTS

The invention will be specifically described hereinbelow.

The electrolyte solution of the invention contains at least one compound (hereinafter, also referred to as a compound (1)) selected from the group consisting of a compound represented by the following formula (1-1), a compound represented by the following formula (1-2), and a compound represented by the following formula (1-3).

The formula (1-1) is as follows.

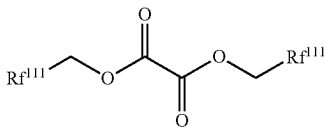

The formula (1-2) is as follows.

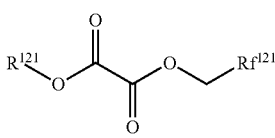

The formula (1-3) is as follows.

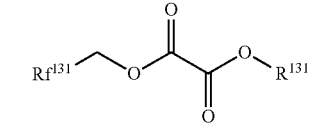

The above feature allows the electrolyte solution of the invention to improve the high-temperature storage characteristics and cycle characteristics of an electrochemical device.

The compound (1) includes at least one compound selected from the group consisting of a compound (1-1) represented by the formula (1-1), a compound (1-2) represented by the formula (1-2), and a compound (1-3) represented by the formula (1-3).

In the formula (1-1), $Rf^{111}$s are the same as or different from each other and are each a C2-C4 fluorinated alkenyl group. The fluorinated alkenyl group is an alkenyl group containing a fluorine atom.

The fluorinated alkenyl group is preferably a group obtained by replacing at least one H atom by a F atom in an ethenyl group (—CH=CH$_2$), a 1-propenyl group (—CH=CH—CH$_3$), a 1-methylethenyl group (—C(CH$_3$)=CH$_2$), a 2-propenyl group (—CH$_2$—CH=CH$_2$), a 1-butenyl group (—CH=CH—CH$_2$CH$_3$), a 2-methyl-1-propenyl group (—CH=C(CH$_3$)—CH$_3$), a 1-methyl-1-propenyl group (—C(CH$_3$)=CH—CH$_3$), a 1-ethylethenyl group (—C(CH$_2$CH$_3$)=CH$_2$), a 2-butenyl group (—CH$_2$—CH=CH$_2$—CH$_3$), a 2-methyl-2-propenyl group (—CH$_2$—C(CH$_3$)=CH$_2$), a 1-methyl-2-propenyl group (—CH(CH$_3$)—CH=CH$_2$), a 3-butenyl group (—CH$_2$CH$_2$—CH=CH$_2$), a 1-methylene-2-propenyl group (—C(=CH$_2$)—CH=CH$_2$), a 1,3-butadienyl group (—CH=CH—CH=CH$_2$), a 2,3-butadienyl group (—CH$_2$—CH=C=CH$_2$), a 1-methyl-1,2-propadienyl group (—C(CH$_3$)=C=CH$_2$), or a 1,2-butadienyl group (—CH=C=CH—CH$_3$).

Preferred is a group obtained by replacing at least one H atom by a F atom in an ethenyl group (—CH=CH$_2$), a 1-propenyl group (—CH=CH—CH$_3$), a 2-propenyl group (—CH$_2$—CH=CH$_2$), a 1-methylethenyl group (—C(CH$_3$)=CH$_2$), a 1-butenyl group (—CH=CH—CH$_2$CH$_3$), a 2-butenyl group (—CH$_2$—CH=CH$_2$—CH$_3$), a 2-methyl-2-propenyl group (—CH$_2$—C(CH$_3$)=CH$_2$), or a 3-butenyl group (—CH$_2$CH$_2$—CH=CH$_2$), more preferred is a group obtained by replacing at least one H atom by a F atom in an ethenyl group (—CH=CH$_2$), a 1-propenyl group (—CH=CH—CH$_3$), a 2-propenyl group (—CH$_2$—CH=CH$_2$), a 1-methylethenyl group (—C(CH$_3$)=CH$_2$), or a 1-butenyl group (—CH=CH—CH$_2$CH$_3$).

In the formula (1-1), the two $Rf^{111}$s are the same as or different from each other. Still, they are preferably the same as each other. That the two $Rf^{111}$s are the same means they have the same molecular formula and are not in the relationship of structural isomerism. Thus, when they are in the relationship of stereoisomerism and are different only in the stereostructure, such as the case of cis-trans isomers, they are treated as the same.

In the formula (1-2), $R^{121}$ is a C1-C4 alkyl group. $R^{121}$ preferably has a carbon number of 1 to 3, more preferably 1 to 2.

$R^{121}$ is preferably a methyl group (—CH$_3$) or an ethyl group (—CH$_2$CH$_3$).

The alkyl group is preferably free from a fluorine atom, more preferably free from a halogen atom.

In the formula (1-2), $Rf^{121}$ is a C2-C4 fluorinated alkenyl group. Examples of the fluorinated alkenyl group for $Rf^{121}$ include the same groups as those mentioned as examples for the fluorinated alkenyl group for $Rf^{111}$.

In the formula (1-3), $Rf^{131}$ is a C1-C3 fluorinated alkyl group. $Rf^{131}$ preferably has a carbon number of 1 to 2.

Examples of the fluorinated alkyl group include —$CF_3$, —$CF_2H$, —$CFH_2$, —$CF_2CF_3$, —$CF_2CF_2H$, —$CF_2CFH_2$, —$CH_2CF_3$, —$CH_2CF_2H$, —$CH_2CFH_2$, —$CF_2CF_2CF_3$, —$CF_2CF_2CF_2H$, —$CF_2CF_2CFH_2$, —$CH_2CF_2CF_3$, —$CH_2CF_2CF_2H$, —$CH_2CF_2CFH_2$, —$CH_2CH_2CF_3$, —$CH_2CH_2CF_2H$, —$CH_2CH_2CFH_2$, —$CF(CF_3)_2$, —$CF(CF_2H)_2$, —$CF(CFH_2)_2$, —$CH(CF_3)_2$, —$CH(CF_2H)_2$, and —$CH(CFH_2)_2$. Preferred among these are —$CF_3$, —$CF_2H$, —$CFH_2$, —$CF_2CF_3$, —$CF_2CF_2H$, —$CF_2CFH_2$, —$CH_2CF_3$, —$CH_2CF_2H$, and —$CH_2CFH_2$.

In the formula (1-3), $R^{131}$ is a C6-C12 aryl group.

The aryl group preferably contains a 6-membered aromatic hydrocarbon ring and is preferably monocyclic or bicyclic.

The aryl group may be an aryl group containing a substituent or may be an aryl group free from a substituent. Examples of the substituent that may optionally be present in the aryl group include a C1-C6 alkyl group and a C1-C6 alkoxy group. Preferred among these are a methyl group (—$CH_3$), an ethyl group (—$CH_2CH_3$), a methoxy group (—$OCH_3$), and an ethoxy group (—$OCH_2CH_3$), more preferred are a methyl group (—$CH_3$) and a methoxy group (—$OCH_3$).

The aryl group is preferably free from a fluorine atom, more preferably free from a halogen atom.

Examples of $R^{131}$ include a phenyl group, a benzyl group, a tolyl group, a xylyl group, an anisyl group, and a naphthyl group. These may or may not contain a substituent. Preferred among these are a phenyl group optionally containing a substituent, an anisyl group optionally containing a substituent, and a naphthyl group optionally containing a substituent, more preferred is a phenyl group optionally containing a substituent, still more preferred is a phenyl group free from a substituent.

The phenyl group, when containing a substituent, may contain 1 to 5, preferably 1 or 2, substituents. Each substituent may bond to any of the ortho position, meta position, and para position of the phenyl group.

The naphthyl group, when containing a substituent, may contain 1 to 4, preferably 1 or 2, substituents. Each substituent may bond to any position of the naphthyl group, and the substituents preferably bond to at least one of the 5 to 8 positions.

Examples of the compound (1-1) include compounds represented by the following formulas.

[Chem. 7]

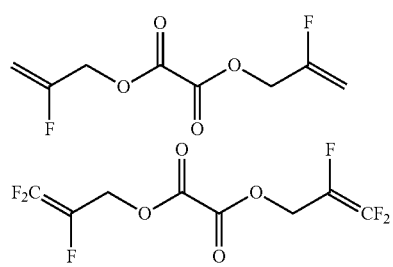

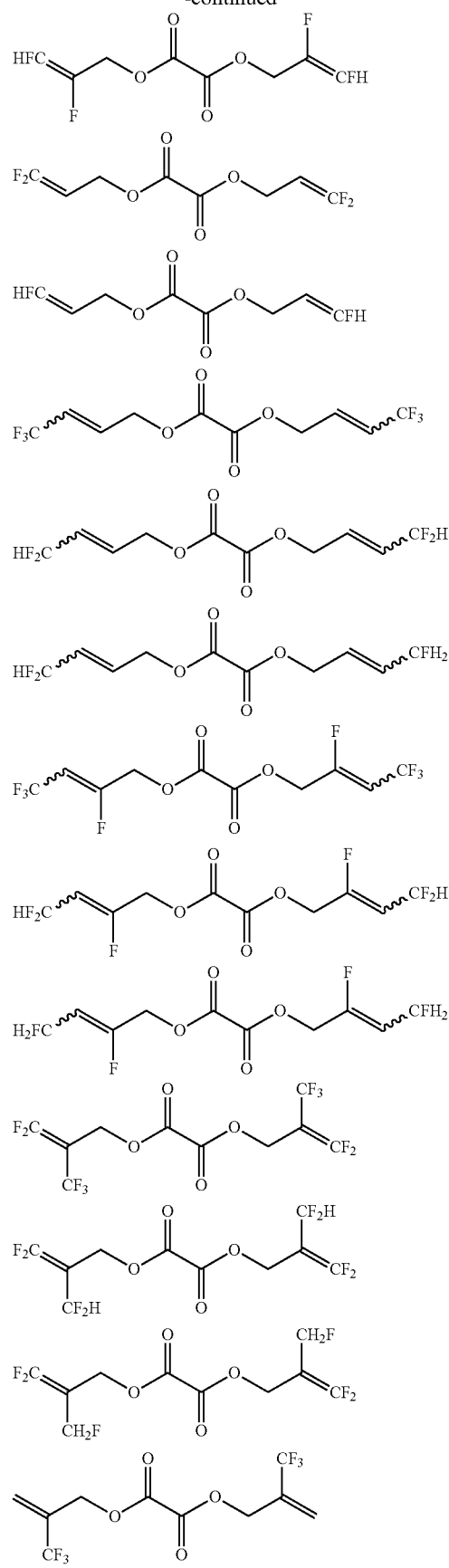

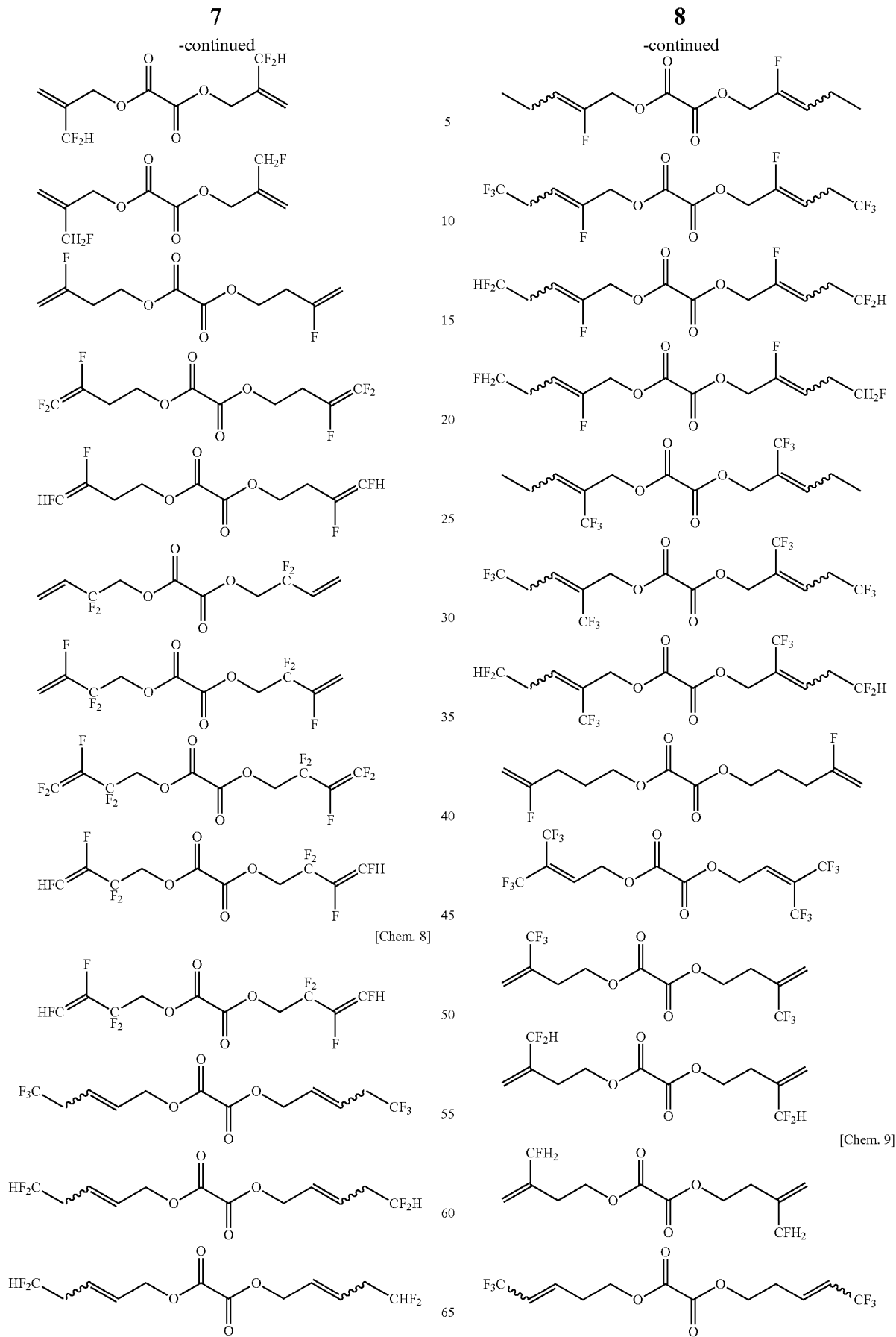

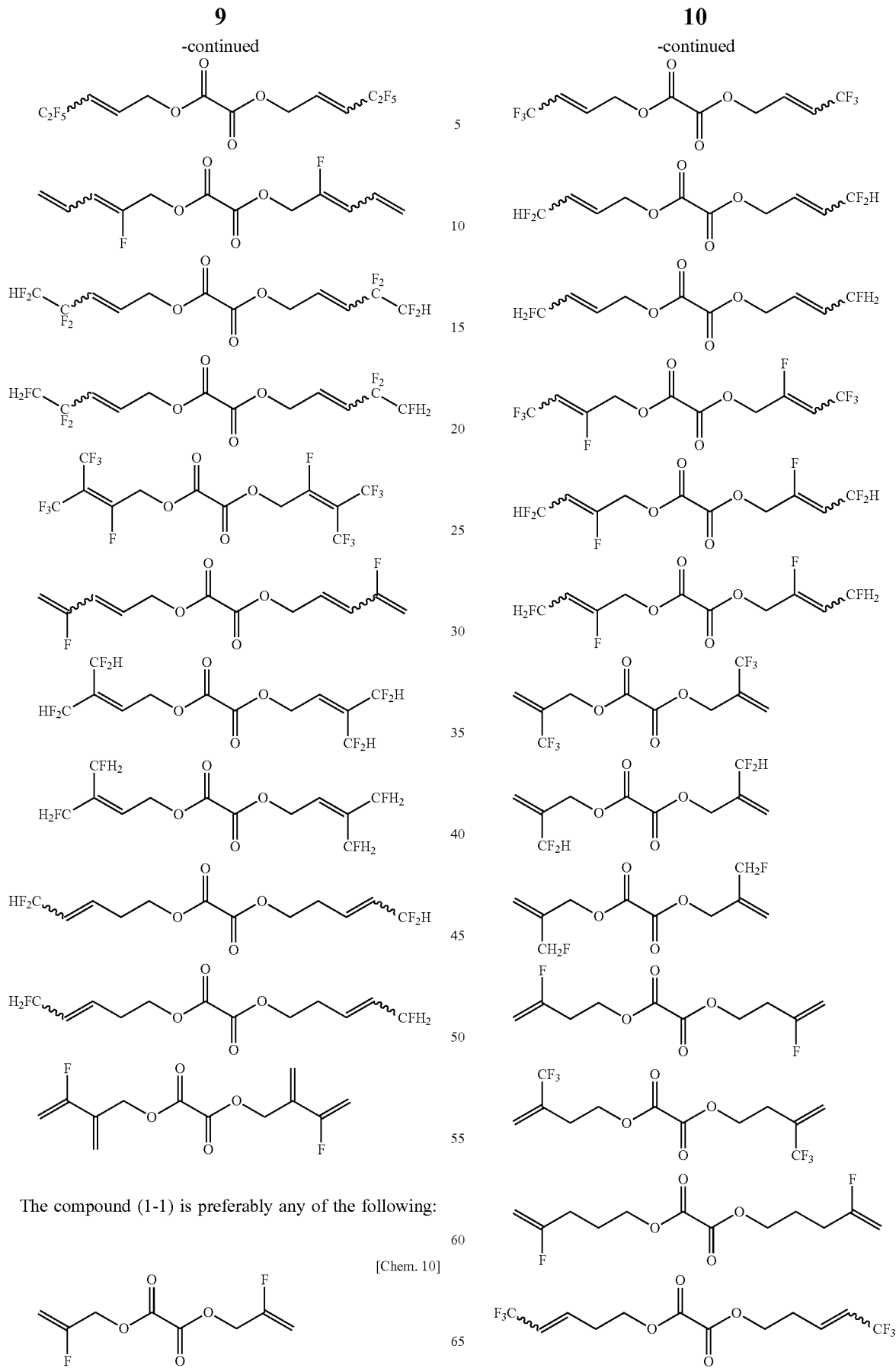
The compound (1-1) is preferably any of the following:
[Chem. 10]

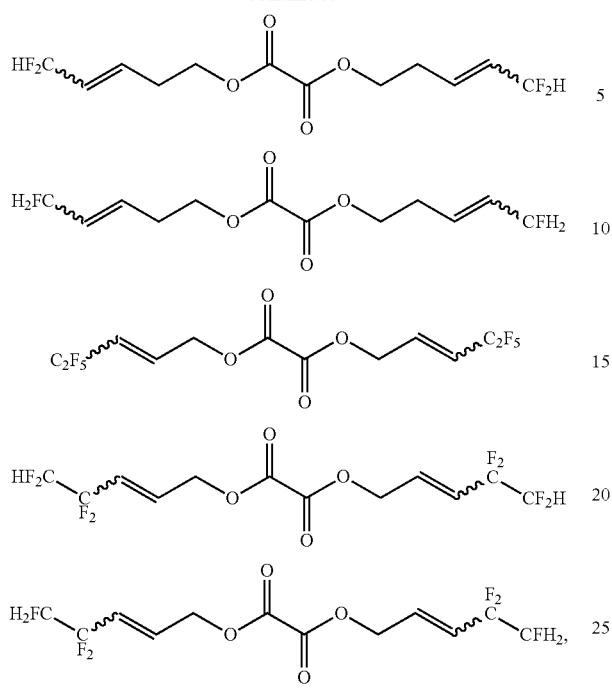
more preferably any of the following:
[Chem. 11]
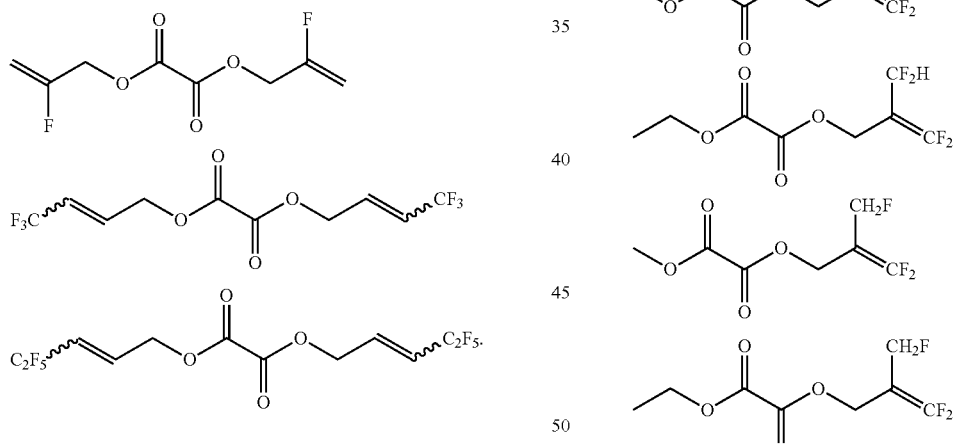
Examples of the compound (1-2) include compounds represented by the following formulas.
[Chem. 12]
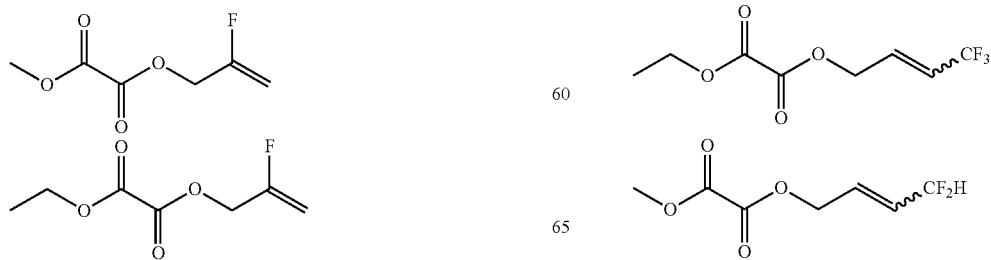

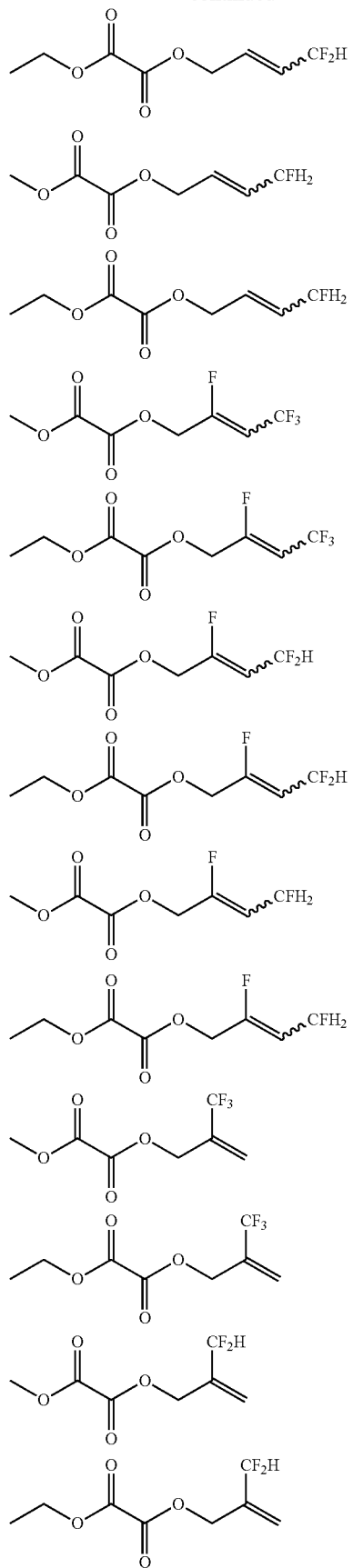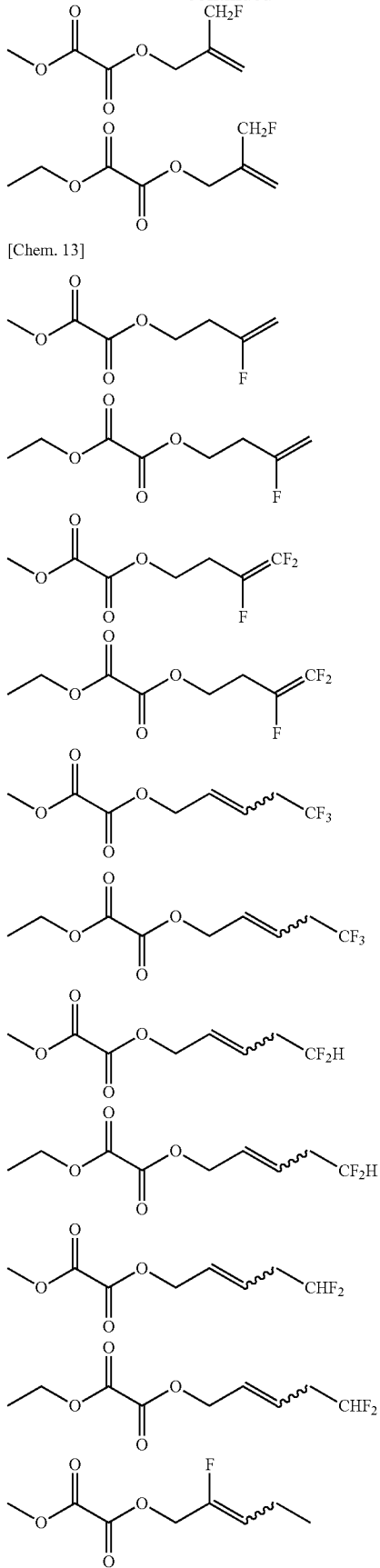

-continued
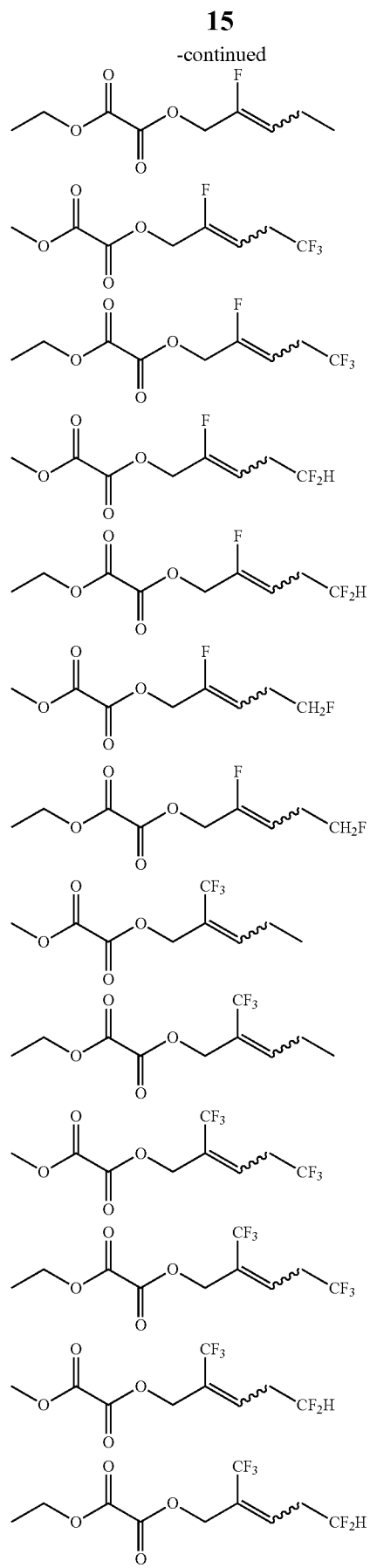
-continued
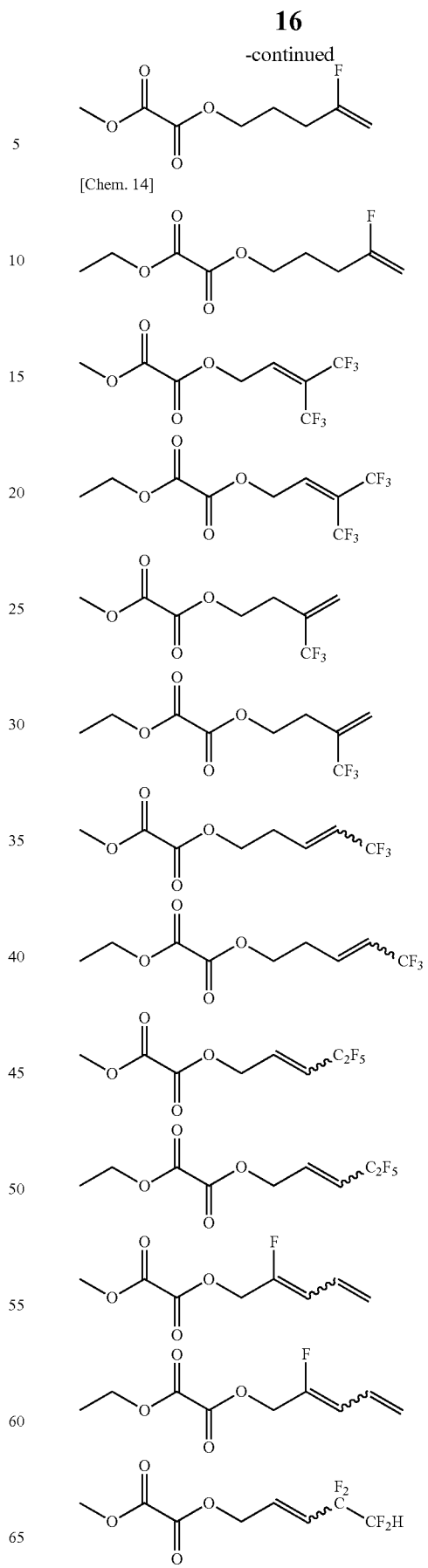
[Chem. 14]

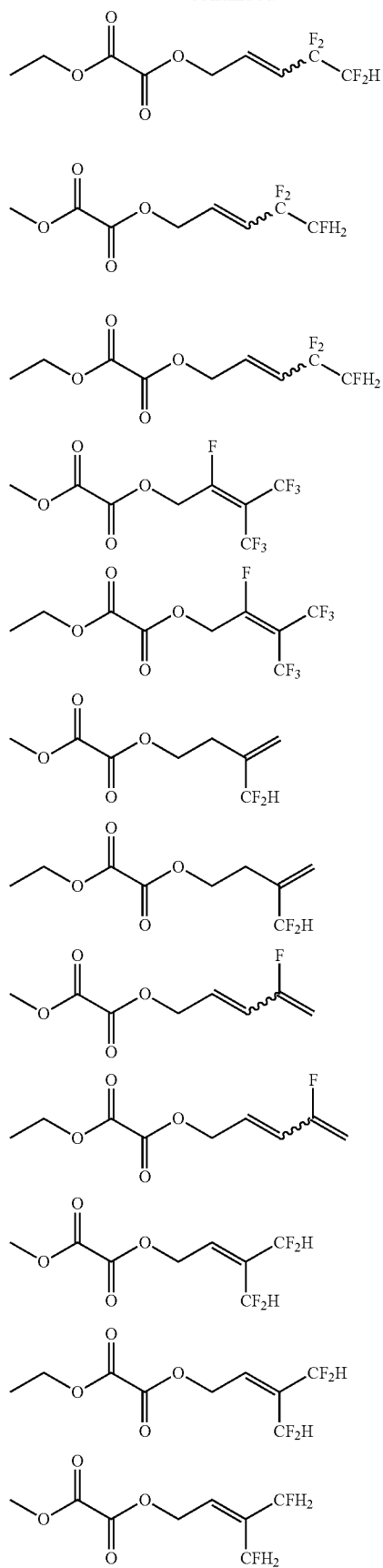
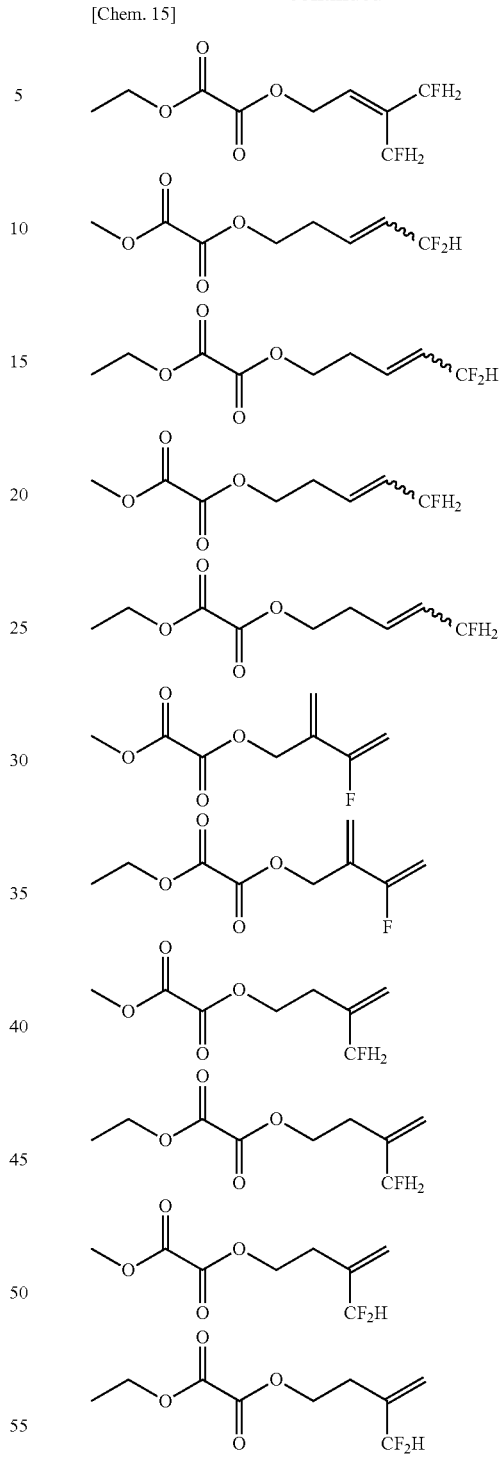
The compound (1-2) is preferably any of the following:
[Chem. 16]

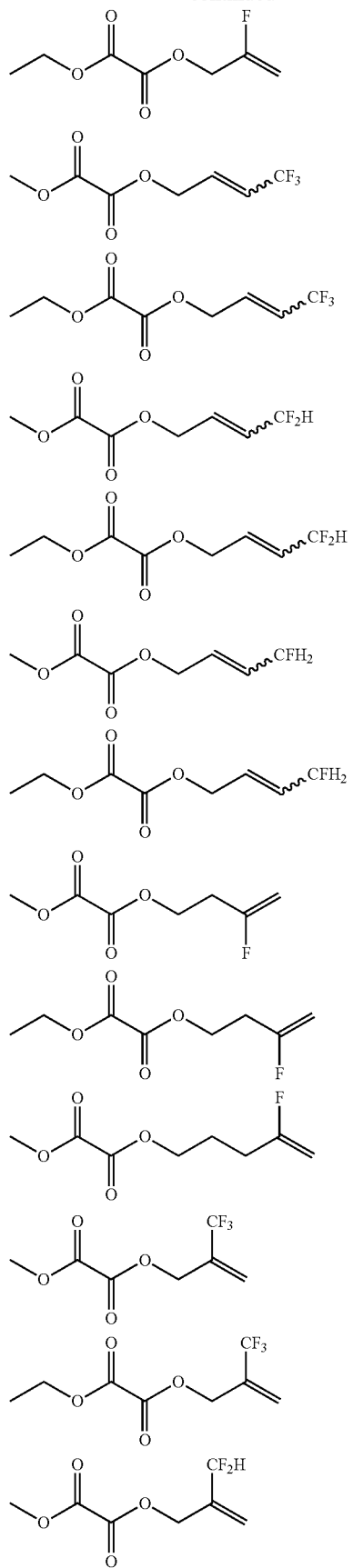
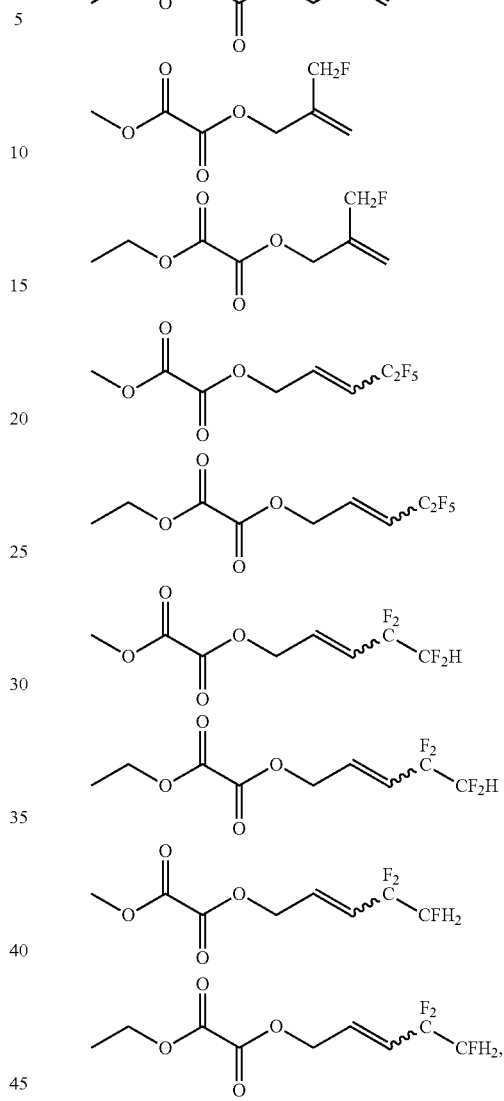
more preferably any of the following:
[Chem. 17]
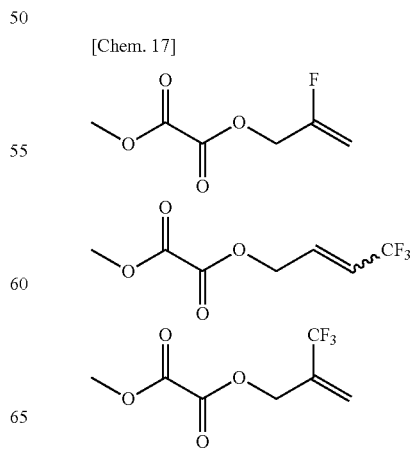

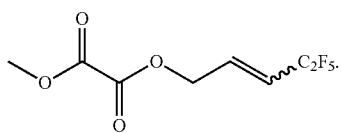
Examples of the compound (1-3) include compounds represented by the following formulas.
[Chem. 18]
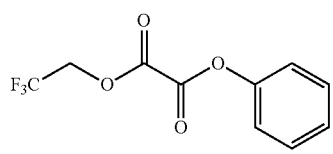
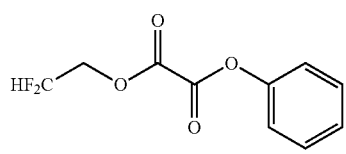
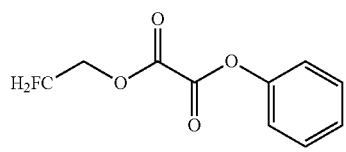
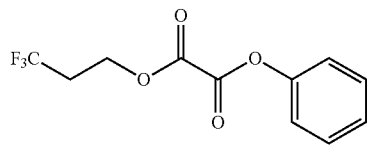
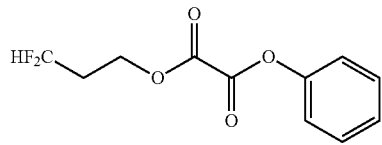
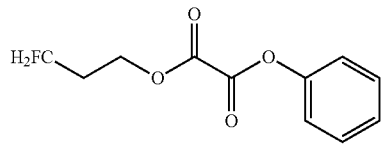
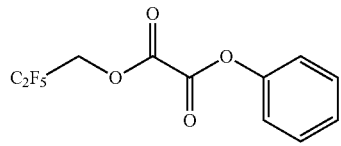
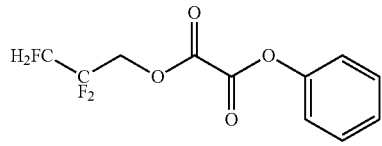
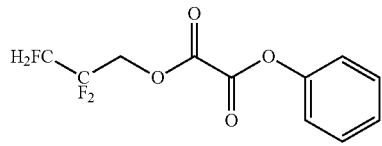
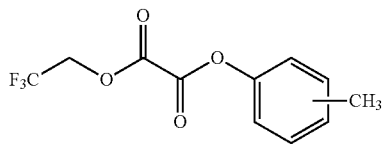
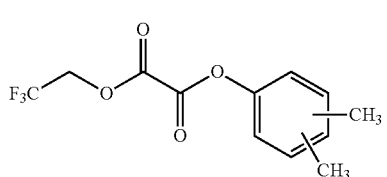
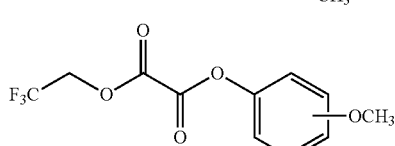
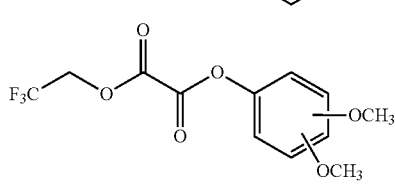
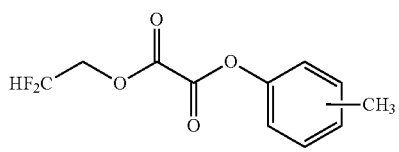
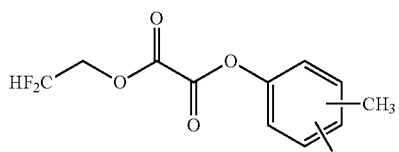
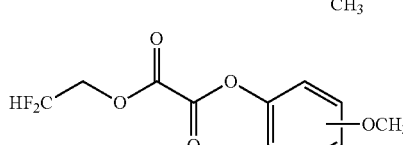
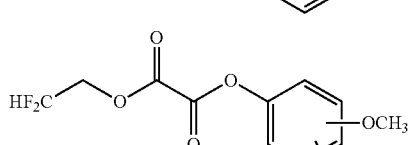
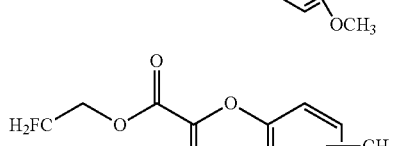
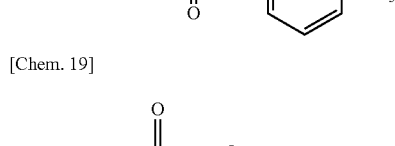
[Chem. 19]
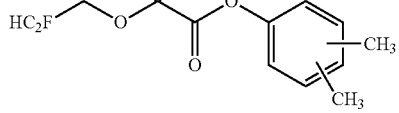

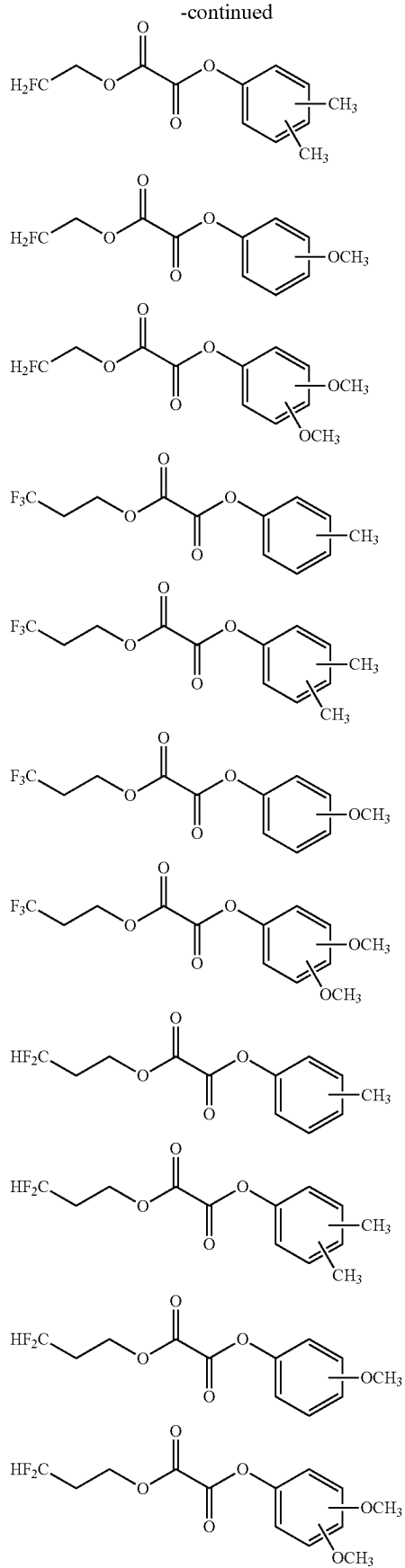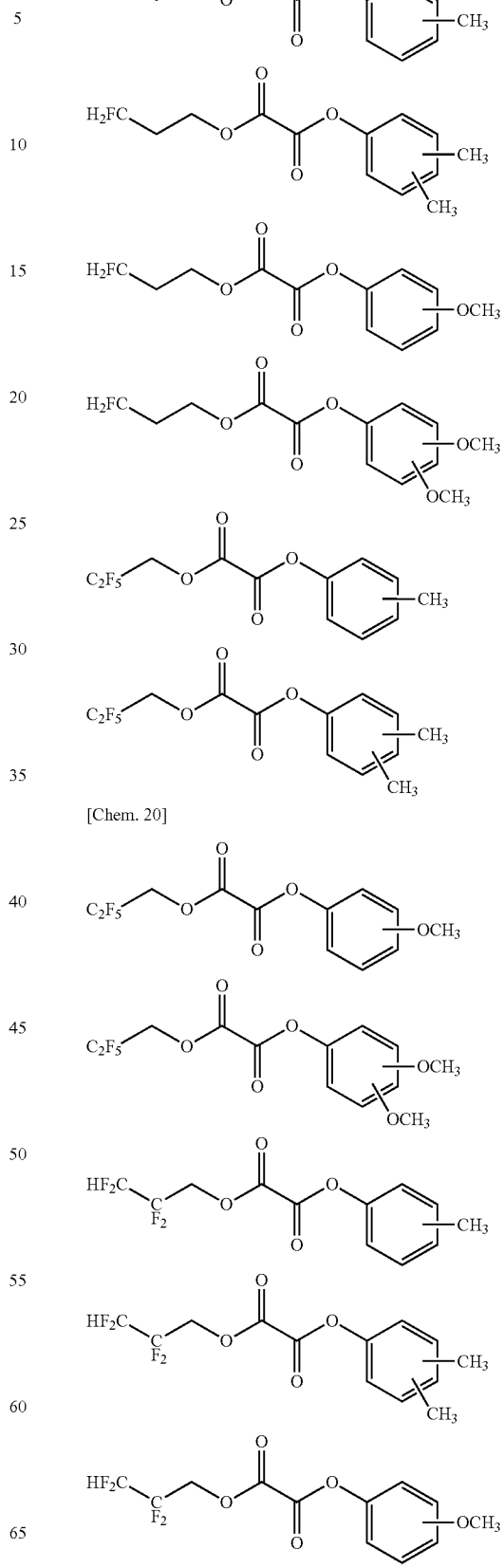

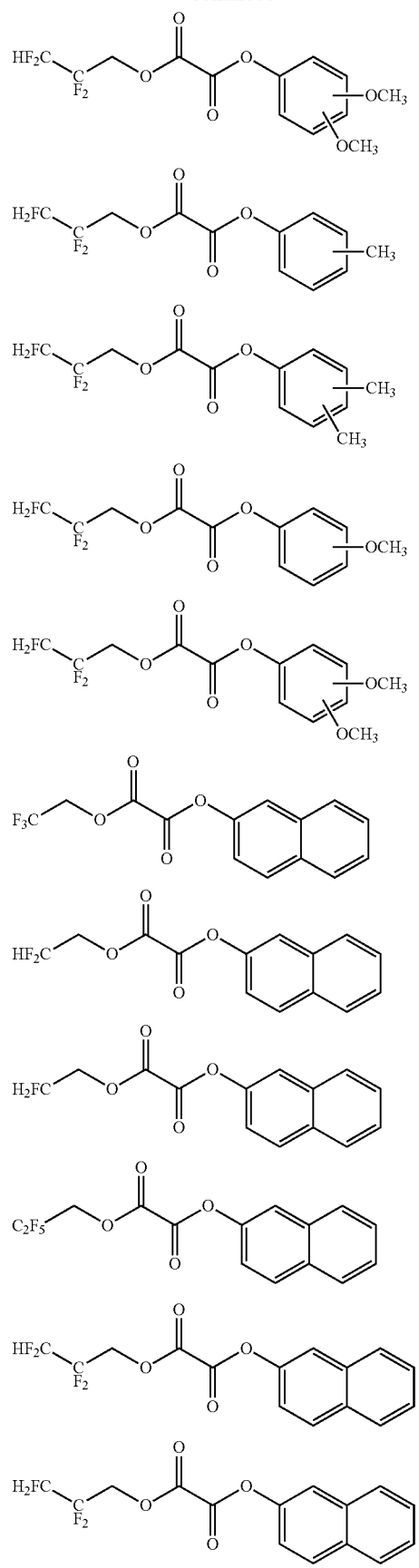
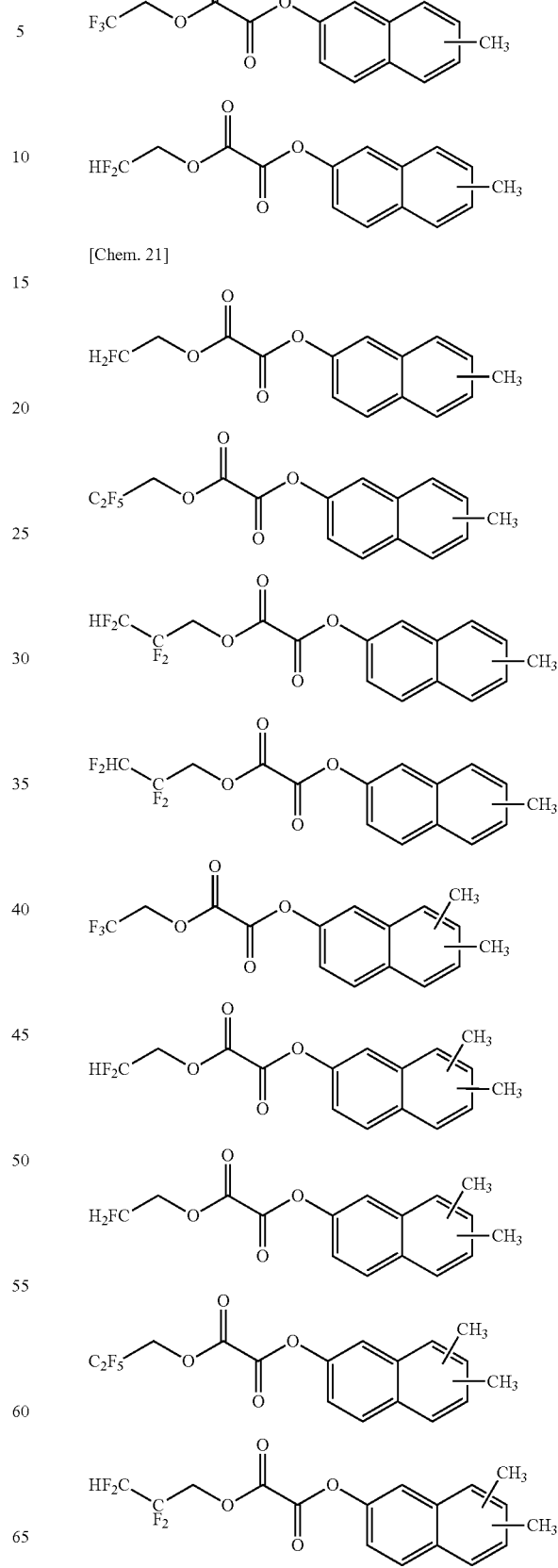

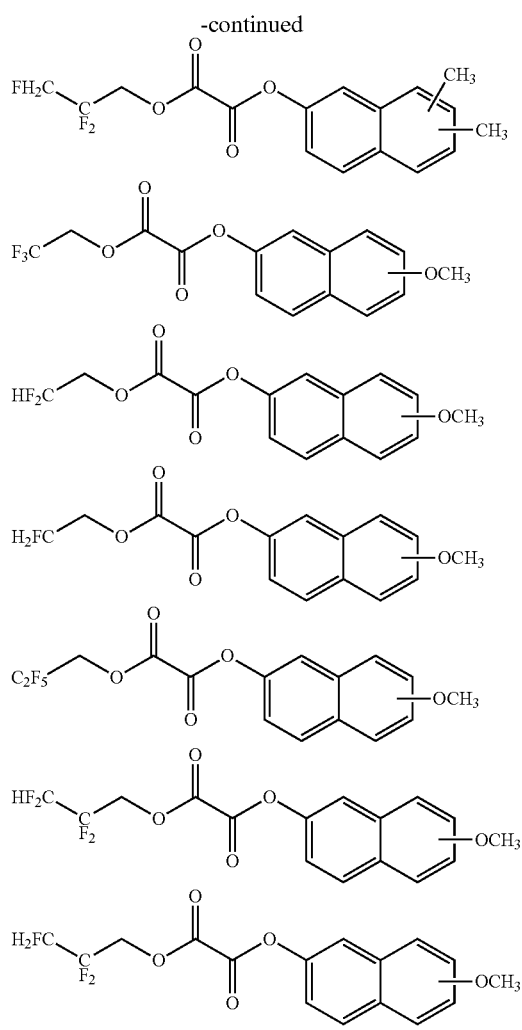
The compound (1-3) is preferably any of the following:
[Chem. 22]
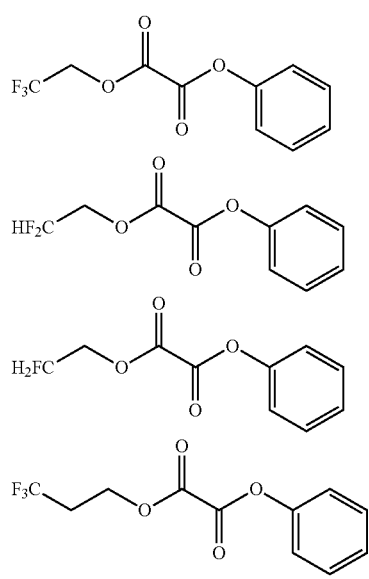
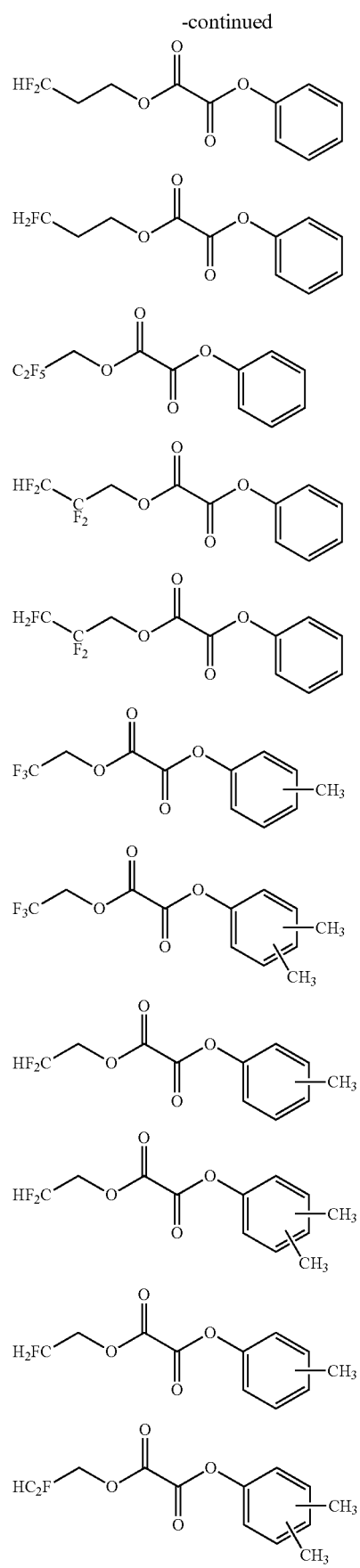

-continued
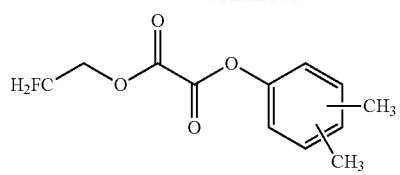
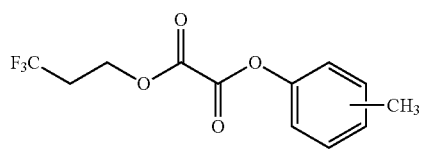
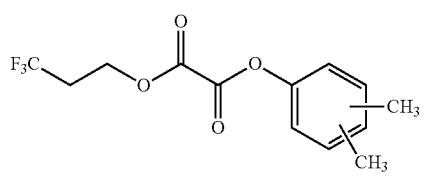
[Chem. 23]
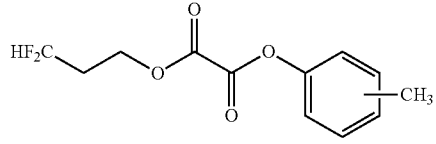
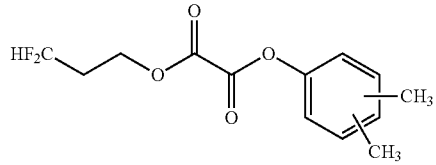
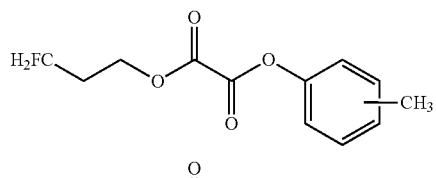
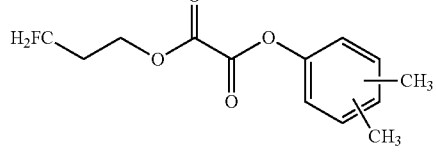
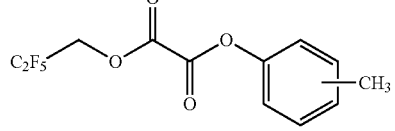
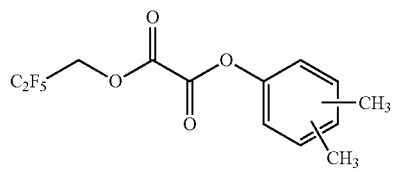
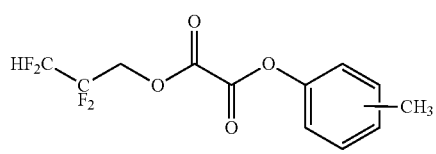
-continued
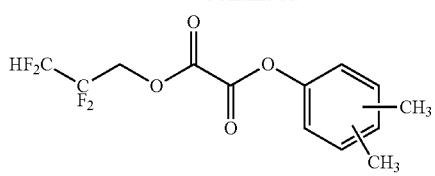
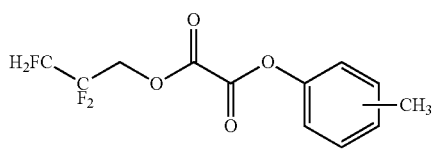
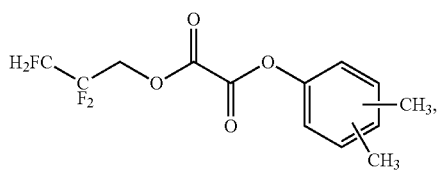
more preferably any of the following:
[Chem. 24]
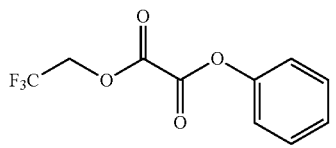
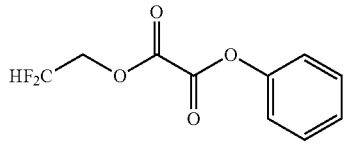
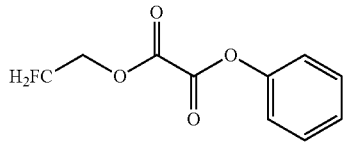
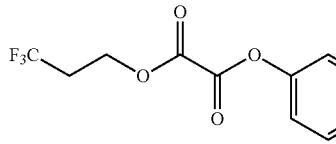
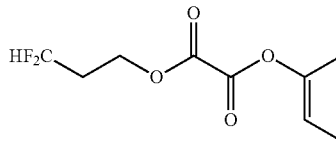
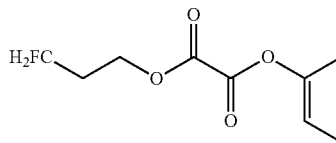
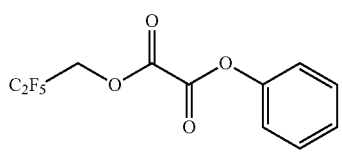

-continued

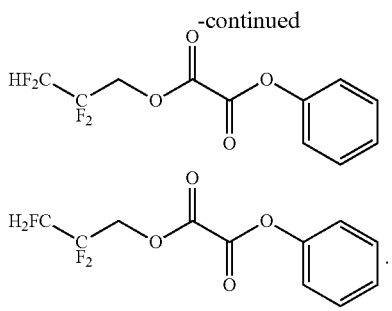

One compound (1) may be used alone, or two or more thereof may be used in combination.

The compounds (1-1), (1-2), and (1-3) are novel compounds, and are each an aspect of the invention.

The compound (1-1) can suitably be produced by a production method (1) including a step (1-1) of reacting a compound (11) represented by the following formula (11):

[Chem. 25]

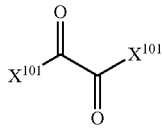

(wherein $X^{101}$ is a halogen atom) with a compound (12) represented by the following formula (12):

[Chem. 26]

(wherein $Rf^{111}$ is defined as described above) to provide a compound (1-1) represented by the formula (1-1).

In the formula (11), $X^{101}$ is a halogen atom. Examples of the halogen atom include a fluorine atom, a chlorine atom, a bromine atom, and an iodine atom. Preferred among these is a chlorine atom.

In the reaction of the step (1-1), the compound (12) is preferably used in an amount of 2.0 to 3.0 mol, more preferably 2.0 to 2.4 mol, relative to 1 mol of the compound (11).

The reaction in the step (1-1) is preferably performed in the presence of a base. Examples of the base include an amine and an inorganic base.

Examples of the amine include triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, N-methylmorpholine, 1,8-diazabicyclo[5,4,0]-7-undecene (DBU), 1,5-diazabicyclo[4,3,0]-5-nonene, 1,4-diazabicyclo[2,2,2]octane (DABCO), 4-dimethylaminopyridine (DMAP), and Proton Sponge.

Examples of the inorganic base include lithium hydroxide, potassium hydroxide, sodium hydroxide, calcium hydroxide, lithium carbonate, sodium carbonate, potassium carbonate, sodium hydrogen carbonate, potassium hydrogen carbonate, caesium carbonate, caesium hydrogen carbonate, lithium hydrogen carbonate, caesium fluoride, potassium fluoride, sodium fluoride, lithium chloride, and lithium bromide.

The base is preferably an amine, more preferably triethylamine or pyridine, among these.

The base is preferably used in an amount of 2.0 to 3.0 mol, more preferably 2.0 to 2.4 mol, relative to 1 mol of the compound (11).

The reaction in the step (1-1) may be performed in a solvent. The solvent is preferably an organic solvent. Examples thereof include non-aromatic hydrocarbon solvents such as pentane, hexane, heptane, octane, cyclohexane, decahydronaphthalene, n-decane, isododecane, and tridecane; aromatic hydrocarbon solvents such as benzene, toluene, xylene, tetralin, veratrole, diethyl benzene, methyl naphthalene, nitrobenzene, o-nitrotoluene, mesitylene, indene, and diphenyl sulfide; ketones such as acetone, methyl ethyl ketone, methyl isobutyl ketone, acetophenone, propiophenone, diisobutyl ketone, and isophorone; halogenated hydrocarbon solvents such as dichloromethane, carbon tetrachloride, chloroform, and chlorobenzene; ether solvents such as diethyl ether, tetrahydrofuran, diisopropyl ether, methyl t-butyl ether, dioxane, dimethoxyethane, diglyme, phenetole, 1,1-dimethoxycyclohexane, and diisoamyl ether; ester solvents such as ethyl acetate, isopropyl acetate, diethyl malonate, 3-methoxy-3-methylbutyl acetate, γ-butyrolactone, ethylene carbonate, propylene carbonate, dimethyl carboante, and α-acetyl-γ-butyrolactone; nitrile solvents such as acetonitrile and benzonitrile; sulfoxide solvents such as dimethyl sulfoxide and sulfolane; and amide solvents such as N,N-dimethylformamide, N,N-dimethylacetamide, N-methylpyrrolidone, 1,3-dimethyl-2-imidazolidinone, N,N-dimethylacrylamide, N,N-dimethylacetoacetamide, N,N-diethylformamide, and N,N-diethylacetamide.

Preferred among these are halogenated hydrocarbon solvents, more preferred are dichloromethane and carbon tetrachloride.

The temperature of the reaction in the step (1-1) is preferably 0° C. to 25° C., more preferably 0° C. to 10° C.

The duration of the reaction in the step (1-1) is preferably 2 to 24 hours, more preferably 2 to 12 hours.

The compound (1-2) can suitably be produced by a production method (2) including a step (1-2) of reacting a compound (21) represented by the following formula (21):

[Chem. 27]

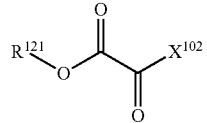

(wherein $R^{121}$ is defined as described above; and $X^{102}$ is a halogen atom) with a compound (22) represented by the following formula (22):

[Chem. 28]

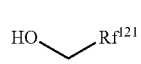

(wherein $Rf^{12}$ is defined as described above) to provide a compound (1-2) represented by the formula (1-2).

In the formula (21), $X^{102}$ is a halogen atom. Examples of the halogen atom include a fluorine atom, a chlorine atom, a bromine atom, and an iodine atom. Preferred among these is a chlorine atom.

In the reaction of the step (1-2), the compound (22) is preferably used in an amount of 1.0 to 1.5 mol, more preferably 1.0 to 1.2 mol, relative to 1 mol of the compound (21).

The reaction in the step (1-2) is preferably performed in the presence of a base. Examples of the base include the same bases as the bases mentioned as examples for the step (1-1) of the production method (1).

The base is preferably used in an amount of 1.0 to 1.5 mol, more preferably 1.0 to 1.2 mol, relative to 1 mol of the compound (21).

The reaction in the step (1-2) may be performed in a solvent. Examples of the solvent include the same solvents as the solvents mentioned as examples for the step (1-1) of the production method (1).

The temperature and the duration of the reaction in the step (1-2) can be the same conditions for the step (1-1) of the production method (1).

The compound (1-3) can suitably be produced by a production method (3) including a step (1-3) of reacting a compound (31) represented by the following formula (31):

[Chem. 29]

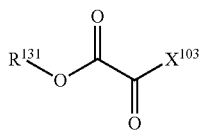

(wherein $R^{131}$ is defined as described above; and $X^{103}$ is a halogen atom) with a compound (32) represented by the following formula (32):

[Chem. 30]

(wherein $Rf^{131}$ is defined as described above) to provide a compound (1-3) represented by the formula (1-3).

In the formula (31), $X^{103}$ is a halogen atom. Examples of the halogen atom include a fluorine atom, a chlorine atom, a bromine atom, and an iodine atom. Preferred is a chlorine atom.

The reaction in the step (1-3) can be performed under the same conditions as the conditions mentioned as examples for the step (1-2) of the production method (2).

In any of the aforementioned production methods, completion of the step may be followed by separation and purification of the product by a step such as evaporation of the solvent, column chromatography, or recrystallization.

The electrolyte solution of the invention preferably contains the compound (1) in an amount of 0.001 to 20% by mass relative to the electrolyte solution. The compound (1) in an amount within the above range can lead to more improved high-temperature storage characteristics and cycle characteristics of an electrochemical device. The amount of the compound (1) is more preferably 0.01% by mass or more, still more preferably 0.1% by mass or more, particularly preferably 0.5% by mass or more, while more preferably 15% by mass or less, still more preferably 10% by mass or less, further more preferably 7.0% by mass or less, particularly preferably 5.0% by mass or less.

The electrolyte solution of the invention preferably contains a solvent other than the compound (1).

The solvent preferably includes at least one selected from the group consisting of a carbonate and a carboxylate.

The carbonate may be either a cyclic carbonate or an acyclic carbonate.

The cyclic carbonate may be either a non-fluorinated cyclic carbonate or a fluorinated cyclic carbonate.

An example of the non-fluorinated cyclic carbonate is a non-fluorinated saturated cyclic carbonate. Preferred is a non-fluorinated saturated alkylene carbonate containing a C2-C6 alkylene group, more preferred is a non-fluorinated saturated alkylene carbonate containing a C2-C4 alkylene group.

In order to give high permittivity and suitable viscosity, the non-fluorinated saturated cyclic carbonate preferably includes at least one selected from the group consisting of ethylene carbonate, propylene carbonate, cis-2,3-pentylene carbonate, cis-2,3-butylene carbonate, 2,3-pentylene carbonate, 2,3-butylene carbonate, 1,2-pentylene carbonate, 1,2-butylene carbonate, and butylene carbonate.

One non-fluorinated saturated cyclic carbonate may be used alone, or two or more thereof may be used in any combination at any ratio.

The non-fluorinated saturated cyclic carbonate, when contained, is preferably present in an amount of 5 to 90% by volume, more preferably 10 to 60% by volume, still more preferably 15 to 45% by volume, relative to the solvent.

The fluorinated cyclic carbonate is a cyclic carbonate containing a fluorine atom. A solvent containing a fluorinated cyclic carbonate can suitably be used at high voltage.

The term "high voltage" herein means a voltage of 4.2 V or higher. The upper limit of the "high voltage" is preferably 4.9 V.

The fluorinated cyclic carbonate may be either a fluorinated saturated cyclic carbonate or a fluorinated unsaturated cyclic carbonate.

The fluorinated saturated cyclic carbonate is a saturated cyclic carbonate containing a fluorine atom. Specific examples thereof include a compound represented by the following formula (A):

[Chem. 31]

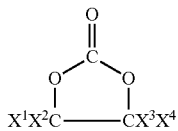

(A)

(wherein $X^1$ to $X^4$ are the same as or different from each other, and are each —H, —CH$_3$, —C$_2$H$_5$, —F, a fluorinated alkyl group optionally containing an ether bond, or a fluorinated alkoxy group optionally containing an ether bond; at least one selected from $X^1$ to $X^4$ is —F, a fluorinated alkyl group optionally containing an ether bond, or a fluorinated alkoxy group optionally containing an ether bond). Examples of the fluorinated alkyl group include —CF$_3$, —CF$_2$H, and —CH$_2$F.

The presence of the fluorinated saturated cyclic carbonate in the electrolyte solution of the invention when applied to a high-voltage lithium ion secondary battery, for example, can improve the oxidation resistance of the electrolyte solution, resulting in stable and excellent charge and discharge characteristics.

The term "ether bond" herein means a bond represented by —O—.

In order to give a good permittivity and oxidation resistance, one or two of $X^1$ to $X^4$ is/are each preferably —F, a fluorinated alkyl group optionally containing an ether bond, or a fluorinated alkoxy group optionally containing an ether bond.

In anticipation of a decrease in viscosity at low temperature, an increase in flash point, and improvement in solubility of an electrolyte salt, $X^1$ to $X^4$ are each preferably —H, —F, a fluorinated alkyl group (a), a fluorinated alkyl group (b) containing an ether bond, or a fluorinated alkoxy group (c).

The fluorinated alkyl group (a) is a group obtainable by replacing at least one hydrogen atom of an alkyl group by a fluorine atom. The fluorinated alkyl group (a) preferably has a carbon number of 1 to 20, more preferably 1 to 17, still more preferably 1 to 7, particularly preferably 1 to 5.

Too large a carbon number may cause poor low-temperature characteristics and low solubility of an electrolyte salt. Too small a carbon number may cause low solubility of an electrolyte salt, low discharge efficiency, and increased viscosity, for example.

Examples of the fluorinated alkyl group (a) having a carbon number of 1 include $CFH_2$—, $CF_2H$—, and $CF_3$—. In order to give good high-temperature storage characteristics, particularly preferred is $CF_2H$— or $CF_3$—. Most preferred is $CF_3$—.

In order to give good solubility of an electrolyte salt, preferred examples of the fluorinated alkyl group (a) having a carbon number of 2 or greater include fluorinated alkyl groups represented by the following formula (a-1):

$$R^1\text{-}R^2 \quad (a\text{-}1)$$

wherein $R^1$ is an alkyl group having a carbon number of 1 or greater and optionally containing a fluorine atom; $R^2$ is a C1-C3 alkylene group optionally containing a fluorine atom; and at least one selected from $R^1$ and $R^2$ contains a fluorine atom.

$R^1$ and $R^2$ each may further contain an atom other than carbon, hydrogen, and fluorine atoms.

$R^1$ is an alkyl group having a carbon number of 1 or greater and optionally containing a fluorine atom. $R^1$ is preferably a C1-C16 linear or branched alkyl group. The carbon number of $R^1$ is more preferably 1 to 6, still more preferably 1 to 3.

Specifically, for example, $CH_3$—, $CH_3CH_2$—, $CH_3CH_2CH_2$—, $CH_3CH_2CH_2CH_2$—, and groups represented by the following formulae:

[Chem. 32]

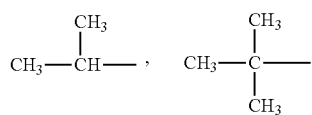

may be mentioned as linear or branched alkyl groups for $R^1$.

Examples of $R^1$ which is a linear alkyl group containing a fluorine atom include $CF_3$—, $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CH_2CF_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CF_2CF_2CH_2CH_2$—, $CF_3CF_2CF_2CF_2CH_2$—, $CF_3CF_2CH_2CF_2CH_2$—, $CF_3CF_2CF_2CF_2CH_2$—, $CF_3CF_2CH_2CF_2CH_2$—, $HCF_2$—, $HCF_2CH_2$—, $HCF_2CF_2$—, $HCF_2CH_2CH_2$—, $HCF_2CF_2CH_2$—, $HCF_2CH_2CF_2$—, $HCF_2CF_2CH_2CH_2$—, $HCF_2CH_2CF_2CH_2$—, $HCF_2CF_2CF_2CF_2$—, $HCF_2CF_2CH_2CH_2CH_2$—, $HCF_2CH_2CF_2CH_2CH_2$—, $HCF_2CF_2CF_2CH_2CH_2$—, $HCF_2CF_2CF_2CF_2CH_2$—, $FCH_2$—, $FCH_2CH_2$—, $FCH_2CF_2$—, $FCH_2CF_2CH_2$—, $FCH_2CF_2CF_2$—, $CH_3CF_2CH_2$—, $CH_3CF_2CF_2$—, $CH_3CF_2CH_2CF_2$—, $CH_3CF_2CF_2CF_2$—, $CH_3CH_2CF_2CF_2$—, $CH_3CF_2CH_2CF_2CH_2$—, $CH_3CF_2CF_2CH_2$—, $CH_3CF_2CF_2CH_2CH_2$—, $CH_3CF_2CH_2CF_2$—, $CH_3CF_2CH_2CF_2CH_2CH_2$—, $CH_3CF_2CH_2CF_2CH_2CH_2$—, $HCFClCF_2CH_2$—, $HCF_2CFClCH_2$—, $HCF_2CFClCF_2CFClCH_2$—, and $HCFClCF_2CFClCF_2CH_2$—.

Examples of $R^1$ which is a branched alkyl group containing a fluorine atom include those represented by the following formulae.

[Chem. 33]

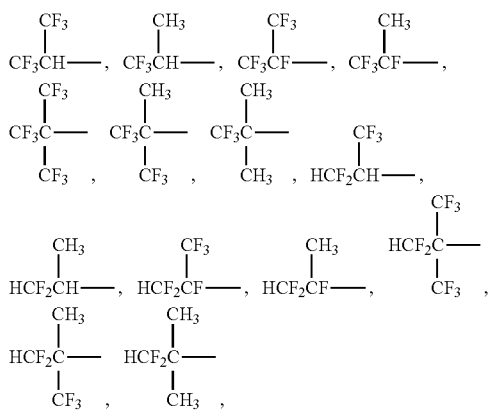

[Chem. 34]

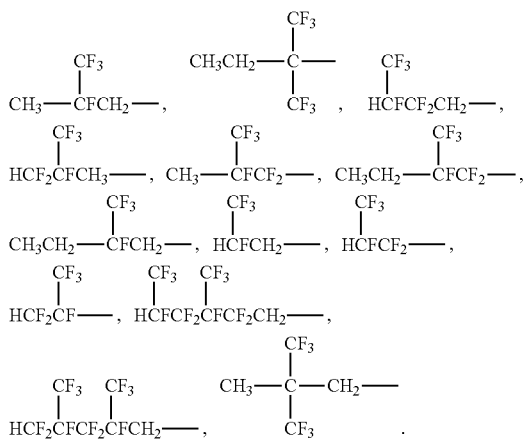

The presence of a branch such as $CH_3$— or $CF_3$— may easily cause high viscosity. Thus, the number of such branches is more preferably small (one) or zero.

$R^2$ is a C1-C3 alkylene group optionally containing a fluorine atom. $R^2$ may be either linear or branched. Examples of a minimum structural unit constituting such a linear or branched alkylene group are shown below. $R^2$ is constituted by one or combination of these units.

(i) Linear Minimum Structural Units

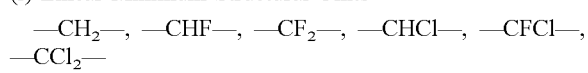

(ii) Branched Minimum Structural Units

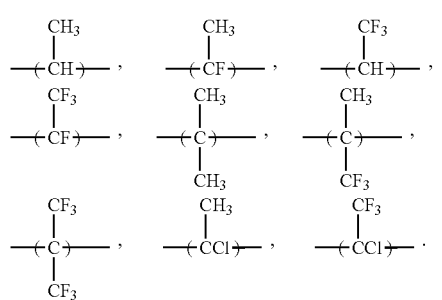

Preferred among these exemplified units are Cl-free structural units because such units may not be dehydrochlorinated by a base, and thus may be more stable.

$R^2$ which is a linear group consists only of any of the above linear minimum structural units, and is preferably —$CH_2$—, —$CH_2CH_2$—, or $CF_2$—. In order to further improve the solubility of an electrolyte salt, —$CH_2$— or —$CH_2CH_2$— is more preferred.

$R^2$ which is a branched group includes at least one of the above branched minimum structural units. A preferred example thereof is a group represented by —($CX^aX^b$)— (wherein $X^a$ is H, F, $CH_3$, or $CF_3$; $X^b$ is $CH_3$ or $CF_3$; when $X^b$ is $CF_3$, $X^a$ is H or $CH_3$). Such a group can much further improve the solubility of an electrolyte salt.

For example, $CF_3CF_2$—, $HCF_2CF_2$—, $H_2CFCF_2$—, $CH_3CF_2$—, $CF_3CHF$—, $CH_3CF_2$—, $CF_3CF_2CF_2$—, $HCF_2CF_2CF_2$—, $H_2CFCF_2CF_2$—, $CH_3CF_2CF_2$—, and those represented by the following formulae:

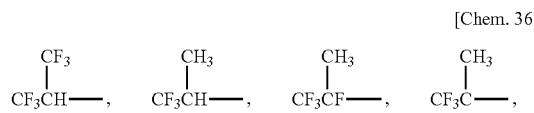

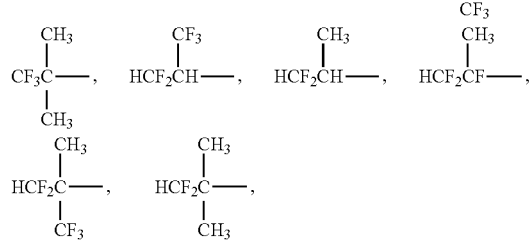

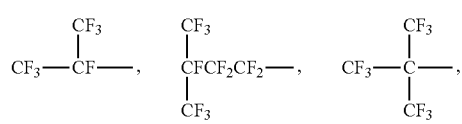

may be mentioned as preferred examples of the fluorinated alkyl group (a).

The fluorinated alkyl group (b) containing an ether bond is a group obtainable by replacing at least one hydrogen atom of an alkyl group containing an ether bond by a fluorine atom. The fluorinated alkyl group (b) containing an ether bond preferably has a carbon number of 2 to 17. Too large a carbon number may cause high viscosity of the fluorinated saturated cyclic carbonate. This may also cause the presence of many fluorine-containing groups, resulting in poor solubility of an electrolyte salt due to reduction in permittivity, and poor miscibility with other solvents. Accordingly, the carbon number of the fluorinated alkyl group (b) containing an ether bond is preferably 2 to 10, more preferably 2 to 7.

The alkylene group which constitutes the ether moiety of the fluorinated alkyl group (b) containing an ether bond is a linear or branched alkylene group. Examples of a minimum structural unit constituting such a linear or branched alkylene group are shown below.

(i) Linear Minimum Structural Units
—$CH_2$—, —CHF—, —$CF_2$—, —CHCl—, —CFCl—, —$CCl_2$—

(ii) Branched Minimum Structural Units

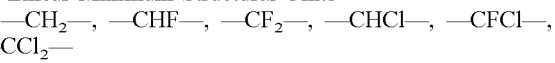

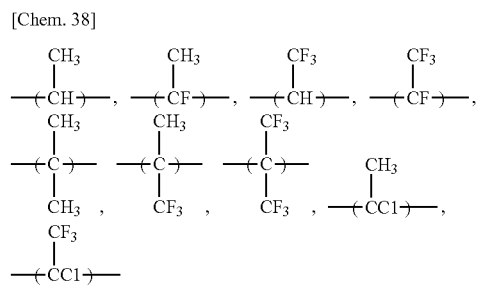

The alkylene group may be constituted by one of these minimum structural units, or may be constituted by multiple linear units (i), by multiple branched units (ii), or by a combination of a linear unit (i) and a branched unit (ii). Preferred examples will be mentioned in detail later.

Preferred among these exemplified units are Cl-free structural units because such units may not be dehydrochlorinated by a base, and thus may be more stable.

A still more preferred example of the fluorinated alkyl group (b) containing an ether bond is a group represented by the following formula (b-1):

$$R^3—(OR^4)_{n1}—\quad (b\text{-}1)$$

wherein $R^3$ is preferably a C1-C6 alkyl group optionally containing a fluorine atom; $R^4$ is preferably a C1-C4 alkylene group optionally containing a fluorine atom; n1 is an integer of 1 to 3; and at least one selected from $R^3$ and $R^4$ contains a fluorine atom.

Examples of $R^3$ and $R^4$ include the following groups, and any appropriate combination of these groups can provide the fluorinated alkyl group (b) containing an ether bond represented by the formula (b-1). Still, the groups are not limited thereto.

(1) $R^3$ is preferably an alkyl group represented by the formula: $X^c{}_3C—(R^5)_{n2}$—, wherein three $X^c$s are the same as or different from each other, and are each H or F; $R^5$ is a C1-C5 alkylene group optionally containing a fluorine atom; and n2 is 0 or 1.

When n2 is 0, $R^3$ may be $CH_3$—, $CF_3$—, $HCF_2$—, or $H_2CF$—, for example.

When n2 is 1, specific examples of $R^3$ which is a linear group include $CF_3CH_2$—, $CF_3CF_2$—, $CF_3CH_2CH_2$—, $CF_3CF_2CH_2$—, $CF_3CF_2CF_2$—, $CF_3CH_2CF_2$—, $CF_3CH_2CH_2CH_2$—, $CF_3CF_2CH_2CH_2$—, $CF_3CH_2CF_2CH_2$—, $CF_3CF_2CF_2CH_2$—, $CF_3CF_2CF_2CF_2$—, $CF_3CF_2CH_2CF_2$—, $CF_3CH_2CH_2CH_2CH_2$—, $CF_3CF_2CH_2CH_2CH_2$—, $CF_3CF_2CF_2CH_2CH_2$—, $CF_3CF_2CF_2CF_2CH_2$—, $CF_3CF_2CH_2CF_2$ CH$_2$—, CF$_3$CF$_2$CH$_2$CH$_2$CH$_2$CH$_2$—, CF$_3$CF$_2$CF$_2$CF$_2$CH$_2$CH$_2$—, CF$_3$CF$_2$CH$_2$CF$_2$CH$_2$CH$_2$—, HCF$_2$CH$_2$—, HCF$_2$CF$_2$—, HCF$_2$CH$_2$CH$_2$—, HCF$_2$CF$_2$CH$_2$—, HCF$_2$CH$_2$CF$_2$—, HCF$_2$CF$_2$CH$_2$CH$_2$—, HCF$_2$CH$_2$CF$_2$CH$_2$—, HCF$_2$CF$_2$CF$_2$CF$_2$—, HCF$_2$CF$_2$CH$_2$CH$_2$CH$_2$—, HCF$_2$CH$_2$CF$_2$CH$_2$CH$_2$—, HCF$_2$CF$_2$CF$_2$CF$_2$CH$_2$—, HCF$_2$CF$_2$CF$_2$CF$_2$CH$_2$CH$_2$—, FCH$_2$CH$_2$—, FCH$_2$CF$_2$—, FCH$_2$CF$_2$CH$_2$—, CH$_3$CF$_2$—, CH$_3$CH$_2$—, CH$_3$CF$_2$CH$_2$—, CH$_3$CF$_2$CF$_2$—, CH$_3$CH$_2$CH$_2$—, CH$_3$CF$_2$CH$_2$CF$_2$—, CH$_3$CF$_2$CF$_2$CF$_2$—, CH$_3$CH$_2$CF$_2$CF$_2$—, CH$_3$CH$_2$CH$_2$CH$_2$—, CH$_3$CF$_2$CH$_2$CF$_2$CH$_2$—, CH$_3$CF$_2$CF$_2$CF$_2$CH$_2$—, CH$_3$CF$_2$CF$_2$CH$_2$CH$_2$—, CH$_3$CH$_2$CF$_2$CF$_2$CH$_2$—, CH$_3$CF$_2$CF$_2$CH$_2$CH$_2$—, CH$_3$CH$_2$CF$_2$CF$_2$CH$_2$CH$_2$—, and CH$_3$CF$_2$CH$_2$CF$_2$CH$_2$CH$_2$—.

When n2 is 1, those represented by the following formulae:

[Chem. 39]

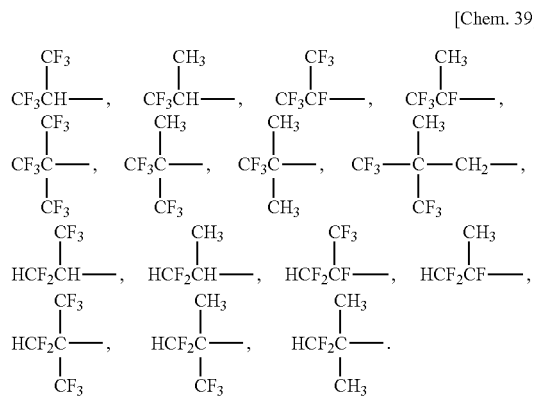

may be mentioned as examples of R$^3$ which is a branched group.

The presence of a branch such as CH$_3$— or CF$_3$— may easily cause high viscosity. Thus, R$^3$ is more preferably a linear group.

(2) In —(OR$^4$)$_{n1}$— of the formula (b-1), n1 is an integer of 1 to 3, preferably 1 or 2. When n1 is 2 or 3, R$^4$s may be the same as or different from each other.

Preferred specific examples of R$^4$ include the following linear or branched groups.

Examples of the linear groups include —CH$_2$—, —CHF—, —CF$_2$—, —CH$_2$CH$_2$—, —CF$_2$CH$_2$—, —CF$_2$CF$_2$—, —CH$_2$CF$_2$—, —CH$_2$CH$_2$CH$_2$—, —CH$_2$CH$_2$CF$_2$—, —CH$_2$CF$_2$CH$_2$—, —CH$_2$CF$_2$CF$_2$—, —CF$_2$CH$_2$CH$_2$—, —CF$_2$CF$_2$CH$_2$—, —CF$_2$CH$_2$CF$_2$—, and —CF$_2$CF$_2$CF$_2$—.

Those represented by the following formulae:

[Chem. 40]

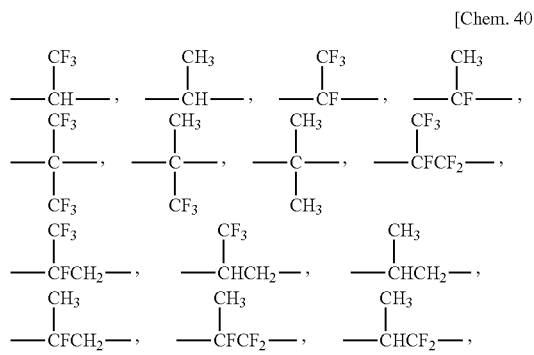

-continued

may be mentioned as examples of the branched groups.

The fluorinated alkoxy group (c) is a group obtainable by replacing at least one hydrogen atom of an alkoxy group by a fluorine atom. The fluorinated alkoxy group (c) preferably has a carbon number of 1 to 17, more preferably 1 to 6.

The fluorinated alkoxy group (c) is particularly preferably a fluorinated alkoxy group represented by X$^d_3$C—(R$^6$)$_{n3}$—O—, wherein three X$^d$s are the same as or different from each other, and are each H or F; R$^6$ is preferably a C1-C5 alkylene group optionally containing a fluorine atom; n3 is 0 or 1; and any of the three X$^d$s contain a fluorine atom.

Specific examples of the fluorinated alkoxy group (c) include fluorinated alkoxy groups in which an oxygen atom binds to an end of an alkyl group mentioned as an example for R$^1$ in the formula (a-1).

The fluorinated alkyl group (a), the fluorinated alkyl group (b) containing an ether bond, and the fluorinated alkoxy group (c) in the fluorinated saturated cyclic carbonate each preferably have a fluorine content of 10% by mass or more. Too less a fluorine content may cause a failure in sufficiently achieving an effect of reducing the viscosity at low temperature and an effect of increasing the flash point. Thus, the fluorine content is more preferably 12% by mass or more, still more preferably 15% by mass or more. The upper limit thereof is usually 76% by mass.

The fluorine content of each of the fluorinated alkyl group (a), the fluorinated alkyl group (b) containing an ether bond, and the fluorinated alkoxy group (c) is a value calculated based on the corresponding structural formula by the following formula:

{(Number of fluorine atoms×19)/(Formula weight of group)}×100(%).

In order to give good permittivity and oxidation resistance, the fluorine content in the whole fluorinated saturated cyclic carbonate is preferably 10% by mass or more, more preferably 15% by mass or more. The upper limit thereof is usually 76% by mass.

The fluorine content in the fluorinated saturated cyclic carbonate is a value calculated based on the structural formula of the fluorinated saturated cyclic carbonate by the following formula:

{(Number of fluorine atoms×19)/(Molecular weight of fluorinated saturated cyclic carbonate)}×100 (%).

Specific examples of the fluorinated saturated cyclic carbonate include the following.

Specific examples of the fluorinated saturated cyclic carbonate in which at least one selected from X$^1$ to X$^4$ is —F include those represented by the following formulae.

[Chem. 41]

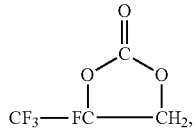 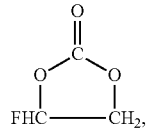

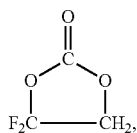 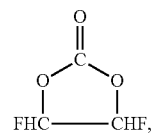

These compounds have a high withstand voltage and give good solubility of an electrolyte salt.

Alternatively, those represented by the following formulae:

[Chem. 42]

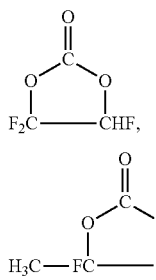 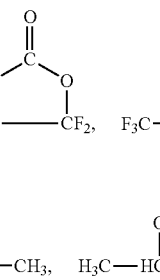

may also be used.

Those represented by the following formulae:

[Chem. 43]

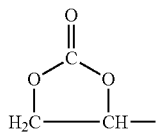 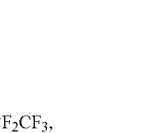
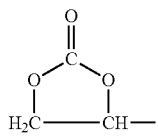 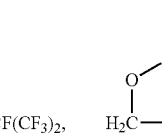
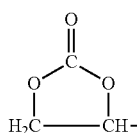 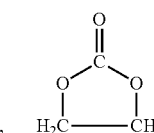
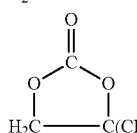 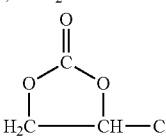
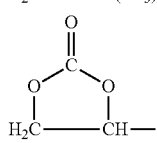

[Chem. 44]

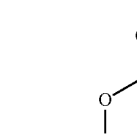 

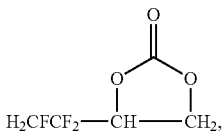 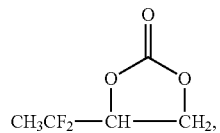
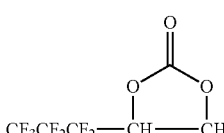 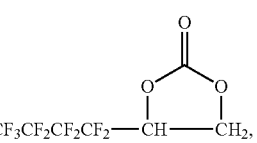
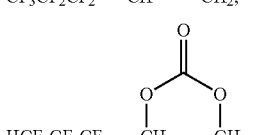
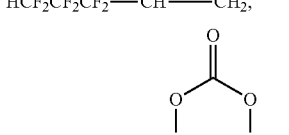

[Chem. 45]

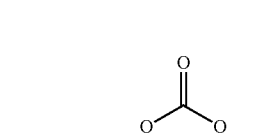 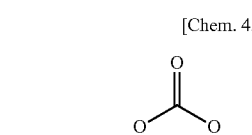

may be mentioned as specific examples of the fluorinated saturated cyclic carbonate in which at least one selected from $X^1$ to $X^4$ is a fluorinated alkyl group (a) and the others are —H.

Those represented by the following formulae:

[Chem. 46]

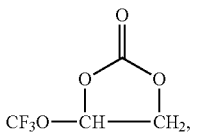 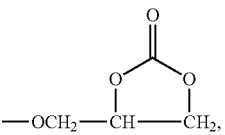
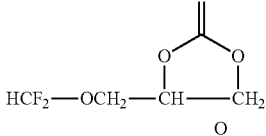
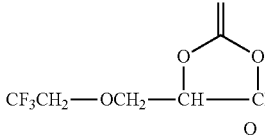
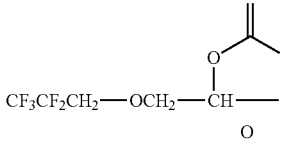
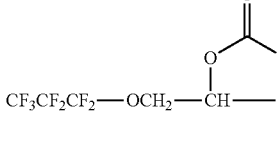

CF3(CF3)CH—OCH2—CH(—O—C(=O)—O—)—CH2, (CF3)3C—OCH2—CH(—O—C(=O)—O—)—CH2,

CH3(CF3)2CCH2—OCH2—CH(—O—C(=O)—O—)—CH2,

FCH2CF2CF3—OCH2—CH(—O—C(=O)—O—)—CH2,

FCH2CF2CH2—OCH2—CH(—O—C(=O)—O—)—CH2,

CF3CH2CH2—OCH2—CH(—O—C(=O)—O—)—CH2,

CF3CF2CH2CH2—OCH2—CH(—O—C(=O)—O—)—CH2,

CH3CF2CH2CH2—OCH2—CH(—O—C(=O)—O—)—CH2,

HCF2CF2CH2—OCH2—CH(—O—C(=O)—O—)—CH2,

CF3CF2CF2CH2CH2—OCH2—CH(—O—C(=O)—O—)—CH2,

HCF2CF2CF2CF2CH2—OCH2—CH(—O—C(=O)—O—)—CH2,

CF3CF2CF2—OCFCH2(CF3)—OCH2—CH(—O—C(=O)—O—)—CH2,

[Chem. 47]

CF3CF2CF2—OCFCF2(CF3)—OCH2—CH(—O—C(=O)—O—)—CH2,

CH3—OCFCH2(CF3)—OCH2—CH(—O—C(=O)—O—)—CH2,

CF3CF2CF2—OCFCF2(CF3)—OCFCH2(CF3)—OCH2—CH(—O—C(=O)—O—)—CH2,

FCH2CF2CF2—OCH2CF2CF2—OCH2—CH(—O—C(=O)—O—)—CH2,

FCH2CF2CF2—OCH2CF2CH2—OCH2—CH(—O—C(=O)—O—)—CH2,

[Chem. 48]

HCF2CF2CH2—OCFCF2(CF3)—OCH2—CH(—O—C(=O)—O—)—CH2,

HCF2CF2CH2—OCFCF2(CF3)—OCH2—CH(—O—C(=O)—O—)—CH2,

CF3CH(CF3)—OCFCF2(CF3)—OCH2—CH(—O—C(=O)—O—)—CH2,

CF3CH(CF3)—OCFCF2(CF3)—OCH2—CH(—O—C(=O)—O—)—CH2,

CF3CF2CF2—OCFCH2(CF3)—CH(—O—C(=O)—O—)—CH2,

CF3CF2CF2—OCFCF2(CF3)—OCFCH2(CF3)—CH(—O—C(=O)—O—)—CH2,

[Chem. 49]

FCH2CF2CF2—OCH2CF2CH2—CH(—O—C(=O)—O—)—CH2,

[Chem. 50]
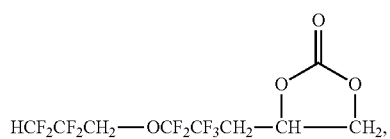
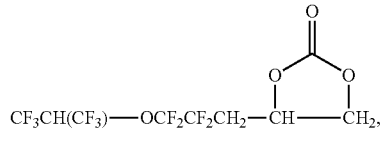
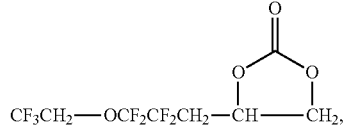
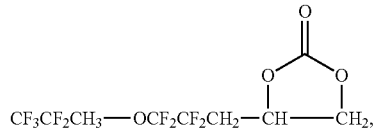
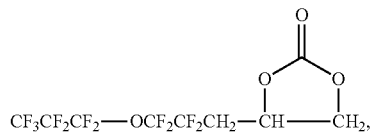
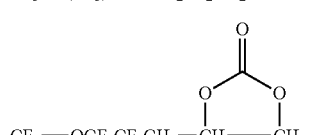
[Chem. 51]
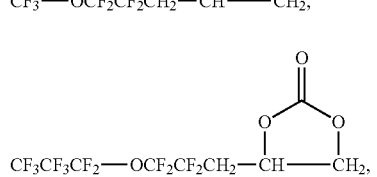
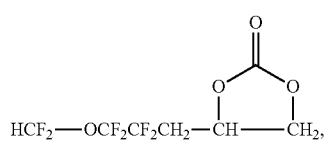
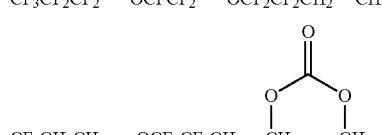
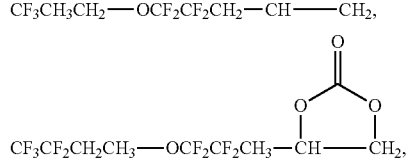
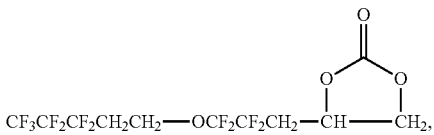
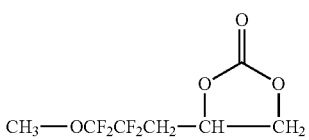
may be mentioned as specific examples of the fluorinated saturated cyclic carbonate in which at least one selected from $X^1$ to $X^4$ is a fluorinated alkyl group (b) containing an ether bond or a fluorinated alkoxy group (c) and the others are —H.
In particular, the fluorinated saturated cyclic carbonate is preferably any of the following compounds.
[Chem. 52]
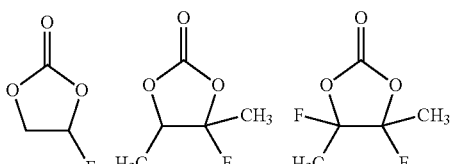
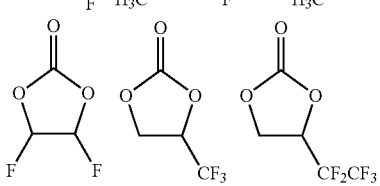
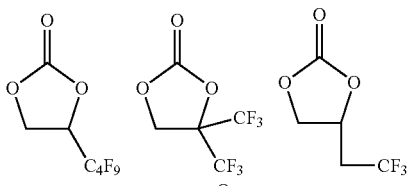
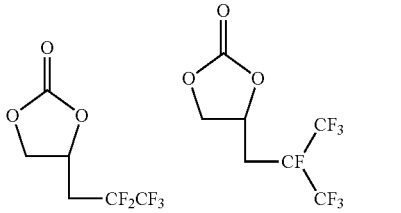
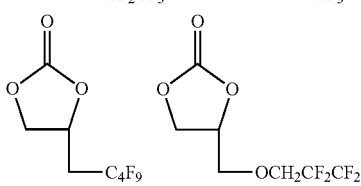
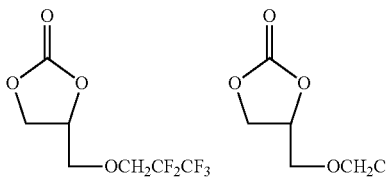

[Chem. 53]
-continued

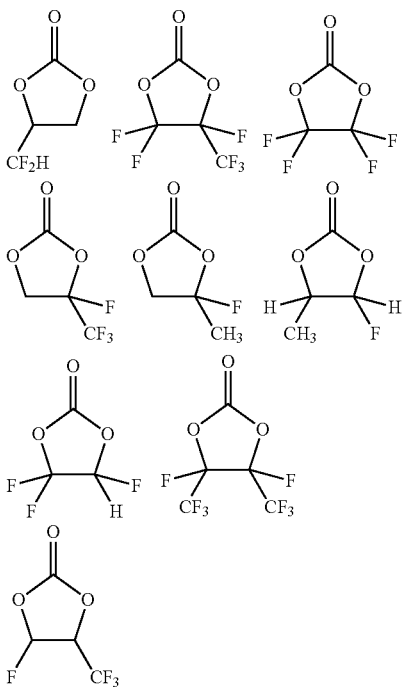

Examples of the fluorinated saturated cyclic carbonate also include trans-4,5-difluoro-1,3-dioxolan-2-one, 5-(1,1-difluoroethyl)-4,4-difluoro-1,3-dioxolan-2-one, 4-methylene-1,3-dioxolan-2-one, 4-methyl-5-trifluoromethyl-1,3-dioxolan-2-one, 4-ethyl-5-fluoro-1,3-dioxolan-2-one, 4-ethyl-5,5-difluoro-1,3-dioxolan-2-one, 4-ethyl-4,5-difluoro-1,3-dioxolan-2-one, 4-ethyl-4,5,5-trifluoro-1,3-dioxolan-2-one, 4,4-difluoro-5-methyl-1,3-dioxolan-2-one, 4-fluoro-5-methyl-1,3-dioxolan-2-one, 4-fluoro-5-trifluoromethyl-1,3-dioxolan-2-one, and 4,4-difluoro-1,3-dioxolan-2-one.

More preferred among these as the fluorinated saturated cyclic carbonate are fluoroethylene carbonate, difluoroethylene carbonate, trifluoromethylethylene carbonate, (3,3,3-trifluoropropylene carbonate), and 2,2,3,3,3-pentafluoropropylethylene carbonate.

The fluorinated unsaturated cyclic carbonate is a cyclic carbonate containing an unsaturated bond and a fluorine atom, and is preferably a fluorinated ethylene carbonate derivative substituted with a substituent containing an aromatic ring or a carbon-carbon double bond. Specific examples thereof include 4,4-difluoro-5-phenyl ethylene carbonate, 4,5-difluoro-4-phenyl ethylene carbonate, 4-fluoro-5-phenyl ethylene carbonate, 4-fluoro-5-vinyl ethylene carbonate, 4-fluoro-4-phenyl ethylene carbonate, 4,4-difluoro-4-vinyl ethylene carbonate, 4,4-difluoro-4-allyl ethylene carbonate, 4-fluoro-4-vinyl ethylene carbonate, 4-fluoro-4,5-diallyl ethylene carbonate, 4,5-difluoro-4-vinyl ethylene carbonate, 4,5-difluoro-4,5-divinyl ethylene carbonate, and 4,5-difluoro-4,5-diallyl ethylene carbonate.

One fluorinated cyclic carbonate may be used alone or two or more thereof may be used in any combination at any ratio.

The fluorinated cyclic carbonate, when contained, is preferably present in an amount of 5 to 90% by volume, more preferably 10 to 60% by volume, still more preferably 15 to 45% by volume, relative to the solvent.

The acyclic carbonate may be either a non-fluorinated acyclic carbonate or a fluorinated acyclic carbonate.

Examples of the non-fluorinated acyclic carbonate include hydrocarbon-based acyclic carbonates such as $CH_3OCOOCH_3$ (dimethyl carbonate, DMC), $CH_3CH_2OCOOCH_2CH_3$ (diethyl carbonate, DEC), $CH_3CH_2OCOOCH_3$ (ethyl methyl carbonate, EMC), $CH_3OCOOCH_2CH_2CH_3$ (methyl propyl carbonate), methyl butyl carbonate, ethyl propyl carbonate, ethyl butyl carbonate, dipropyl carbonate, dibutyl carbonate, methyl isopropyl carbonate, methyl-2-phenyl phenyl carbonate, phenyl-2-phenyl phenyl carbonate, trans-2,3-pentylene carbonate, trans-2,3-butylene carbonate, and ethyl phenyl carbonate. Preferred among these is at least one selected from the group consisting of ethyl methyl carbonate, diethyl carbonate, and dimethyl carbonate.

One non-fluorinated acyclic carbonate may be used alone or two or more thereof may be used in any combination at any ratio.

The non-fluorinated acyclic carbonate, when contained, is preferably present in an amount of 10 to 90% by volume, more preferably 40 to 85% by volume, still more preferably 50 to 80% by volume, relative to the solvent.

The fluorinated acyclic carbonate is an acyclic carbonate containing a fluorine atom. A solvent containing a fluorinated acyclic carbonate can suitably be used at high voltage.

An example of the fluorinated acyclic carbonate is a compound represented by the following formula (B):

$$Rf^2OCOOR^7 \quad (B)$$

wherein $Rf^2$ is a C1-C7 fluorinated alkyl group; and $R^7$ is a C1-C7 alkyl group optionally containing a fluorine atom.

$Rf^2$ is a C1-C7 fluorinated alkyl group and $R^7$ is a C1-C7 alkyl group optionally containing a fluorine atom.

The fluorinated alkyl group is a group obtainable by replacing at least one hydrogen atom of an alkyl group by a fluorine atom. When $R^7$ is an alkyl group containing a fluorine atom, it is a fluorinated alkyl group.

In order to give low viscosity, $Rf^2$ and $R^7$ each preferably have a carbon number of 1 to 7, more preferably 1 to 2.

Too large a carbon number may cause poor low-temperature characteristics and low solubility of an electrolyte salt. Too small a carbon number may cause low solubility of an electrolyte salt, low discharge efficiency, and increased viscosity, for example.

Examples of the fluorinated alkyl group having a carbon number of 1 include $CFH_2$—, $CF_2H$—, and $CF_3$—. In order to give high-temperature storage characteristics, particularly preferred is $CFH_2$— or $CF_3$—.

In order to give good solubility of an electrolyte salt, preferred examples of the fluorinated alkyl group having a carbon number of 2 or greater include fluorinated alkyl groups represented by the following formula (d-1):

$$R^1\text{-}R^2\text{—} \quad (d\text{-}1)$$

wherein $R^1$ is an alkyl group having a carbon number of 1 or greater and optionally containing a fluorine atom; $R^2$ is a C1-C3 alkylene group optionally containing a fluorine atom; and at least one selected from $R^1$ and $R^2$ contains a fluorine atom.

$R^1$ and $R^2$ each may further contain an atom other than carbon, hydrogen, and fluorine atoms.

$R^1$ is an alkyl group having a carbon number of 1 or greater and optionally containing a fluorine atom. $R^1$ is preferably a C1-C6 linear or branched alkyl group. The carbon number of $R^1$ is more preferably 1 to 3.

Specifically, for example, $CH_3$—, $CF_3$—, $CH_3CH_2$—, $CH_3CH_2CH_2$—, $CH_3CH_2CH_2CH_2$—, and groups represented by the following formulae:

[Chem. 54]

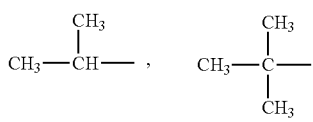

may be mentioned as linear or branched alkyl groups for $R^1$.

Examples of $R^1$ which is a linear alkyl group containing a fluorine atom include $CF_3-$, $CF_3CH_2-$, $CF_3CF_2-$, $CF_3CH_2CH_2-$, $CF_3CF_2CH_2-$, $CF_3CF_2CF_2-$, $CF_3CH_2CF_2-$, $CF_3CH_2CH_2CH_2-$, $CF_3CF_2CH_2CH_2-$, $CF_3CH_2CF_2CH_2-$, $CF_3CF_2CF_2CH_2-$, $CF_3CF_2CF_2CF_2-$, $CF_3CF_2CH_2CF_2-$, $CF_3CH_2CH_2CH_2CH_2-$, $CF_3CF_2CH_2CH_2CH_2-$, $CF_3CH_2CF_2CH_2CH_2-$, $CF_3CF_2CF_2CH_2CH_2-$, $CF_3CF_2CF_2CF_2CH_2-$, $CF_3CF_2CH_2CH_2CH_2CH_2-$, $CF_3CF_2CH_2CF_2CH_2CH_2-$, $HCF_2-$, $HCF_2CH_2-$, $HCF_2CF_2-$, $HCF_2CH_2CH_2-$, $HCF_2CF_2CH_2-$, $HCF_2CH_2CF_2-$, $HCF_2CF_2CH_2CH_2-$, $HCF_2CH_2CF_2CH_2-$, $HCF_2CF_2CF_2CF_2-$, $HCF_2CF_2CH_2CH_2CH_2-$, $HCF_2CH_2CF_2CH_2CH_2-$, $HCF_2CF_2CF_2CF_2CH_2-$, $HCF_2CF_2CF_2CF_2CH_2CH_2-$, $FCH_2-$, $FCH_2CH_2-$, $FCH_2CF_2-$, $FCH_2CF_2CH_2-$, $FCH_2CF_2CF_2-$, $CH_3CF_2CH_2-$, $CH_3CF_2CF_2-$, $CH_3CF_2CH_2CF_2-$, $CH_3CF_2CF_2CF_2-$, $CH_3CH_2CF_2CF_2-$, $CH_3CF_2CH_2CF_2CH_2-$, $CH_3CF_2CF_2CF_2CH_2-$, $CH_3CF_2CF_2CH_2CH_2-$, $CH_3CH_2CF_2CF_2CH_2-$, $CH_3CF_2CH_2CF_2CH_2CH_2-$, $CH_3CF_2CH_2CF_2CH_2CH_2-$, $HCFClCF_2CH_2-$, $HCF_2CFClCH_2-$, $HCF_2CFClCF_2CFClCH_2-$, and $HCFClCF_2CFClCF_2CH_2-$.

Examples of $R^1$ which is a branched alkyl group containing a fluorine atom include those represented by the following formulae:

[Chem. 55]

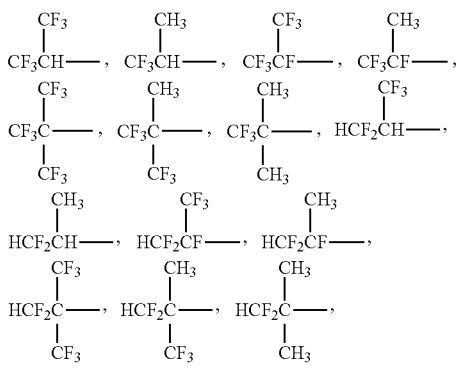

[Chem. 56]

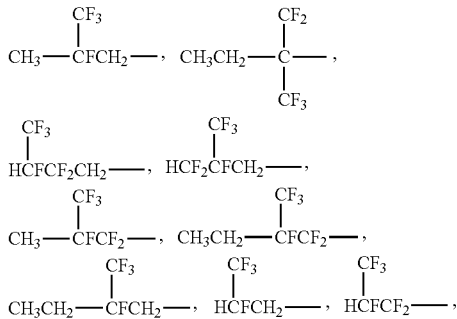

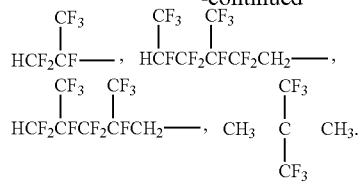

The presence of a branch such as $CH_3-$ or $CF_3-$ may easily cause high viscosity. Thus, the number of such branches is more preferably small (one) or zero.

$R^2$ is a C1-C3 alkylene group optionally containing a fluorine atom. $R^2$ may be either linear or branched. Examples of a minimum structural unit constituting such a linear or branched alkylene group are shown below. $R^2$ is constituted by one or combination of these units.

(i) Linear Minimum Structural Units
$-CH_2-$, $-CHF-$, $-CF_2-$, $-CHCl-$, $-CFCl-$, $-CCl_2-$ (ii) Branched Minimum Structural Units

[Chem. 57]

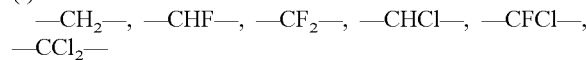

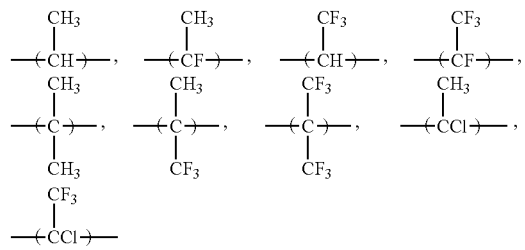

Preferred among these exemplified units are Cl-free structural units because such units may not be dehydrochlorinated by a base, and thus may be more stable.

$R^2$ which is a linear group consists only of any of the above linear minimum structural units, and is preferably $-CH_2-$, $-CH_2CH_2-$, or $-CF_2-$. In order to further improve the solubility of an electrolyte salt, $-CH_2-$ or $-CH_2CH_2-$ is more preferred.

$R^2$ which is a branched group includes at least one of the above branched minimum structural units. A preferred example thereof is a group represented by $-(CX^aX^b)-$ (wherein $X^a$ is H, F, $CH_3$, or $CF_3$; $X^b$ is $CH_3$ or $CF_3$; when $X^b$ is $CF_3$, $X^a$ is H or $CH_3$). Such a group can much further improve the solubility of an electrolyte salt.

For example, $CF_3CF_2-$, $HCF_2CF_2-$, $H_2CFCF_2-$, $CH_3CF_2-$, $CF_3CH_2-$, $CF_3CF_2CF_2-$, $HCF_2CF_2CF_2-$, $H_2CFCF_2CF_2-$, $CH_3CF_2CF_2-$, and those represented by the following formulae:

[Chem. 58]

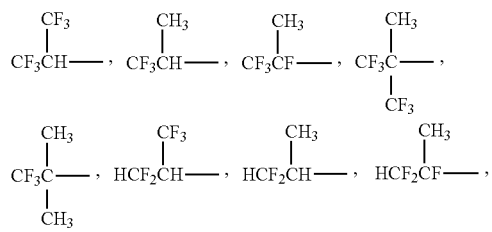

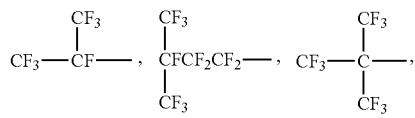

[Chem. 59]

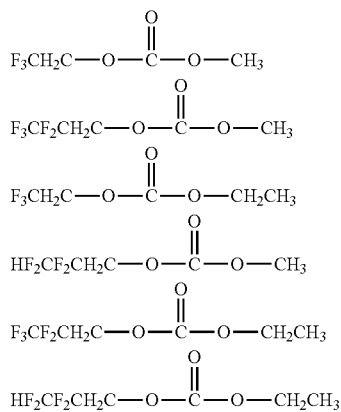

may be specifically mentioned as preferred examples of the fluorinated alkyl group.

The fluorinated alkyl group for $Rf^2$ and $R^7$ is preferably $CF_3-$, $CF_3CF_2-$, $(CF_3)_2CH-$, $CF_3CH_2-$, $C_2F_5CH_2-$, $CF_3CF_2CH_2-$, $HCF_2CF_2CH_2-$, $CF_3CFHCF_2CH_2-$, $CFH_2-$, and $CF_2H-$. In order to give high incombustibility and good rate characteristics and oxidation resistance, more preferred are $CF_3CH_2-$, $CF_3CF_2CH_2-$, $HCF_2CF_2CH_2-$, $CFH_2-$, and $CF_2H-$.

$R^7$, when it is an alkyl group free from a fluorine atom, is a C1-C7 alkyl group. In order to give low viscosity, $R^7$ preferably has a carbon number of 1 to 4, more preferably 1 to 3.

Examples of the alkyl group free from a fluorine atom include $CH_3-$, $CH_3CH_2-$, $(CH_3)_2CH-$, and $C_3H_7-$. In order to give low viscosity and good rate characteristics, preferred are $CH_3-$ and $CH_3CH_2-$.

The fluorinated acyclic carbonate preferably has a fluorine content of 15 to 70% by mass. The fluorinated acyclic carbonate having a fluorine content within the above range can maintain the miscibility with a solvent and the solubility of a salt. The fluorine content is more preferably 20% by mass or more, still more preferably 30% by mass or more, particularly preferably 35% by mass or more, while more preferably 60% by mass or less, still more preferably 50% by mass or less.

In the invention, the fluorine content is a value calculated based on the structural formula of the fluorinated acyclic carbonate by the following formula:

{(Number of fluorine atoms×19)/(Molecular weight of fluorinated acyclic carbonate)}×100(%).

In order to give low viscosity, the fluorinated acyclic carbonate is preferably any of the following compounds.

[Chem. 60]

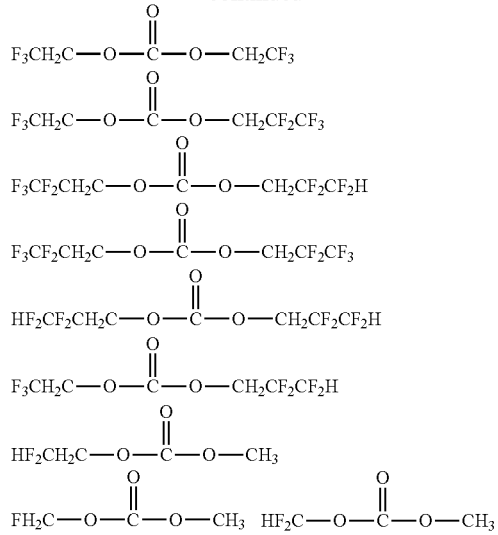

The fluorinated acyclic carbonate is particularly preferably methyl 2,2,2-trifluoroethyl carbonate.

One fluorinated acyclic carbonate may be used alone, or two or more thereof may be used in any combination at any ratio.

The fluorinated acyclic carbonate, when contained, is preferably present in an amount of 10 to 90% by volume, more preferably 40 to 85% by volume, still more preferably 50 to 80% by volume, relative to the solvent.

The carboxylate may be either a cyclic carboxylate or an acyclic carboxylate.

The cyclic carboxylate may be either a non-fluorinated cyclic carboxylate or a fluorinated cyclic carboxylate.

Examples of the non-fluorinated cyclic carboxylate include a non-fluorinated saturated cyclic carboxylate, and preferred is a non-fluorinated saturated cyclic carboxylate containing a C2-C4 alkylene group.

Specific examples of the non-fluorinated saturated cyclic carboxylate containing a C2-C4 alkylene group include β-propiolactone, γ-butyrolactone, ε-caprolactone, 5-valerolactone, and α-methyl-γ-butyrolactone. In order to improve the degree of dissociation of lithium ions and to improve the load characteristics, particularly preferred among these are γ-butyrolactone and δ-valerolactone.

One non-fluorinated saturated cyclic carboxylate may be used alone or two or more thereof may be used in any combination at any ratio.

The non-fluorinated saturated cyclic carboxylate, when contained, is preferably present in an amount of 0 to 90% by volume, more preferably 0.001 to 90% by volume, still more preferably 1 to 60% by volume, particularly preferably 5 to 40% by volume, relative to the solvent.

The acyclic carboxylate may be either a non-fluorinated acyclic carboxylate or a fluorinated acyclic carboxylate.

Examples of the non-fluorinated acyclic carboxylate include methyl acetate, ethyl acetate, propyl acetate, butyl acetate, methyl propionate, ethyl propionate, propyl propionate, butyl propionate, tert-butyl propionate, tert-butyl butyrate, sec-butyl propionate, sec-butyl butyrate, n-butyl butyrate, methyl pyrophosphate, ethyl pyrophosphate, tert-butyl formate, tert-butyl acetate, sec-butyl formate, sec-butyl acetate, n-hexyl pivalate, n-propyl formate, n-propyl acetate, n-butyl formate, n-butyl pivalate, n-octyl pivalate, ethyl 2-(dimethoxyphosphoryl)acetate, ethyl 2-(dimethylphosphoryl)acetate, ethyl 2-(diethoxyphosphoryl)acetate, ethyl 2-(diethylphosphoryl)acetate, isopropyl propionate, isopropyl acetate, ethyl formate, ethyl 2-propynyl oxalate, isopropyl formate, isopropyl butyrate, isobutyl formate, isobutyl propionate, isobutyl butyrate, and isobutyl acetate.

Preferred among these are butyl acetate, methyl propionate, ethyl propionate, propyl propionate, and butyl propionate, particularly preferred are ethyl propionate and propyl propionate.

One non-fluorinated acyclic carboxylate may be used alone or two or more thereof may be used in any combination at any ratio.

The non-fluorinated acyclic carboxylate, when contained, is preferably present in an amount of 0 to 90% by volume, more preferably 0.001 to 90% by volume, still more preferably 1 to 60% by volume, particularly preferably 5 to 40% by volume, relative to the solvent.

The non-fluorinated acyclic ester is preferably present in an amount of 0 to 90% by volume, more preferably 0.001 to 90% by volume, still more preferably 1 to 60% by volume, particularly preferably 5 to 40% by volume, relative to the solvent.

The fluorinated acyclic carboxylate is an acyclic carboxylate containing a fluorine atom. A solvent containing a fluorinated acyclic carboxylate can be suitably used at high voltage.

In order to achieve good miscibility with other solvents and to give good oxidation resistance, preferred examples of the fluorinated acyclic carboxylate include a fluorinated acyclic carboxylate represented by the following formula:

$$Rf^{31}COORf^{32}$$

(wherein $Rf^{31}$ is a C1-C4 fluorinated alkyl group; and $Rf^{32}$ is a C1-C4 alkyl group optionally containing a fluorine atom).

Examples of $Rf^{31}$ include $HCF_2-$, $CF_3-$, $CF_3CF_2-$, $HCF_2CF_2-$, $CH_3CF_2-$, and $CF_3CH_2-$. In order to achieve good viscosity and oxidation resistance, particularly preferred among these are $HCF_2-$, $CF_3-$, $CF_3CF_2-$, and $CF_3CH_2-$.

Examples of $Rf^{32}$ include $CH_3-$, $C_2H_5-$, $CF_3-$, $CF_3CF_2-$, $(CF_3)_2CH-$, $CF_3CH_2-$, $CF_3CH_2CH_2-$, $CF_3CFHCF_2CH_2-$, $C_2F_5CH_2-$, $CF_2HCF_2CH_2-$, $C_2F_5CH_2CH_2-$, $CF_3CF_2CH_2-$, and $CF_3CF_2CF_2CH_2-$. In order to achieve good miscibility with other solvents, particularly preferred among these are $CH_3-$, $C_2H_5-$, $CF_3CH_2-$, and $CF_3OCH_2OCH_2-$.

Specific examples of the fluorinated acyclic carboxylate include one or two or more of $CF_3CH_2C(=O)$ $OCH_3$ (methyl 3,3,3-trifluoropropionate), $HCF_2C(=O)OCH_3$ (methyl difluoroacetate), $HCF_2C(=O)OC_2H_5$ (ethyl difluoroacetate), $CF_3C(=O)$ $OCH_2CH_2CF_3$, $CF_3C(=O)$ $OCH_2C_2F_5$, $CF_3C(=O)$ $OCH_2CF_2CF_2H$ (2,2,3,3-tetrafluoropropyl trifluoroacetate), $CF_3C(=O)$ $OCH_2CF_3$, $CF_3C(=O)$ $OCH(CF_3)_2$, ethyl pentafluorobutyrate, methyl pentafluoropropionate, ethyl pentafluoropropionate, methyl pentafluoroisobutyrate, isopropyl trifluorobutyrate, ethyl trifluoroacetate, tert-butyl trifluoroacetate, n-butyl trifluoroacetate, methyl tetrafluoro-2-(methoxy)propionate, 2,2-difluoroethyl acetate, 2,2,3,3-tetrafluoropropyl acetate, 2,2,2-trifluoroethyl acetate, 1H,1H-heptafluorobutyl acetate, methyl 4,4,4-trifluorobutyrate, ethyl 4,4,4-trifluorobutyrate, ethyl 3,3,3-trifluoropropionate, 3,3,3trifluoropropyl 3,3,3-trifluoropropionate, ethyl 3-(trifluoromethyl)butyrate, methyl 2,3,3,3-tetrafluoropropionate, butyl 2,2-difluoroacetate, methyl 2,2,3,3-tetrafluoropropionate, methyl 2-(trifluoromethyl)-3,3,3-trifluoropropionate, and methyl heptafluorobutyrate.

In order to achieve good miscibility with other solvents and good rate characteristics, preferred among these are $CF_3CH_2C(=O)$ $OCH_3$, $HCF_2C(=O)$ $OCH_3$, $HCF_2C(=O)$ $OC_2H_5$, $CF_3C(=O)$ $OCH_2C_2F_5$, $CF_3C(=O)$ $OCH_2CF_2CF_2H$, $CF_3C(=O)$ $OCH_2CF_3$, $CF_3C(=O)$ $OCH(CF_3)_2$, ethyl pentafluorobutyrate, methyl pentafluoropropionate, ethyl pentafluoropropionate, methyl pentafluoroisobutyrate, isopropyl trifluorobutyrate, ethyl trifluoroacetate, tert-butyl trifluoroacetate, n-butyl trifluoroacetate, methyl tetrafluoro-2-(methoxy)propionate, 2,2-difluoroethyl acetate, 2,2,3,3-tetrafluoropropyl acetate, 2,2,2-trifluoroethyl acetate, 1H,1H-heptafluorobutyl acetate, methyl 4,4,4-trifluorobutyrate, ethyl 4,4,4-trifluorobutyrate, ethyl 3,3,3-trifluoropropionate, 3,3,3-trifluoropropyl 3,3,3-trifluoropropionate, ethyl 3-(trifluoromethyl)butyrate, methyl 2,3,3,3-tetrafluoropropionate, butyl 2,2-difluoroacetate, methyl 2,2,3,3,-tetrafluoropropionate, methyl 2-(trifluoromethyl)-3,3,3-trifluoropropionate, and methyl heptafluorobutyrate, more preferred are $CF_3CH_2C(=O)OCH_3$, $HCF_2C(=O)OCH_3$, and $HCF_2C(=O)OC_2H_5$, and particularly preferred are $HCF_2C(=O)OCH_3$ and $HCF_2C(=O)OC_2H_5$.

One fluorinated acyclic carboxylate may be used alone or two or more thereof may be used in any combination at any ratio.

The fluorinated acyclic carboxylate, when contained, is preferably present in an amount of 10 to 90% by volume, more preferably 40 to 85% by volume, still more preferably 50 to 80% by volume, relative to the solvent.

The solvent preferably contains at least one selected from the group consisting of the cyclic carbonate, the acyclic carbonate, and the acyclic carboxylate, and more preferably contains the cyclic carbonate and at least one selected from the group consisting of the acyclic carbonate and the acyclic carboxylate. The cyclic carbonate is preferably a saturated cyclic carbonate.

An electrolyte solution containing a solvent of such a composition enables an electrochemical device to have further improved high-temperature storage characteristics and cycle characteristics.

For the solvent containing the cyclic carbonate and at least one selected from the group consisting of the acyclic carbonate and the acyclic carboxylate, the total amount of the cyclic carbonate and at least one selected from the group consisting of the acyclic carbonate and the acyclic carboxylate ester is preferably 10 to 100% by volume, more preferably 30 to 100% by volume, still more preferably 50 to 100% by volume.

For the solvent containing the cyclic carbonate and at least one selected from the group consisting of the acyclic carbonate and the acyclic carboxylate, the cyclic carbonate and at least one selected from the group consisting of the acyclic carbonate and the acyclic carboxylate preferably give a volume ratio of 5/95 to 95/5, more preferably 10/90 or more, still more preferably 15/85 or more, particularly preferably 20/80 or more, while more preferably 90/10 or less, still more preferably 60/40 or less, particularly preferably 50/50 or less.

The solvent also preferably contains at least one selected from the group consisting of the non-fluorinated saturated cyclic carbonate, the non-fluorinated acyclic carbonate, and the non-fluorinated acyclic carboxylate, more preferably contains the non-fluorinated saturated cyclic carbonate and at least one selected from the group consisting of the non-fluorinated acyclic carbonate and the non-fluorinated acyclic carboxylate. An electrolyte solution containing a solvent of such a composition can suitably be used for electrochemical devices used at relatively low voltage.

For the solvent containing the non-fluorinated saturated cyclic carbonate and at least one selected from the group consisting of the non-fluorinated acyclic carbonate and the non-fluorinated acyclic carboxylate, the total amount of the non-fluorinated saturated cyclic carbonate and at least one selected from the group consisting of the non-fluorinated acyclic carbonate and the non-fluorinated acyclic carboxylate ester is preferably 5 to 100% by volume, more preferably 20 to 100% by volume, still more preferably 30 to 100% by volume.

For the electrolyte solution containing the non-fluorinated saturated cyclic carbonate and at least one selected from the group consisting of the non-fluorinated acyclic carbonate and the non-fluorinated acyclic carboxylate, the non-fluorinated saturated cyclic carbonate and at least one selected from the group consisting of the non-fluorinated acyclic carbonate and the non-fluorinated acyclic carboxylate ester preferably give a volume ratio of 5/95 to 95/5, more preferably 10/90 or more, still more preferably 15/85 or more, particularly preferably 20/80 or more, while more preferably 90/10 or less, still more preferably 60/40 or less, particularly preferably 50/50 or less.

The solvent preferably contains at least one selected from the group consisting of the fluorinated saturated cyclic carbonate, the fluorinated acyclic carbonate, and the fluorinated acyclic carboxylate, and more preferably contains the fluorinated saturated cyclic carbonate and at least one selected from the group consisting of the fluorinated acyclic carbonate and the fluorinated acyclic carboxylate. An electrolyte solution containing a solvent of such a composition can suitably be used for not only electrochemical devices used at relatively high voltage but also electrochemical devices used at relatively low voltage.

For the solvent containing the fluorinated saturated cyclic carbonate and at least one selected from the group consisting of the fluorinated acyclic carbonate and the fluorinated acyclic carboxylate, the total amount of the fluorinated saturated cyclic carbonate and at least one selected from the group consisting of the fluorinated acyclic carbonate and the fluorinated acyclic carboxylate ester is preferably 5 to 100% by volume, more preferably 10 to 100% by volume, still more preferably 30 to 100% by volume.

For the solvent containing the fluorinated saturated cyclic carbonate and at least one selected from the group consisting of the fluorinated acyclic carbonate and the fluorinated acyclic carboxylate, the fluorinated saturated cyclic carbonate and at least one selected from the group consisting of the fluorinated acyclic carbonate and the fluorinated acyclic carboxylate ester preferably give a volume ratio of 5/95 to 95/5, more preferably 10/90 or more, still more preferably 15/85 or more, particularly preferably 20/80 or more, while more preferably 90/10 or less, still more preferably 60/40 or less, particularly preferably 50/50 or less.

The solvent used may be an ionic liquid. The "ionic liquid" means a liquid containing an ion that is a combination of an organic cation and an anion.

Examples of the organic cation include, but are not limited to, imidazolium ions such as dialkyl imidazolium cations and trialkyl imidazolium cations; tetraalkyl ammonium ions; alkyl pyridinium ions; dialkyl pyrrolidinium ions; and dialkyl piperidinium ions.

Examples of the anion to be used as a counterion of any of these organic cations include, but are not limited to, a $PF_6$ anion, a $PF_3(C_2F_5)_3$ anion, a $PF_3(CF_3)_3$ anion, a $BF_4$ anion, a $BF_2(CF_3)_2$ anion, a $BF_3(CF_3)$ anion, a bisoxalatoborate anion, a $P(C_2O_4)F_2$ anion, a Tf (trifluoromethanesulfonyl) anion, Nf (nonafluorobutanesulfonyl) anion, a bis(fluorosulfonyl)imide anion, a bis(trifluoromethanesulfonyl)imide anion, a bis(pentafluoroethanesulfonyl)imide anion, a dicyanoamine anion, and halide anions.

The solvent is preferably a non-aqueous solvent and the electrolyte solution of the invention is preferably a non-aqueous electrolyte solution.

The electrolyte solution of the invention may further contain a compound (5) represented by the following formula (5).

The formula (5) is as follows:

[Chem. 61]

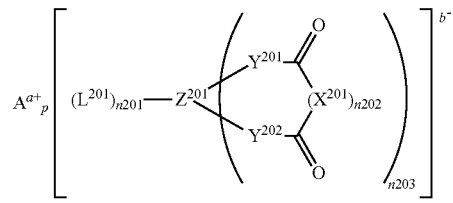

wherein
$A^{a+}$ is a metal ion, a hydrogen ion, or an onium ion;
a is an integer of 1 to 3;
b is an integer of 1 to 3;
p is b/a;
$n^{203}$ is an integer of 1 to 4;
$n^{201}$ is an integer of 0 to 8;
$n^{202}$ is 0 or 1;
$Z^{201}$ is a transition metal or an element in group III, group IV, or group V of the Periodic Table;
$X^{201}$ is O, S, a C1-C10 alkylene group, a C1-C10 halogenated alkylene group, a C6-C20 arylene group, or a C6-C20 halogenated arylene group, with the alkylene group, the halogenated alkylene group, the arylene group, and the halogenated arylene group each optionally containing a substituent and/or a hetero atom in the structure thereof, and when $n^{202}$ is 1 and $n^{203}$ is 2 to 4, $n^{203}$ $X^{201}$s optionally bind to each other;
$L^{201}$ is a halogen atom, a cyano group, a C1-C10 alkyl group, a C1-C10 halogenated alkyl group, a C6-C20 aryl group, a C6-C20 halogenated aryl group, or —$Z^{203}Y^{203}$, with the alkylene group, the halogenated alkylene group, the arylene group, and the halogenated arylene group each optionally containing a substituent and/or a hetero atom in the structure thereof, and when $n^{201}$ is 2 to 8, $n^{201}$ $L^{201}$s optionally bind to each other to form a ring;
$Y^{201}$, $Y^{202}$, and $Z^{203}$ are each individually O, S, $NY^{204}$, a hydrocarbon group, or a fluorinated hydrocarbon group;
$Y^{203}$ and $Y^{204}$ are each individually H, F, a C1-C10 alkyl group, a C1-C10 halogenated alkyl group, a C6-C20 aryl group, or a C6-C20 halogenated aryl group, with the alkyl group, the halogenated alkyl group, the aryl group, and the halogenated aryl group each optionally containing a substituent and/or a hetero atom in the structure thereof, and when multiple $Y^{203}$s or multiple $Y^{204}$s are present, they optionally bind to each other to form a ring.

Examples of $A^{a+}$ include a lithium ion, a sodium ion, a potassium ion, a magnesium ion, a calcium ion, a barium ion, a caesium ion, a silver ion, a zinc ion, a copper ion, a cobalt ion, an iron ion, a nickel ion, a manganese ion, a titanium ion, a lead ion, a chromium ion, a vanadium ion, a ruthenium ion, an yttrium ion, lanthanoid ions, actinoid ions, a tetrabutyl ammonium ion, a tetraethyl ammonium ion, a tetramethyl ammonium ion, a triethyl methyl ammonium ion, a triethyl ammonium ion, a pyridinium ion, an imidazolium ion, a hydrogen ion, a tetraethyl phosphonium ion, a tetramethyl phosphonium ion, a tetraphenyl phosphonium ion, a triphenyl sulfonium ion, and a triethyl sulfonium ion.

In applications such as electrochemical devices, $A^{a+}$ is preferably a lithium ion, a sodium ion, a magnesium ion, a tetraalkyl ammonium ion, or a hydrogen ion, particularly preferably a lithium ion. The valence a of the cation $A^{a+}$ is an integer of 1 to 3. If the valence a is greater than 3, the crystal lattice energy is high and the compound (5) has difficulty in dissolving in a solvent. Thus, the valence a is more preferably 1 when good solubility is needed. The valence b of the anion is also an integer of 1 to 3, particularly preferably 1. The constant p that represents the ratio between the cation and the anion is naturally defined by the ratio b/a between the valences thereof.

Next, ligands in the formula (5) are described. The ligands herein mean organic or inorganic groups binding to $Z^{201}$ in the formula (5).

$Z^{201}$ is preferably Al, B, V, Ti, Si, Zr, Ge, Sn, Cu, Y, Zn, Ga, Nb, Ta, Bi, P, As, Sc, Hf, or Sb, more preferably Al, B, or P.

$X^{201}$ is O, S, a C1-C10 alkylene group, a C1-C10 halogenated alkylene group, a C6-C20 arylene group, or a C6-C20 halogenated arylene group. These alkylene groups and arylene groups each may have a substituent and/or a hetero atom in the structure. Specifically, instead of a hydrogen atom in the alkylene group or the arylene group, the structure may have a halogen atom, a linear or cyclic alkyl group, an aryl group, an alkenyl group, an alkoxy group, an aryloxy group, a sulfonyl group, an amino group, a cyano group, a carbonyl group, an acyl group, an amide group, or a hydroxy group as a substituent; or, instead of a carbon atom in the alkylene or the arylene, the structure may have nitrogen, sulfur, or oxygen introduced therein. When $n^{202}$ is 1 and $n^{203}$ is 2 to 4, $n^{203}$ $X^{201}$s may bind to each other. One such example is a ligand such as ethylenediaminetetraacetic acid.

$L^{201}$ is a halogen atom, a cyano group, a C1-C10 alkyl group, a C1-C10 halogenated alkyl group, a C6-C20 aryl group, a C6-C20 halogenated aryl group, or —$Z^{203}Y^{203}$ ($Z^{203}$ and $Y_{203}$ will be described later). Similar to $X^{201}$, the alkyl groups and the aryl groups each may have a substituent and/or a hetero atom in the structure, and when $n^{201}$ is 2 to 8, $n^{201}$ $L^{201}$s optionally bind to each other to form a ring. $L^{201}$ is preferably a fluorine atom or a cyano group. This is because a fluorine atom can improve the solubility and the degree of dissociation of a salt of an anion compound, thereby improving the ion conductivity. This is also because a fluorine atom can improve the oxidation resistance, reducing occurrence of side reactions.

$Y^{201}$, $Y^{202}$, and $Z^{203}$ are each individually O, S, $NY^{204}$, a hydrocarbon group, or a fluorinated hydrocarbon group. $Y^{201}$ and $Y^{202}$ are each preferably O, S, or $NY^{204}$, more preferably O. The compound (5) characteristically has a bond between $Y^{201}$ and $Z^{201}$ and a bond between $Y^{202}$ and $Z^{201}$ in the same ligand. Such a ligand forms a chelate structure with $Z^{201}$. This chelate has an effect of improving the heat resistance, the chemical stability, and the hydrolysis resistance of this compound. The constant $n^{202}$ of the ligand is 0 or 1. In particular, $n^{22}$ is preferably 0 because the chelate ring becomes a five-membered ring, leading to the most strongly exerted chelate effect and improved stability.

The term "fluorinated hydrocarbon group" herein means a group obtainable by replacing at least one hydrogen atom of a hydrocarbon group by a fluorine atom.

$Y^{203}$ and $Y^{204}$ are each individually H, F, a C1-C10 alkyl group, a C1-C10 halogenated alkyl group, a C6-C20 aryl group, or a C6-C20 halogenated aryl group. These alkyl groups and aryl groups each may contain a substituent or a hetero atom in the structure. When multiple $Y^{203}$s or multiple $Y^{204}$s are present, they optionally bind to each other to form a ring.

The constant $n^{203}$ relating to the number of the aforementioned ligands is an integer of 1 to 4, preferably 1 or 2, more preferably 2. The constant $n^{201}$ relating to the number of the aforementioned ligands is an integer of 0 to 8, preferably an integer of 0 to 4, more preferably 0, 2, or 4. In addition, when n203 is 1, n201 is preferably 2; and when n203 is 2, n201 is preferably 0.

In the formula (5), the alkyl group, the halogenated alkyl group, the aryl group, and the halogenated aryl group include those having any other functional groups such as branches, hydroxy groups, and ether bonds.

The compound (5) is preferably a compound represented by the following formula:

[Chem. 62]

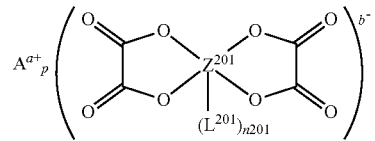

(wherein $A^{a+}$, a, b, p, $n^{201}$, $Z^{201}$, and $L^{201}$ are defined as described above), or a compound represented by the following formula:

[Chem. 63]

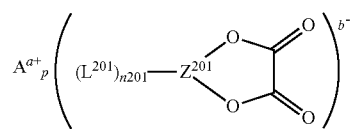

(wherein $A^{a+}$, a, b, p, $n^{201}$, $Z^{201}$, and $L^{201}$ are defined as described above).

The compound (5) may be a lithium oxalatoborate salt. Examples thereof include lithium bis(oxalato)borate (LiBOB) represented by the following formula:

[Chem. 64]

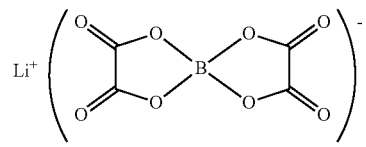

and lithium difluorooxalatoborate (LiDFOB) represented by the following formula:

[Chem. 65]

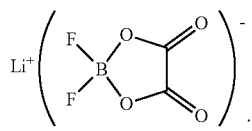

Examples of the compound (5) also include
lithium difluorooxalatophosphanite (LiDFOP) represented by the following formula:

[Chem. 66]

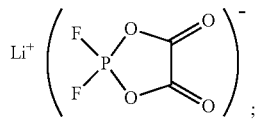

lithium tetrafluorooxalatophosphanite (LITFOP) represented by the following formula:

[Chem. 67]

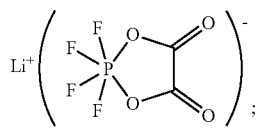

and
lithium bis(oxalato)difluorophosphanite represented by the following formula:

[Chem. 68]

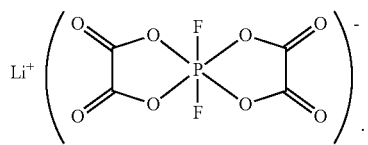

In addition, specific examples of dicarboxylic acid complex salts containing boron as a complex center element include lithium bis(malonato)borate, lithium difluoro(malonato)borate, lithium bis(methylmalonato)borate, lithium difluoro(methylmalonato)borate, lithium bis(dimethylmalonato)borate, and lithium difluoro(dimethylmalonato)borate.

Specific examples of dicarboxylic acid complex salts containing phosphorus as a complex center element include lithium tris(oxalato)phosphate, lithium tris(malonato)phosphate, lithium difluorobis(malonato)phosphate, lithium tetrafluoro(malonato)phosphate, lithium tris(methylmalonato) phosphate, lithium difluorobis(methylmalonato)phosphate, lithium tetrafluoro(methylmalonato)phosphate, lithium tris (dimethylmalonato)phosphate, lithium difluorobis(dimethylmalonato)phosphate, and lithium tetrafluoro(dimethylmalonato)phosphate.

Specific examples of dicarboxylic acid complex salts containing aluminum as a complex center element include $LiAl(C_2O_4)_2$ and $LiAlF_2(C_2O_4)$.

In order to enable easy availability and contribute to formation of a stable film-shaped structure, more preferred among these are lithium bis(oxalato)borate, lithium difluoro (oxalato)borate, lithium tris(oxalato)phosphate, lithium difluorobis(oxalato)phosphate, and lithium tetrafluoro(oxalato) phosphate. The compound (5) is particularly preferably lithium bis(oxalato)borate.

In order to give much better cycle characteristics, the compound (5) is preferably in an amount of 0.001% by mass or more, more preferably 0.01% by mass or more, while preferably 10% by mass or less, more preferably 3% by mass or less, relative to the solvent.

The electrolyte solution of the invention preferably further contains an electrolyte salt other than the compound (5). Examples of the electrolyte salt used include lithium salts, ammonium salts, and metal salts, as well as any of those to be used for electrolyte solutions such as liquid salts (ionic liquids), inorganic polymer salts, and organic polymer salts.

The electrolyte salt of the electrolyte solution for a lithium ion secondary battery is preferably a lithium salt.

Any lithium salt may be used. Specific examples thereof include the following:

inorganic lithium salts such as $LiPF_6$, $LiBF_4$, $LiClO_4$, $LiAlF_4$, $LiSbF_6$, $LiTaF_6$, $LiWF_7$, $LiAsF_6$, $LiAlCl_4$, $LiI$, $LiBr$, $LiCl$, $LiB_{10}Cl_{10}$, $Li_2SiF_6$, $Li_2PFO_3$, and $LiPO_2F_2$; lithium tungstates such as $LiWOF_5$;

lithium carboxylates such as $HCO_2Li$, $CH_3CO_2Li$, $CH_2FCO_2Li$, $CHF_2CO_2Li$, $CF_3CO_2Li$, $CF_3CH_2CO_2Li$, $CF_3CF_2CO_2Li$, $CF_3CF_2CF_2CO_2Li$, and $CF_3CF_2CF_2CF_2CO_2Li$;

lithium salts containing an S=O group such as $FSO_3Li$, $CH_3SO_3Li$, $CH_2FSO_3Li$, $CHF_2SO_3Li$, $CF_3SO_3Li$, $CF_3CF_2SO_3Li$, $CF_3CF_2CF_2SO_3Li$, $CF_3CF_2CF_2CF_2SO_3Li$, lithium methylsulfate, lithium ethylsulfate ($C_2H_5OSO_3Li$), and lithium 2,2,2-trifluoroethylsulfate;

lithium imide salts such as $LiN(FCO)_2$, $LiN(FCO)(FSO_2)$, $LiN(FSO_2)_2$, $LiN(FSO_2)(CF_3SO_2)$, $LiN(CF_3SO_2)_2$, $LiN(C_2F_5SO_2)_2$, lithium bis-perfluoroethanesulfonyl imide, lithium cyclic 1,2-perfluoroethanedisulfonyl imide, lithium cyclic 1,3-perfluoropropanedisulfonyl imide, lithium cyclic 1,2-ethanedisulfonyl imide, lithium cyclic 1,3-propanedisulfonyl imide, lithium cyclic 1,4-perfluorobutanedisulfonyl imide, $LiN(CF_3SO_2)(FSO_2)$, $LiN(CF_3SO_2)(C_3F_7SO_2)$, $LiN(CF_3SO_2)(C_4F_9SO_2)$, and $LiN(POF_2)_2$;

lithium methide salts such as $LiC(FSO_2)_3$, $LiC(CF_3SO_2)_3$, and $LiC(C_2F_5SO_2)_3$; and fluorine-containing organic lithium salts such as salts represented by the formula: $LiPF_a(C_nF_{2n}+1)_{6-a}$ (wherein a is an integer of 0 to 5; and n is an integer of 1 to 6) such as $LiPF_3(C_2F_5)_3$, $LiPF_3(CF_3)_3$, $LiPF_3(iso-C_3F_7)_3$, $LiPF_5(iso-C_3F_7)$, $LiPF_4(CF_3)_2$, and $LiPF_4(C_2F_5)_2$, as well as $LiPF_4(CF_3SO_2)_2$, $LiPF_4(C_2F_5SO_2)_2$, $LiBF_3CF_3$, $LiBF_3C_2F_5$, $LiBF_3C3F_7$, $LiBF_2(CF_3)_2$, $LiBF_2(C_2F_5)_2$, $LiBF_2(CF_3SO_2)_2$, and $LiBF_2(C_2F_5SO_2)_2$, and $LiSCN$, $LiB(CN)_4$, $LiB(C_6H_5)_4$, $Li_2(C_2O_4)$, $LiP(C_2O_4)_3$, and $Li_2B_{12}FbH_{12-b}$ (wherein b is an integer of 0 to 3).

In order to achieve an effect of improving properties such as output characteristics, high-rate charge and discharge characteristics, high-temperature storage characteristics, and cycle characteristics, particularly preferred among these are $LiPF_6$, $LiBF_4$, $LiSbF_6$, $LiTaF_6$, $LiPO_2F_2$, $FSO_3Li$, $CF_3SO_3Li$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonyl imide, lithium cyclic 1,3-perfluoropropanedisulfonyl imide, $LiC(FSO_2)_3$, $LiC(CF_3SO_2)_3$, $LiC(C_2F_5SO_2)_3$, $LiBF_3CF_3$, $LiBF_3C_2F_5$, $LiPF_3(CF_3)_3$, $LiPF_3(C_2F_5)_3$, and the like. Most preferred is at least one lithium salt selected from the group consisting of $LiPF_6$, $LiN(FSO_2)_2$, and $LiBF_4$.

These electrolyte salts may be used alone or in combination of two or more. In combination use of two or more thereof, preferred examples thereof include a combination of $LiPF_6$ and $LiBF_4$ and a combination of $LiPF_6$ and $LiPO_2F_2$, $C_2H_5OSO_3Li$, or $FSO_3Li$, each of which have an effect of improving the high-temperature storage characteristics, the load characteristics, and the cycle characteristics.

In this case, $LiBF_4$, $LiPO_2F_2$, $C_2H_5OSO_3Li$, or $FSO_3Li$ may be present in any amount that does not significantly impair the effects of the invention in 100% by mass of the whole electrolyte solution. The amount thereof is usually 0.01% by mass or more, preferably 0.1% by mass or more, while the upper limit thereof is usually 30% by mass or less, preferably 20% by mass or less, more preferably 10% by mass or less, still more preferably 5% by mass or less, relative to the electrolyte solution of the invention.

In another example, an inorganic lithium salt and an organic lithium salt are used in combination. Such a combination has an effect of reducing deterioration due to high-temperature storage. The organic lithium salt is preferably $CF_3SO_3Li$, $LiN(FSO_2)_2$, $LiN(FSO_2)(CF_3SO_2)$, $LiN(CF_3SO_2)_2$, $LiN(C_2F_5SO_2)_2$, lithium cyclic 1,2-perfluoroethanedisulfonyl imide, lithium cyclic 1,3-perfluoropropanedisulfonyl imide, $LiC(FSO_2)_3$, $LiC(CF_3SO_2)_3$, $LiC(C_2F_5SO_2)_3$, $LiBF_3CF_3$, $LiBF_3C_2F_5$, $LiPF_3(CF_3)_3$, $LiPF_3(C_2F_5)_3$, or the like. In this case, the proportion of the organic lithium salt is preferably 0.1% by mass or more, particularly preferably 0.5% by mass or more, while preferably 30% by mass or less, particularly preferably 20% by mass or less, of 100% by mass of the whole electrolyte solution.

The electrolyte salt in the electrolyte solution may have any concentration that does not impair the effects of the invention. In order to make the electric conductivity of the electrolyte solution within a favorable range and to ensure good battery performance, the lithium in the electrolyte solution preferably has a total mole concentration of 0.3 mol/L or higher, more preferably 0.4 mol/L or higher, still more preferably 0.5 mol/L or higher, while preferably 3 mol/L or lower, more preferably 2.5 mol/L or lower, still more preferably 2.0 mol/L or lower.

Too low a total mole concentration of lithium may cause insufficient electric conductivity of the electrolyte solution, while too high a concentration may cause an increase in viscosity and then reduction in electric conductivity, impairing the battery performance.

The electrolyte salt in the electrolyte solution for an electric double layer capacitor is preferably an ammonium salt.

Examples of the ammonium salt include the following salts (IIa) to (IIe).

(IIa) Tetraalkyl Quaternary Ammonium Salts

Preferred examples thereof include tetraalkyl quaternary ammonium salts represented by the following formula (IIa):

[Chem. 69]

$$R^{2a}-\underset{R^{3a}}{\overset{R^{1a}}{\underset{|}{\overset{|}{N^{\oplus}}}}}-R^{4a} \quad X^{\ominus} \tag{IIa}$$

(wherein $R^{1a}$, $R^{2a}$, $R^{3a}$, and $R^{4a}$ are the same as or different from each other, and are each a C1-C6 alkyl group optionally containing an ether bond; and $X^-$ is an anion). In order to improve the oxidation resistance, any or all of the hydrogen atoms in the ammonium salt are also preferably replaced by a fluorine atom and/or a C1-C4 fluorine-containing alkyl group.

Preferred specific examples thereof include tetraalkyl quaternary ammonium salts represented by the following formula (IIa-1):

[Chem. 70]

$$(R^{1a})_x(R^{2a})_y N^{\oplus} X^{\ominus} \tag{IIa-1}$$

(wherein $R^{1a}$, $R^{2a}$, and $X^-$ are defined as described above; x and y are the same as or different from each other, and are each an integer of 0 to 4 with x+y=4), and alkyl ether group-containing trialkyl ammonium salts represented by the following formula (IIa-2):

[Chem. 71]

$$(R^{5a})_3 N^{\oplus} \quad X^{\ominus}$$
$$|$$
$$(R^{6a})_z - O - R^{7a} \tag{IIa-2}$$

(wherein $R^{5a}$ is a C1-C6 alkyl group; $R^{6a}$ is a C1-C6 divalent hydrocarbon group; $R^{7a}$ is a C1-C4 alkyl group; z is 1 or 2; and $X^-$ is an anion). Introduction of an alkyl ether group enables reduction in viscosity.

The anion $X^-$ may be either an inorganic anion or an organic anion. Examples of the inorganic anion include $AlCl_4^-$, $BF_4^-$, $PF_6^-$, $AsF_6^-$, $TaF_6^-$, $I^-$, and $SbF_6^-$. Examples of the organic anion include a bisoxalatoborate anion, a difluorooxalatoborate anion, a tetrafluorooxalatophosphate anion, a difluorobisoxalatophosphate anion, $CF_3COO^-$, $CF_3SO_3^-$, $(CF_3SO_2)_2N^-$, and $(C_2F_5SO_2)_2N^-$.

In order to achieve good oxidation resistance and ionic dissociation, preferred are $BF_4^-$, $PF_6^-$, $AsF_6^-$, and $SbF_6^-$.

Preferred specific examples of the tetraalkyl quaternary ammonium salts to be used include $Et_4NBF_4$, $Et_4NCO_4$, $Et_4NPF_6$, $Et_4NAsF_6$, $Et_4NSbF_6$, $Et_4NCF_3SO_3$, $Et_4N(CF_3SO_2)_2N$, $Et_4NC_4F_9SO_3$, $Et_3MeNBF_4$, $Et_3MeNClO_4$, $Et_3MeNPF_6$, $Et_3MeNAsF_6$, $Et_3MeNSbF_6$, $Et_3MeNCF_3SO_3$, $Et_3MeN(CF_3SO_2)_2N$, and $Et_3MeNC_4F_9SO_3$. In particular, $Et_4NBF_4$, $Et_4NPF_6$, $Et_4NSbF_6$, $Et_4NAsF_6$, $Et_3MeNBF_4$, and an N,N-diethyl-N-methyl-N-(2-methoxyethyl)ammonium salt may be mentioned as examples.

(IIb) Spirocyclic Bipyrrolidinium Salts

Preferred examples thereof include spirocyclic bipyrrolidinium salts represented by the following formula (IIb-1):

[Chem. 72]

(IIb-1)

(wherein $R^{8a}$ and $R^{9a}$ are the same as or different from each other, and are each a C1-C4 alkyl group; $X^-$ is an anion; n1 is an integer of 0 to 5; and n2 is an integer of 0 to 5), spirocyclic bipyrrolidinium salts represented by the following formula (IIb-2):

[Chem. 73]

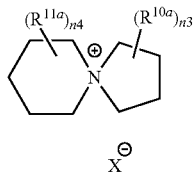

(IIb-2)

(wherein $R^{10a}$ and $R^{11a}$ are the same as or different from each other, and are each a C1-C4 alkyl group; $X^-$ is an anion; n3 is an integer of 0 to 5; and n4 is an integer of 0 to 5), and spirocyclic bipyrrolidinium salts represented by the following formula (IIb-3):

[Chem. 74]

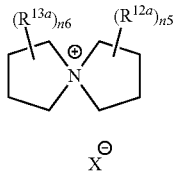

(IIb-3)

(wherein $R^{12a}$ and $R^{13a}$ are the same as or different from each other, and are each a C1-C4 alkyl group; $X^-$ is an anion; n5 is an integer of 0 to 5; and n6 is an integer of 0 to 5). In order to improve the oxidation resistance, any or all of the hydrogen atoms in the spirocyclic bipyrrolidinium salt are also preferably replaced by a fluorine atom and/or a C1-C4 fluorine-containing alkyl group.

Preferred specific examples of the anion $X^-$ are the same as those mentioned for the salts (IIa). In order to achieve good dissociation and a low internal resistance under high voltage, preferred among these is $BF_4^-$, $PF_6^-$, $(CF_3SO_2)_2N^-$, or $(C_2F_5SO_2)_2N^-$.

For example, those represented by the following formulae:

[Chem. 75]

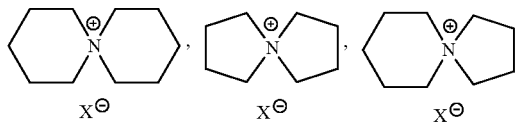

may be mentioned as preferred specific examples of the spirocyclic bipyrrolidinium salts.

These spirocyclic bipyrrolidinium salts are excellent in solubility in a solvent, oxidation resistance, and ion conductivity.

(IIc) Imidazolium Salts

Preferred examples thereof include imidazolium salts represented by the following formula (IIc):

[Chem. 76]

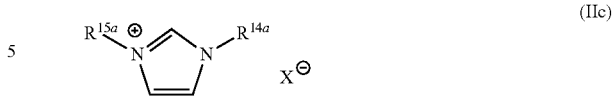

(IIc)

wherein $R^{14a}$ and $R^{15a}$ are the same as or different from each other, and are each a C1-C6 alkyl group; and $X^-$ is an anion.

In order to improve the oxidation resistance, any or all of the hydrogen atoms in the imidazolium salt are also preferably replaced by a fluorine atom and/or a C1-C4 fluorine-containing alkyl group.

Preferred specific examples of the anion $X^-$ are the same as those mentioned for the salts (IIa).

For example, one represented by the following formula:

[Chem. 77]

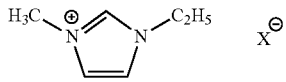

may be mentioned as a preferred specific example thereof.

This imidazolium salt is excellent in that it has low viscosity and good solubility.

(IId) N-Alkylpyridinium Salts

Preferred examples thereof include N-alkylpyridinium salts represented by the following formula (IId):

[Chem. 78]

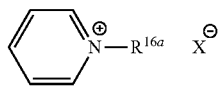

(IId)

wherein $R^{16a}$ is a C1-C6 alkyl group; and $X^-$ is an anion.

In order to improve the oxidation resistance, any or all of the hydrogen atoms in the N-alkylpyridinium salt are also preferably replaced by a fluorine atom and/or a C1-C4 fluorine-containing alkyl group.

Preferred specific examples of the anion $X^-$ are the same as those mentioned for the salts (IIa).

For example, those represented by the following formulae:

[Chem. 79]

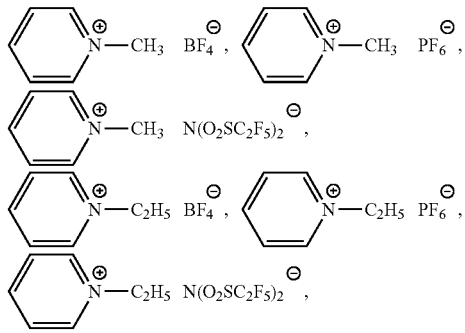

may be mentioned as preferred specific examples thereof.

These N-alkylpyridinium salts are excellent in that they have low viscosity and good solubility.

(IIe) N,N-dialkylpyrrolidinium salts

Preferred examples thereof include N,N-dialkylpyrrolidinium salts represented by the following formula (IIe):

[Chem. 80]

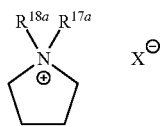

(IIe)

wherein $R^{17a}$ and $R^{18a}$ are the same as or different from each other, and are each a C1-C6 alkyl group; and $X^-$ is an anion.

In order to improve the oxidation resistance, any or all of the hydrogen atoms in the N,N-dialkylpyrrolidinium salt are also preferably replaced by a fluorine atom and/or a C1-C4 fluorine-containing alkyl group.

Preferred specific examples of the anion $X^-$ are the same as those mentioned for the salts (IIa).

For example, those represented by the following formulae:

[Chem. 81]

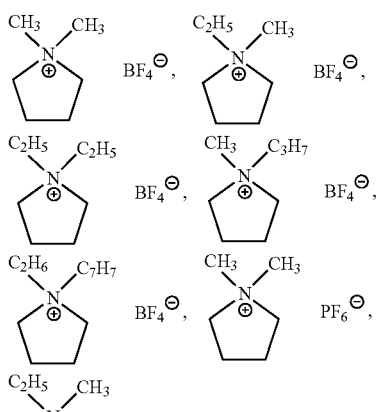

[Chem. 82]

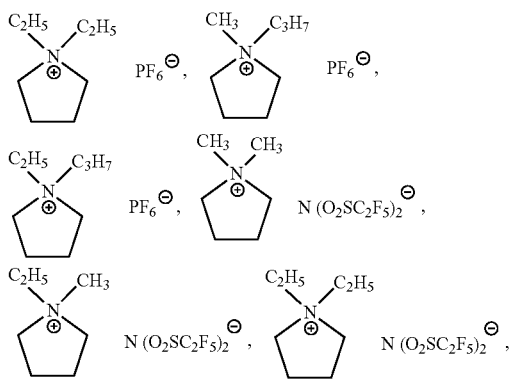

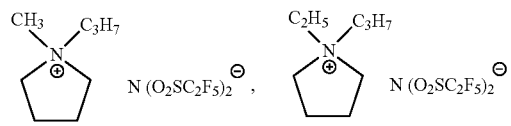

may be mentioned as preferred specific examples thereof.

These N,N-dialkylpyrrolidinium salts are excellent in that they have low viscosity and good solubility.

Preferred among these ammonium salts are those represented by the formula (IIa), (IIb), or (IIc) because they can have good solubility, oxidation resistance, and ion conductivity. More preferred are those represented by the following formulae:

[Chem. 83]

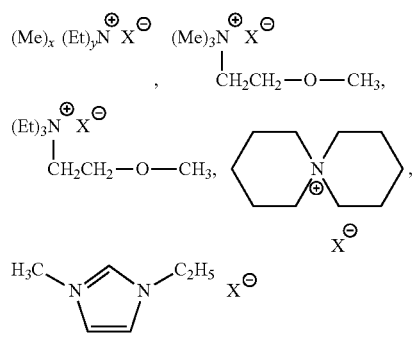

wherein Me is a methyl group; Et is an ethyl group; and $X^-$, x, and y are defined as in the formula (IIa-1).

A lithium salt may be used as an electrolyte salt for an electric double layer capacitor. Preferred examples thereof include $LiPF_6$, $LiBF_4$, $LiN(FSO_2)_2$, $LiAsF_6$, $LiSbF_6$, and $LiN(SO_2C_2H_5)_2$.

In order to further increase the capacity, a magnesium salt may be used. Preferred examples of the magnesium salt include $Mg(ClO_4)_2$ and $Mg(OOC_2H_5)_2$.

The ammonium salt serving as an electrolyte salt is preferably used at a concentration of 0.7 mol/L or higher. The ammonium salt at a concentration lower than 0.7 mol/L may cause not only poor low-temperature characteristics but also high initial internal resistance. The concentration of the electrolyte salt is more preferably 0.9 mol/L or higher.

In order to give good low-temperature characteristics, the upper limit of the concentration is preferably 2.0 mol/L or lower, more preferably 1.5 mol/L or lower.

When the ammonium salt is triethyl methyl ammonium tetrafluoroborate ($TEMABF_4$), the concentration is preferably 0.7 to 1.5 mol/L to give excellent low-temperature characteristics.

When the ammonium salt is spirobipyrrolidinium tetrafluoroborate ($SBPBF_4$) the concentration is preferably 0.7 to 2.0 mol/L.

The electrolyte solution of the invention preferably further contains a compound (2) represented by the following formula (2):

[Chem. 84]

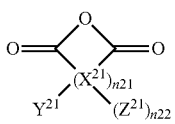

(wherein $X^{21}$ is a group containing at least H or C; $n^{21}$ is an integer of 1 to 3; $Y^{21}$ and $Z^{21}$ are the same as or different from each other, and are each a group containing at least H, C, O, or F; $n^{22}$ is 0 or 1; and $Y^{21}$ and $Z^{21}$ optionally bind to each other to form a ring). The electrolyte solution containing the compound (2) can cause much less reduction in capacity retention and can cause a much less increase in amount of gas generated even when stored at high temperature.

When $n^{21}$ is 2 or 3, the two or three $X^{21}$s may be the same as or different from each other.

When multiple $Y^{21}$s and multiple $Z^{21}$s are present, the multiple $Y^{21}$s may be the same as or different from each other and the multiple $Z^{21}$s may be the same as or different from each other.

$X^{21}$ is preferably a group represented by —$CY^{21}Z^{21}$— (wherein $Y^{21}$ and $Z^{21}$ are defined as described above) or a group represented by —$CY^2$=$CZ^2$— (wherein $Y^{21}$ and $Z^{21}$ are defined as described above).

$Y^{21}$ preferably includes at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

$Z^{21}$ preferably includes at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

Alternatively, $Y^{21}$ and $Z^{21}$ may bind to each other to form a carbon ring or heterocycle that may contain an unsaturated bond and may have aromaticity. The ring preferably has a carbon number of 3 to 20.

Next, specific examples of the compound (2) are described. In the following examples, the term "analog" means an acid anhydride obtainable by replacing part of the structure of an acid anhydride mentioned as an example by another structure within the scope of the invention. Examples thereof include dimers, trimers, and tetramers each composed of a plurality of acid anhydrides, structural isomers such as those having a substituent that has the same carbon number but also has a branch, and those having a different site at which a substituent binds to the acid anhydride.

Specific examples of an acid anhydride having a 5-membered cyclic structure include succinic anhydride, methylsuccinic anhydride (4-methylsuccinic anhydride), dimethylsuccinic anhydride (e.g., 4,4-dimethylsuccinic anhydride, 4,5-dimethylsuccinic anhydride), 4,4,5-trimethylsuccinic anhydride, 4,4,5,5-tetramethylsuccinic anhydride, 4-vinylsuccinic anhydride, 4,5-divinylsuccinic anhydride, phenylsuccinic anhydride (4-phenylsuccinic anhydride), 4,5-diphenylsuccinic anhydride, 4,4-diphenylsuccinic anhydride, citraconic anhydride, maleic anhydride, methylmaleic anhydride (4-methylmaleic anhydride), 4,5-dimethylmaleic anhydride, phenylmaleic anhydride (4-phenylmaleic anhydride), 4,5-diphenylmaleic anhydride, itaconic anhydride, 5-methylitaconic anhydride, 5,5-dimethylitaconic anhydride, phthalic anhydride, and 3,4,5,6-tetrahydrophthalic anhydride, and analogs thereof.

Specific examples of an acid anhydride having a 6-membered cyclic structure include cyclohexanedicarboxylic anhydride (e.g., cyclohexane-1,2-dicarboxylic anhydride), 4-cyclohexene-1,2-dicarboxylic anhydride, glutaric anhydride, glutaconic anhydride, and 2-phenylglutaric anhydride, and analogs thereof.

Specific examples of an acid anhydride having a different cyclic structure include 5-norbornene-2,3-dicarboxylic anhydride, cyclopentanetetracarboxylic dianhydride, pyromellitic anhydride, and diglycolic anhydride, and analogs thereof.

Specific examples of an acid anhydride having a cyclic structure and substituted with a halogen atom include monofluorosuccinic anhydride (e.g., 4-fluorosuccinic anhydride), 4,4-difluorosuccinic anhydride, 4,5-difluorosuccinic anhydride, 4,4,5-trifluorosuccinic anhydride, trifluoromethylsuccinic anhydride, tetrafluorosuccinic anhydride (4,4,5,5-tetrafluorosuccinic anhydride), 4-fluoromaleic anhydride, 4,5-difluoromaleic anhydride, trifluoromethylmaleic anhydride, 5-fluoroitaconic anhydride, and 5,5-difluoroitaconic anhydride, and analogs thereof.

Preferred among these as the compound (2) are glutaric anhydride, citraconic anhydride, glutaconic anhydride, itaconic anhydride, diglycolic anhydride, cyclohexanedicarboxylic anhydride, cyclopentanetetracarboxylic dianhydride, 4-cyclohexene-1,2-dicarboxylic anhydride, 3,4,5,6-tetrahydrophthalic anhydride, 5-norbornene-2,3-dicarboxylic anhydride, phenylsuccinic anhydride, 2-phenylglutaric anhydride, maleic anhydride, methylmaleic anhydride, trifluoromethylmaleic anhydride, phenylmaleic anhydride, succinic anhydride, methylsuccinic anhydride, dimethylsuccinic anhydride, trifluoromethylsuccinic anhydride, monofluorosuccinic anhydride, and tetrafluorosuccinic anhydride. More preferred are maleic anhydride, methylmaleic anhydride, trifluoromethylmaleic anhydride, succinic anhydride, methylsuccinic anhydride, trifluoromethylsuccinic anhydride, and tetrafluorosuccinic anhydride, and still more preferred are maleic anhydride and succinic anhydride.

The compound (2) preferably includes at least one selected from the group consisting of: a compound (3) represented by the following formula (3):

[Chem. 85]

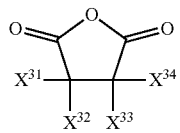

(wherein $X^{31}$ to $X^{34}$ are the same as or different from each other, and are each a group containing at least H, C, O, or F); and a compound (4) represented by the following formula (4):

[Chem. 86]

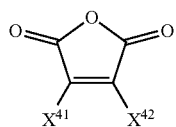

(wherein $X^{41}$ and $X^{42}$ are the same as or different from each other, and are each a group containing at least H, C, O, or F).

$X^{31}$ to $X^{34}$ are the same as or different from each other, and preferably include at least one selected from the group consisting of an alkyl group, a fluorinated alkyl group, an alkenyl group, and a fluorinated alkenyl group. $X^{31}$ to $X^{34}$ each preferably have a carbon number of 1 to 10, more preferably 1 to 3.

$X^{31}$ to $X^{34}$ are the same as or different from each other, and more preferably include at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

$X^{41}$ and $X^{42}$ are the same as or different from each other, and preferably include at least one selected from the group consisting of an alkyl group, a fluorinated alkyl group, an alkenyl group, and a fluorinated alkenyl group. $X^{41}$ and $X^{42}$ each preferably have a carbon number of 1 to 10, more preferably 1 to 3.

$X^{41}$ and $X^{42}$ are the same as or different from each other, and more preferably include at least one selected from the group consisting of H—, F—, $CH_3$—, $CH_3CH_2$—, $CH_3CH_2CH_2$—, $CF_3$—, $CF_3CF_2$—, $CH_2FCH_2$—, and $CF_3CF_2CF_2$—.

The compound (3) is preferably any of the following compounds.

[Chem. 87]

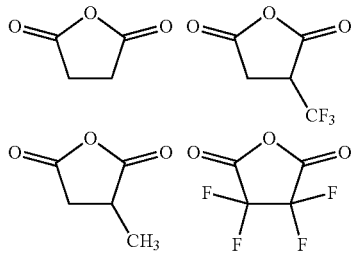

The compound (4) is preferably any of the following compounds.

[Chem. 88]

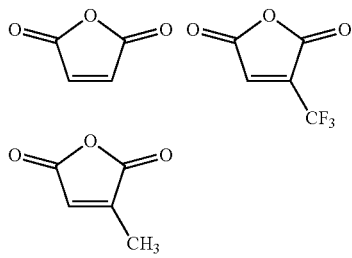

In order to cause much less reduction in capacity retention and a much less increase in amount of gas generated even when stored at high temperature, the electrolyte solution preferably contains 0.0001 to 15% by mass of the compound (2) relative to the electrolyte solution. The amount of the compound (2) is more preferably 0.01 to 10% by mass, still more preferably 0.1 to 3% by mass, particularly preferably 0.1 to 1.0% by mass.

In order to cause much less reduction in capacity retention and a much less increase in amount of gas generated even when stored at high temperature, the electrolyte solution, when containing both the compounds (3) and (4), preferably contains 0.08 to 2.50% by mass of the compound (3) and 0.02 to 1.50% by mass of the compound (4), more preferably 0.80 to 2.50% by mass of the compound (3) and 0.08 to 1.50% by mass of the compound (4), relative to the electrolyte solution.

The electrolyte solution of the invention may contain at least one selected from the group consisting of nitrile compounds represented by the following formulae (1a), (1b), and (1c):

[Chem. 89]

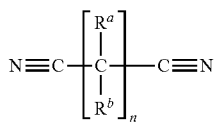

(1a)

(wherein $R^a$ and $R^b$ are each individually a hydrogen atom, a cyano group (CN), a halogen atom, an alkyl group, or a group obtainable by replacing at least one hydrogen atom of an alkyl group by a halogen atom; and n is an integer of 1 to 10)

[Chem. 90]

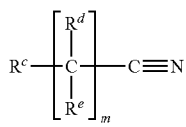

(1b)

(wherein $R^C$ is a hydrogen atom, a halogen atom, an alkyl group, a group obtainable by replacing at least one hydrogen atom of an alkyl group by a halogen atom, or a group represented by NC—$R^{c1}$—$X^{c1}$— (wherein $R^{c1}$ is an alkylene group, $X^{c1}$ is an oxygen atom or a sulfur atom); $R^d$ and $R^e$ are each individually a hydrogen atom, a halogen atom, an alkyl group, or a group obtainable by replacing at least one hydrogen atom of an alkyl group by a halogen atom; and m is an integer of 1 to 10);

[Chem. 91]

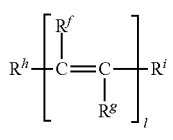

(1c)

(wherein $R^f$, $R^g$, $R^h$, and $R^i$ are each individually a group containing a cyano group (CN), a hydrogen atom (H), a halogen atom, an alkyl group, or a group obtainable by replacing at least one hydrogen atom of an alkyl group by a halogen atom; at least one selected from $R^f$, $R^g$, $R^h$, and $R^i$ is a group containing a cyano group; and l is an integer of 1 to 3).

This can improve the high-temperature storage characteristics of an electrochemical device. One nitrile compound may be used alone, or two or more thereof may be used in any combination at any ratio.

In the formula (1a), $R^a$ and $R^b$ are each individually a hydrogen atom, a cyano group (CN), a halogen atom, an alkyl group, or a group obtainable by replacing at least one hydrogen atom of an alkyl group by a halogen atom.

Examples of the halogen atom include a fluorine atom, a chlorine atom, a bromine atom, and an iodine atom. Preferred among these is a fluorine atom.

The alkyl group is preferably a C1-C5 alkyl group. Specific examples of the alkyl group include a methyl group, an ethyl group, a propyl group, an isopropyl group, a butyl group, an isobutyl group, and a tert-butyl group.

An example of the group obtainable by replacing at least one hydrogen atom of an alkyl group by a halogen atom is a group obtainable by replacing at least one hydrogen atom of the aforementioned alkyl group by the aforementioned halogen atom.

When $R^a$ and $R^b$ are alkyl groups or groups each obtainable by replacing at least one hydrogen atom of an alkyl group by a halogen atom, $R^a$ and $R^b$ may bind to each other to form a cyclic structure (e.g., a cyclohexane ring).

$R^a$ and $R^b$ are each preferably a hydrogen atom or an alkyl group.

In the formula (1a), n is an integer of 1 to 10. When n is 2 or greater, all of n $R^a$s may be the same as each other, or at least part of them may be different from the others. The same applies to $R^b$. In the formula, n is preferably an integer of 1 to 7, more preferably an integer of 2 to 5.

Preferred as the nitrile compound represented by the formula (1a) are dinitriles and tricarbonitriles.

Specific examples of the dinitriles include malononitrile, succinonitrile, glutaronitrile, adiponitrile, pimelonitrile, suberonitrile, azelanitrile, sebaconitrile, undecanedinitrile, dodecanedinitrile, methylmalononitrile, ethylmalononitrile, isopropylmalononitrile, tert-butylmalononitrile, methylsuccinonitrile, 2,2-dimethylsuccinonitrile, 2,3-dimethylsuccinonitrile, 2,3,3-trimethylsuccinonitrile, 2,2,3,3-tetramethylsuccinonitrile, 2,3-diethyl-2,3-dimethylsuccinonitrile, 2,2-diethyl-3,3-dimethylsuccinonitrile, bicyclohexyl-1,1-dicarbonitrile, bicyclohexyl-2,2-dicarbonitrile, bicyclohexyl-3,3-dicarbonitrile, 2,5-dimethyl-2,5-hexanedicarbonitrile, 2,3-diisobutyl-2,3-dimethylsuccinonitrile, 2,2-diisobutyl-3,3-dimethylsuccinonitrile, 2-methylglutaronitrile, 2,3-dimethylglutaronitrile, 2,4-dimethylglutaronitrile, 2,2,3,3-tetramethylglutaronitrile, 2,2,4,4-tetramethylglutaronitrile, 2,2,3,4-tetramethylglutaronitrile, 2,3,3,4-tetramethylglutaronitrile, 1,4-dicyanopentane, 2,6-dicyanoheptane, 2,7-dicyanooctane, 2,8-dicyanononane, 1,6-dicyanodecane, 1,2-dicyanobenzene, 1,3-dicyanobenzene, 1,4-dicyanobenzene, 3,3'-(ethylenedioxy)dipropionitrile, 3,3'-(ethylenedithio)dipropionitrile, 3,9-bis(2-cyanoethyl)-2,4,8,10-tetraoxaspiro[5,5]undecane, butanenitrile, and phthalonitrile. Particularly preferred among these are succinonitrile, glutaronitrile, and adiponitrile.

Specific examples of the tricarbonitriles include pentanetricarbonitrile, propanetricarbonitrile, 1,3,5-hexanetricarbonitrile, 1,3,6-hexanetricarbonitrile, heptanetricarbonitrile, 1,2,3-propanetricarbonitrile, 1,3,5-pentanetricarbonitrile, cyclohexanetricarbonitrile, triscyanoethylamine, triscyanoethoxypropane, tricyanoethylene, and tris(2-cyanoethyl)amine. Particularly preferred are 1,3,6-hexanetricarbonitrile and cyclohexanetricarbonitrile, most preferred is cyclohexanetricarbonitrile.

In the formula (1b), $R^c$ is a hydrogen atom, a halogen atom, an alkyl group, a group obtainable by replacing at least one hydrogen atom of an alkyl group by a halogen atom, or a group represented by NC—$R^{c1}$—$X^{c1}$— (wherein $R^{c1}$ is an alkylene group; and $X^{c1}$ is an oxygen atom or a sulfur atom);

$R^d$ and $R^e$ are each individually a hydrogen atom, a halogen atom, an alkyl group, or a group obtainable by replacing at least one hydrogen atom of an alkyl group by a halogen atom.

Examples of the halogen atom, the alkyl group, and the group obtainable by replacing at least one hydrogen atom of an alkyl group by a halogen atom include those mentioned as examples thereof for the formula (1a).

$R^{c1}$ in NC—$R^{c1}$—$X^{c1}$— is an alkylene group. The alkylene group is preferably a C1-C3 alkylene group.

$R^c$, $R^d$, and $R^e$ are each preferably individually a hydrogen atom, a halogen atom, an alkyl group, or a group obtainable by replacing at least one hydrogen atom of an alkyl group by a halogen atom.

At least one selected from $R^c$, $R^d$, and $R^e$ is preferably a halogen atom or a group obtainable by replacing at least one hydrogen atom of an alkyl group by a halogen atom, more preferably a fluorine atom or a group obtainable by replacing at least one hydrogen atom of an alkyl group by a fluorine atom.

When $R^d$ and $R^e$ are each an alkyl group or a group obtainable by replacing at least one hydrogen atom of an alkyl group by a halogen atom, $R^d$ and $R^e$ may bind to each other to form a cyclic structure (e.g., a cyclohexane ring).

In the formula (1b), m is an integer of 1 to 10. When m is 2 or greater, all of m $R^d$s may be the same as each other, or at least part of them may be different from the others. The same applies to $R^e$. In the formula, m is preferably an integer of 2 to 7, more preferably an integer of 2 to 5.

Examples of the nitrile compound represented by the formula (1b) include acetonitrile, propionitrile, butyronitrile, isobutyronitrile, valeronitrile, isovaleronitrile, lauronitrile, 3-methoxypropionitrile, 2-methylbutyronitrile, trimethylacetonitrile, hexanenitrile, cyclopentanecarbonitrile, cyclohexanecarbonitrile, fluoroacetonitrile, difluoroacetonitrile, trifluoroacetonitrile, 2-fluoropropionitrile, 3-fluoropropionitrile, 2,2-difluoropropionitrile, 2,3-difluoropropionitrile, 3,3-difluoropropionitrile, 2,2,3-trifluoropropionitrile, 3,3,3-trifluoropropionitrile, 3,3'-oxydipropionitrile, 3,3'-thiodipropionitrile, pentafluoropropionitrile, methoxyacetonitrile, and benzonitrile. Particularly preferred among these is 3,3,3-trifluoropropionitrile.

In the formula (1c), $R^f$, $R^g$, $R^h$, and $R^i$ are each individually a group containing a cyano group (CN), a hydrogen atom, a halogen atom, an alkyl group, or a group obtainable by replacing at least one hydrogen atom of an alkyl group by a halogen atom.

Examples of the halogen atom, the alkyl group, and the group obtainable by replacing at least one hydrogen atom of an alkyl group by a halogen atom include those mentioned as examples thereof for the formula (1a).

Examples of the group containing a cyano group include a cyano group and a group obtainable by replacing at least one hydrogen atom of an alkyl group by a cyano group. Examples of the alkyl group in this case include those mentioned as examples for the formula (1a).

At least one selected from $R^f$, $R^g$, $R^h$, and $R^i$ is a group containing a cyano group. Preferably, at least two selected from $R^f$, $R^g$, $R^h$, and $R^i$ are each a group containing a cyano group. More preferably, $R^h$ and $R^i$ are each a group containing a cyano group. When $R^h$ and $R^i$ are each a group containing a cyano group, $R^f$ and $R^g$ are preferably hydrogen atoms.

In the formula (1c), l is an integer of 1 to 3. When l is 2 or greater, all of l $R^f$s may be the same as each other, or at least part of them may be different from the others. The same applies to $R^g$. In the formula, 1 is preferably an integer of 1 or 2.

Examples of the nitrile compound represented by the formula (1c) include 3-hexenedinitrile, mucononitrile, maleonitrile, fumaronitrile, acrylonitrile, methacrylonitrile, crotononitrile, 3-methylcrotononitrile, 2-methyl-2-butenenitrile, 2-pentenenitrile, 2-methyl-2-pentenenitrile, 3-methyl-2-pentenenitrile, and 2-hexenenitrile. Preferred are 3-hexenedinitrile and mucononitrile, particularly preferred is 3-hexenedinitrile.

The nitrile compounds are preferably present in an amount of 0.2 to 7% by mass relative to the electrolyte solution. This can further improve the high-temperature storage characteristics and safety of an electrochemical device at high voltage. The lower limit of the total amount of the nitrile compounds is more preferably 0.3% by mass, still more preferably 0.5% by mass. The upper limit thereof is more preferably 5% by mass, still more preferably 2% by mass, particularly preferably 0.5% by mass.

The electrolyte solution of the invention may contain a compound containing an isocyanate group (hereinafter, also abbreviated as "isocyanate"). The isocyanate used may be any isocyanate. Examples of the isocyanate include monoisocyanates, diisocyanates, and triisocyanates.

Specific examples of the monoisocyanate include isocyanatomethane, isocyanatoethane, 1-isocyanatopropane, 1-isocyanatobutane, 1-isocyanatopentane, 1-isocyanatohexane, 1-isocyanatoheptane, 1-isocyanatooctane, 1-isocyanatononane, 1-isocyanatodecane, isocyanatocyclohexane, methoxycarbonyl isocyanate, ethoxycarbonyl isocyanate, propoxycarbonyl isocyanate, butoxycarbonyl isocyanate, methoxysulfonyl isocyanate, ethoxysulfonyl isocyanate, propoxysulfonyl isocyanate, butoxysulfonyl isocyanate, fluorosulfonyl isocyanate, methyl isocyanate, butyl isocyanate, phenyl isocyanate, 2-isocyanatoethyl acrylate, 2-isocyanatoethyl methacrylate, and ethyl isocyanate.

Specific examples of the diisocyanates include 1,4-diisocyanatobutane, 1,5-diisocyanatopentane, 1,6-diisocyanatohexane, 1,7-diisocyanatoheptane, 1,8-diisocyanatooctane, 1,9-diisocyanatononane, 1,10-diisocyanatodecane, 1,3-diisocyanatopropene, 1,4-diisocyanato-2-butene, 1,4-diisocyanato-2-fluorobutane, 1,4-diisocyanato-2,3-difluorobutane, 1,5-diisocyanato-2-pentene, 1,5-diisocyanato-2-methylpentane, 1,6-diisocyanato-2-hexene, 1,6-diisocyanato-3-hexene, 1,6-diisocyanato-3-fluorohexane, 1,6-diisocyanato-3,4-difluorohexane, toluene diisocyanate, xylene diisocyanate, tolylene diisocyanate, 1,2-bis(isocyanatomethyl)cyclohexane, 1,3-bis(isocyanatomethyl)cyclohexane, 1,4-bis(isocyanatomethyl)cyclohexane, 1,2-diisocyanatocyclohexane, 1,3-diisocyanatocyclohexane, 1,4-diisocyanatocyclohexane, dicyclohexylmethane-1,1'-diisocyanate, dicyclohexylmethane-2,2'-diisocyanate, dicyclohexylmethane-3,3'-diisocyanate, dicyclohexylmethane-4,4'-diisocyanate, isophorone diisocyanate, bicyclo[2.2.1]heptane-2,5-diylbis(methyl=isocyanate), bicyclo[2.2.1]heptane-2,6-diylbis(methyl=isocyanate), 2,4,4-trimethylhexamethylene diisocyanate, 2,2,4-trimethylhexamethylene diisocyanate, hexamethylene diisocyanate, 1,4-phenylene diisocyanate, octamethylene diisocyanate, and tetramethylene diisocyanate.

Specific examples of the triisocyanates include 1,6,11-triisocyanatoundecane, 4-isocyanatomethyl-1,8-octamethylene diisocyanate, 1,3,5-triisocyanatomethylbenzene, 1,3,5-tris(6-isocyanatohex-1-yl)-1,3,5-triazine-2,4,6(1H,3H,5H)-trione, and 4-(isocyanatomethyl)octamethylene=diisocyanate.

In order to enable industrially easy availability and cause low cost in production of an electrolyte solution, preferred among these are 1,6-diisocyanatohexane, 1,3-bis(isocyanatomethyl)cyclohexane, 1,3,5-tris(6-isocyanatohex-1-yl)-1,3,5-triazine-2,4,6(1H,3H,5H)-trione, 2,4,4-trimethylhexamethylene diisocyanate, and 2,2,4-trimethylhexamethylene diisocyanate. From the technical viewpoint, they can contribute to formation of a stable film-shaped structure and can therefore more suitably be used.

The isocyanate may be present in any amount that does not significantly impair the effects of the invention. The amount is preferably, but not limited to, 0.001% by mass or more and 1.0% by mass or less relative to the electrolyte solution. The isocyanate in an amount of not smaller than this lower limit can give a sufficient effect of improving the cycle characteristics to a non-aqueous electrolyte secondary battery. The isocyanate in an amount of not larger than this upper limit can eliminate an initial increase in resistance of a non-aqueous electrolyte secondary battery. The amount of the isocyanate is more preferably 0.01% by mass or more, still more preferably 0.1% by mass or more, particularly preferably 0.2% by mass or more, while more preferably 0.8% by mass or less, still more preferably 0.7% by mass or less, particularly preferably 0.6% by mass or less.

The electrolyte solution of the invention may contain a cyclic sulfonate. The cyclic sulfonate may be any cyclic sulfonate. Examples of the cyclic sulfonate include a saturated cyclic sulfonate, an unsaturated cyclic sulfonate, a saturated cyclic disulfonate, and an unsaturated cyclic disulfonate.

Specific examples of the saturated cyclic sulfonate include 1,3-propanesultone, 1-fluoro-1,3-propanesultone, 2-fluoro-1,3-propanesultone, 3-fluoro-1,3-propanesultone, 1-methyl-1,3-propanesultone, 2-methyl-1,3-propanesultone, 3-methyl-1,3-propanesultone, 1,3-butanesultone, 1,4-butanesultone, 1-fluoro-1,4-butanesultone, 2-fluoro-1,4-butanesultone, 3-fluoro-1,4-butanesultone, 4-fluoro-1,4-butanesultone, 1-methyl-1,4-butanesultone, 2-methyl-1,4-butanesultone, 3-methyl-1,4-butanesultone, 4-methyl-1,4-butanesultone, and 2,4-butanesultone.

Specific examples of the unsaturated cyclic sulfonate include 1-propene-1,3-sultone, 2-propene-1,3-sultone, 1-fluoro-1-propene-1,3-sultone, 2-fluoro-1-propene-1,3-sultone, 3-fluoro-1-propene-1,3-sultone, 1-fluoro-2-propene-1,3-sultone, 2-fluoro-2-propene-1,3-sultone, 3-fluoro-2-propene-1,3-sultone, 1-methyl-1-propene-1,3-sultone, 2-methyl-1-propene-1,3-sultone, 3-methyl-1-propene-1,3-sultone, 1-methyl-2-propene-1,3-sultone, 2-methyl-2-propene-1,3-sultone, 3-methyl-2-propene-1,3-sultone, 1-butene-1,4-sultone, 2-butene-1,4-sultone, 3-butene-1,4-sultone, 1-fluoro-1-butene-1,4-sultone, 2-fluoro-1-butene-1,4-sultone, 3-fluoro-1-butene-1,4-sultone, 4-fluoro-1-butene-1,4-sultone, 1-fluoro-2-butene-1,4-sultone, 2-fluoro-2-butene-1,4-sultone, 3-fluoro-2-butene-1,4-sultone, 4-fluoro-2-butene-1,4-sultone, 1,3-propenesultone, 1-fluoro-3-butene-1,4-sultone, 2-fluoro-3-butene-1,4-sultone, 3-fluoro-3-butene-1,4-sultone, 4-fluoro-3-butene-1,4-sultone, 1-methyl-1-butene-1,4-sultone, 2-methyl-1-butene-1,4-sultone, 3-methyl-1-butene-1,4-sultone, 4-methyl-1-butene-1,4-sultone, 1-methyl-2-butene-1,4-sultone, 2-methyl-2-butene-1,4-sultone, 3-methyl-2-butene-1,4-sultone, 4-methyl-2-butene-1,4-sultone, 1-methyl-3-butene-1,4-sultone, 2-methyl-3-butene-1,4-sultone, 3-methyl-3-butene-1,4-sultone, and 4-methyl-3-butene-14-sultone.

In order to enable easy availability and contribute to formation of a stable film-shaped structure, more preferred among these are 1,3-propanesultone, 1-fluoro-1,3-propanesultone, 2-fluoro-1,3-propanesultone, 3-fluoro-1,3-propanesultone, and 1-propene-1,3-sultone. The cyclic sulfonate may be in any amount that does not significantly impair the effects of the invention. The amount is preferably, but not limited to, 0.001% by mass or more and 3.0% by mass or less relative to the electrolyte solution.

The cyclic sulfonate in an amount of not smaller than this lower limit can give a sufficient effect of improving the cycle characteristics to a non-aqueous electrolyte secondary battery. The cyclic sulfonate in an amount of not larger than this upper limit can eliminate an increase in the cost of producing a non-aqueous electrolyte secondary battery. The amount of the cyclic sulfonate is more preferably 0.01% by mass or more, still more preferably 0.1% by mass or more, particularly preferably 0.2% by mass or more, while more preferably 2.5% by mass or less, still more preferably 2.0% by mass or less, particularly preferably 1.8% by mass or less.

The electrolyte solution of the invention may further contain a polyethylene oxide that has a weight average molecular weight of 2000 to 4000 and has —OH, —OCOOH, or —COOH at an end.

The presence of such a compound can improve the stability at the interfaces with the respective electrodes, improving the characteristics of an electrochemical device.

Examples of the polyethylene oxide include polyethylene oxide monool, polyethylene oxide carboxylate, polyethylene oxide diol, polyethylene oxide dicarboxylate, polyethylene oxide triol, and polyethylene oxide tricarboxylate. These may be used alone or in combination of two or more.

In order to give better characteristics of an electrochemical device, preferred are a mixture of polyethylene oxide monool and polyethylene oxide diol and a mixture of polyethylene carboxylate and polyethylene dicarboxylate.

The polyethylene oxide having too small a weight average molecular weight may be easily oxidatively decomposed. The weight average molecular weight is more preferably 3000 to 4000.

The weight average molecular weight can be determined by gel permeation chromatography (GPC) in polystyrene equivalent.

The polyethylene oxide is preferably present in an amount of $1\times10^{-6}$ to $1\times10^{-2}$ mol/kg in the electrolyte solution. Too large an amount of the polyethylene oxide may cause poor characteristics of an electrochemical device.

The amount of the polyethylene oxide is more preferably $5\times10^{-6}$ mol/kg or more.

The electrolyte solution of the invention may further contain, as an additive, any of other components such as a fluorinated saturated cyclic carbonate, an unsaturated cyclic carbonate, an overcharge inhibitor, and a known different aid. This can reduce impairment of the characteristics of an electrochemical device.

Examples of the fluorinated saturated cyclic carbonate include compounds represented by the aforementioned formula (A). Preferred among these are fluoroethylene carbonate, 4,5-difluoro-1,3-dioxolan-2-one, 2,2,3,3,3-pentafluoropropylethylene carbonate (4-(2,2,3,3,3-pentafluoro-propyl)-[1,3]dioxolan-2-one). One fluorinated saturated cyclic carbonate may be used alone, or two or more thereof may be used in any combination at any ratio.

The fluorinated saturated cyclic carbonate is preferably present in an amount of 0.001 to 10% by mass, more preferably 0.01 to 5% by mass, still more preferably 0.1 to 3% by mass, relative to the electrolyte solution.

Examples of the unsaturated cyclic carbonate include vinylene carbonate compounds, ethylene carbonate compounds substituted with a substituent that contains an aromatic ring, a carbon-carbon double bond, or a carbon-carbon triple bond, phenyl carbonate compounds, vinyl carbonate compounds, allyl carbonate compounds, and catechol carbonate compounds.

Examples of the vinylene carbonate compounds include vinylene carbonate, methylvinylene carbonate, 4,5-dimethylvinylene carbonate, phenylvinylene carbonate, 4,5-diphenylvinylene carbonate, vinylvinylene carbonate, 4,5-divinylvinylene carbonate, allylvinylene carbonate, 4,5-diallylvinylene carbonate, 4-fluorovinylene carbonate, 4-fluoro-5-methylvinylene carbonate, 4-fluoro-5-phenylvinylene carbonate, 4-fluoro-5-vinylvinylene carbonate, 4-allyl-5-fluorovinylene carbonate, ethynylethylene carbonate, propargylethylene carbonate, methylvinylene carbonate, and dimethylvinylene carbonate.

Specific examples of the ethylene carbonate compounds substituted with a substituent that contains an aromatic ring, a carbon-carbon double bond, or a carbon-carbon triple bond include vinylethylene carbonate, 4,5-divinylethylene carbonate, 4-methyl-5-vinylethylene carbonate, 4-allyl-5-vinylethylene carbonate, ethynylethylene carbonate, 4,5-diethynylethylene carbonate, 4-methyl-5-ethynylethylene carbonate, 4-vinyl-5-ethynylethylene carbonate, 4-allyl-5-ethynylethylene carbonate, phenylethylene carbonate, 4,5-diphenylethylene carbonate, 4-phenyl-5-vinylethylene carbonate, 4-allyl-5-phenylethylene carbonate, allylethylene carbonate, 4,5-diallylethylene carbonate, 4-methyl-5-allylethylene carbonate, 4-methylene-1,3-dioxolan-2-one, 4,5-dimethylene-1,3-dioxolan-2-one, and 4-methyl-5-allylethylene carbonate.

The unsaturated cyclic carbonate is preferably vinylene carbonate, methylvinylene carbonate, 4,5-dimethylvinylene carbonate, vinylvinylene carbonate, 4,5-vinylvinylene carbonate, allylvinylene carbonate, 4,5-diallylvinylene carbonate, vinylethylene carbonate, 4,5-divinylethylene carbonate, 4-methyl-5-vinylethylene carbonate, allylethylene carbonate, 4,5-diallylethylene carbonate, 4-methyl-5-allylethylene carbonate, 4-allyl-5-vinylethylene carbonate, ethynylethylene carbonate, 4,5-diethynylethylene carbonate, 4-methyl-5-ethynylethylene carbonate, and 4-vinyl-5-ethynylethylene carbonate. In order to form a more stable interface protecting film, particularly preferred are vinylene carbonate, vinylethylene carbonate, and ethynylethylene carbonate, and most preferred is vinylene carbonate.

The unsaturated cyclic carbonate may have any molecular weight that does not significantly impair the effects of the invention. The molecular weight is preferably 50 or higher and 250 or lower. The unsaturated cyclic carbonate having a molecular weight within this range can easily ensure its solubility in the electrolyte solution and can easily lead to sufficient achievement of the effects of the invention. The molecular weight of the unsaturated cyclic carbonate is more preferably 80 or higher and 150 or lower.

The unsaturated cyclic carbonate may be produced by any production method, and may be produced by a known method selected as appropriate.

One unsaturated cyclic carbonate may be used alone or two or more thereof may be used in any combination at any ratio.

The unsaturated cyclic carbonate may be present in any amount that does not significantly impair the effects of the invention. The amount of the unsaturated cyclic carbonate is preferably 0.001% by mass or more, more preferably 0.01% by mass or more, still more preferably 0.1% by mass or more, of 100% by mass of the electrolyte solution. The amount is preferably 5% by mass or less, more preferably 4% by mass or less, still more preferably 3% by mass or less.

The unsaturated cyclic carbonate in an amount within the above range allows an electrochemical device containing the electrolyte solution to easily exhibit a sufficient effect of improving the cycle characteristics, and can easily avoid a situation with impaired high-temperature storage characteristics, generation of a large amount of gas, and a reduced discharge capacity retention.

In addition to the aforementioned non-fluorinated unsaturated cyclic carbonates, a fluorinated unsaturated cyclic carbonate may also suitably be used as an unsaturated cyclic carbonate.

The fluorinated unsaturated cyclic carbonate is a cyclic carbonate containing an unsaturated bond and a fluorine atom. The number of fluorine atoms in the fluorinated unsaturated cyclic carbonate may be any number that is 1 or greater. The number of fluorine atoms is usually 6 or smaller, preferably 4 or smaller, most preferably 1 or 2.

Examples of the fluorinated unsaturated cyclic carbonate include fluorinated vinylene carbonate derivatives and fluorinated ethylene carbonate derivatives substituted with a substituent that contains an aromatic ring or a carbon-carbon double bond.

Examples of the fluorinated vinylene carbonate derivatives include 4-fluorovinylene carbonate, 4-fluoro-5-methylvinylene carbonate, 4-fluoro-5-phenylvinylene carbonate, 4-allyl-5-fluorovinylene carbonate, and 4-fluoro-5-vinylvinylene carbonate.

Examples of the fluorinated ethylene carbonate derivatives substituted with a substituent that contains an aromatic ring or a carbon-carbon double bond include 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate, 4,5-difluoro-4,5-diallylethylene carbonate, 4-fluoro-4-phenylethylene carbonate, 4-fluoro-5-phenylethylene carbonate, 4,4-difluoro-5-phenylethylene carbonate, and 4,5-difluoro-4-phenylethylene carbonate.

In order to form a stable interface protecting film, more preferably used as the fluorinated unsaturated cyclic carbonate are 4-fluorovinylene carbonate, 4-fluoro-5-methylvinylene carbonate, 4-fluoro-5-vinylvinylene carbonate, 4-allyl-5-fluorovinylene carbonate, 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate, and 4,5-difluoro-4,5-diallylethylene carbonate.

The fluorinated unsaturated cyclic carbonate may have any molecular weight that does not significantly impair the effects of the invention. The molecular weight is preferably 50 or higher and 500 or lower. The fluorinated unsaturated cyclic carbonate having a molecular weight within this range can easily ensure the solubility of the fluorinated unsaturated cyclic carbonate in the electrolyte solution.

The fluorinated unsaturated cyclic carbonate may be produced by any method, and may be produced by any known method selected as appropriate. The molecular weight is more preferably 100 or higher and 200 or lower.

One fluorinated unsaturated cyclic carbonate may be used alone or two or more thereof may be used in any combination at any ratio. The fluorinated unsaturated cyclic carbonate may be contained in any amount that does not significantly impair the effects of the invention. The amount of the fluorinated unsaturated cyclic carbonate is usually preferably 0.001% by mass or more, more preferably 0.01% by mass or more, still more preferably 0.1% by mass or more, while preferably 5% by mass or less, more preferably 4% by mass or less, still more preferably 3% by mass or less, of 100% by mass of the electrolyte solution. The fluorinated unsaturated cyclic carbonate in an amount within this range allows an electrochemical device containing the electrolyte solution to exhibit an effect of sufficiently improving the cycle characteristics and can easily avoid a situation with reduced high-temperature storage characteristics, generation of a large amount of gas, and a reduced discharge capacity retention.

The electrolyte solution of the invention may contain a compound containing a triple bond. This compound may be of any type as long as it contains one or more triple bonds in the molecule.

Specific examples of the compound containing a triple bond include the following compounds:

hydrocarbon compounds such as 1-penthyne, 2-penthyne, 1-hexyne, 2-hexyne, 3-hexyne, 1-heptyne, 2-heptyne, 3-heptyne, 1-octyne, 2-octyne, 3-octyne, 4-octyne, 1-nonyne, 2-nonyne, 3-nonyne, 4-nonyne, 1-dodecyne, 2-dodecyne, 3-dodecyne, 4-dodecyne, 5-dodecyne, phenyl acetylene, 1-phenyl-1-propyne, 1-phenyl-2-propyne, 1-phenyl-1-butyne, 4-phenyl-1-butyne, 4-phenyl-1-butyne, 1-phenyl-1-penthyne, 5-phenyl-1-penthyne, 1-phenyl-1-hexyne, 6-phenyl-1-hexyne, diphenyl acetylene, 4-ethynyl toluene, and dicyclohexyl acetylene;

monocarbonates such as 2-propynylmethyl carbonate, 2-propynylethyl carbonate, 2-propynylpropyl carbonate, 2-propynylbutyl carbonate, 2-propynylphenyl carbonate, 2-propynylcyclohexyl carbonate, di-2-propynylcarbonate, 1-methyl-2-propynylmethyl carbonate, 1,1-dimethyl-2-propynylmethyl carbonate, 2-butynylmethyl carbonate, 3-butynylmethyl carbonate, 2-pentynylmethyl carbonate, 3-pentynylmethyl carbonate, and 4-pentynylmethyl carbonate;

dicarbonates such as 2-butyne-1,4-diol dimethyl dicarbonate, 2-butyne-1,4-diol diethyl dicarbonate, 2-butyne-1,4-diol dipropyl dicarbonate, 2-butyne-1,4-diol dibutyl dicarbonate, 2-butyne-1,4-diol diphenyl dicarbonate, and 2-butyne-1,4-diol dicyclohexyl dicarbonate;

monocarboxylates such as 2-propynyl acetate, 2-propynyl propionate, 2-propynyl butyrate, 2-propynyl benzoate, 2-propynyl cyclohexylcarboxylate, 1,1-dimethyl-2-propynyl acetate, 1,1-dimethyl-2-propynyl propionate, 1,1-dimethyl-2-propynyl butyrate, 1,1-dimethyl-2-propynyl benzoate, 1,1-dimethyl-2-propynyl cyclohexylcarboxylate, 2-butynyl acetate, 3-butynyl acetate, 2-pentynyl acetate, 3-pentynyl acetate, 4-pentynyl acetate, methyl acrylate, ethyl acrylate, propyl acrylate, vinyl acrylate, 2-propenyl acrylate, 2-butenyl acrylate, 3-butenyl acrylate, methyl methacrylate, ethyl methacrylate, propyl methacrylate, vinyl methacrylate, 2-propenyl methacrylate, 2-butenyl methacrylate, 3-butenyl methacrylate, methyl 2-propynoate, ethyl 2-propynoate, propyl 2-propynoate, vinyl 2-propynoate, 2-propenyl 2-propynoate, 2-butenyl 2-propynoate, 3-butenyl 2-propynoate, methyl 2-butynoate, ethyl 2-butynoate, propyl 2-butynoate, vinyl 2-butynoate, 2-propenyl 2-butynoate, 2-butenyl 2-butynoate, 3-butenyl 2-butynoate, methyl 3-butynoate, ethyl 3-butynoate, propyl 3-butynoate, vinyl 3-butynoate, 2-propenyl 3-butynoate, 2-butenyl 3-butynoate, 3-butenyl 3-butynoate, methyl 2-penthynoate, ethyl 2-penthynoate, propyl 2-penthynoate, vinyl 2-penthynoate, 2-propenyl 2-penthynoate, 2-butenyl 2-penthynoate, 3-butenyl 2-penthynoate, methyl 3-penthynoate, ethyl 3-penthynoate, propyl 3-penthynoate, vinyl 3-penthynoate, 2-propenyl 3-penthynoate, 2-butenyl 3-penthynoate, 3-butenyl 3-penthynoate, methyl 4-penthynoate, ethyl 4-penthynoate, propyl 4-penthynoate, vinyl 4-penthynoate, 2-propenyl 4-penthynoate, 2-butenyl 4-penthynoate, and 3-butenyl 4-penthynoate, fumarates, methyl trimethylacetate, and ethyl trimethylacetate;

dicarboxylates such as 2-butyne-1,4-diol diacetate, 2-butyne-1,4-diol dipropionate, 2-butyne-1,4-diol dibutyrate, 2-butyne-1,4-diol dibenzoate, 2-butyne-1,4-diol dicyclohexanecarboxylate, hexahydrobenzo[1,3,2]dioxathiolane-2-oxide (1,2-cyclohexane diol, 2,2-dioxide-1,2-oxathiolan-4-yl acetate, and 2,2-dioxide-1,2-oxathiolan-4-yl acetate;

oxalic acid diesters such as methyl 2-propynyl oxalate, ethyl 2-propynyl oxalate, propyl 2-propynyl oxalate, 2-propynyl vinyl oxalate, allyl 2-propynyl oxalate, di-2-propynyl oxalate, 2-butynyl methyl oxalate, 2-butynyl ethyl oxalate, 2-butynyl propyl oxalate, 2-butynyl vinyl oxalate, allyl 2-butynyl oxalate, di-2-butynyl oxalate, 3-butynyl methyl oxalate, 3-butynyl ethyl oxalate, 3-butynyl propyl oxalate, 3-butynyl vinyl oxalate, allyl 3-butynyl oxalate, and di-3-butynyl oxalate;

phosphine oxides such as methyl(2-propynyl)(vinyl) phosphine oxide, divinyl(2-propynyl)phosphine oxide, di(2-propynyl)(vinyl)phosphine oxide, di(2-propenyl)2(-propynyl)phosphine oxide, di(2-propynyl)(2-propenyl)phosphine oxide, di(3-butenyl)(2-propynyl)phosphine oxide, and di(2-propynyl)(3-butenyl)phosphine oxide;

phosphinates such as 2-propynyl methyl(2-propenyl) phosphinate, 2-propynyl 2-butenyl(methyl)phosphinate, 2-propynyl di(2-propenyl)phosphinate, 2-propynyl di(3-butenyl)phosphinate, 1,1-dimethyl-2-propynyl methyl(2-propenyl)phosphinate, 1,1-dimethyl-2-propynyl 2-butenyl (methyl)phosphinate, 1,1-dimethyl-2-propynyl di(2-propenyl)phosphinate, 1,1-dimethyl-2-propynyl di(3-butenyl)phosphinate, 2-propenyl methyl(2-propynyl) phosphinate, 3-butenyl methyl(2-propynyl)phosphinate, 2-propenyl di(2-propynyl)phosphinate, 3-butenyl di(2-propynyl)phosphinate, 2-propenyl 2-propynyl(2-propenyl) phosphinate, and 3-butenyl 2-propynyl(2-propenyl)phosphinate;

phosphonates such as methyl 2-propynyl 2-propenylphosphonate, methyl(2-propynyl) 2-butenylphosphonate, (2-propynyl)(2-propenyl) 2-propenylphosphonate, (3-butenyl)(2-propynyl) 3-butenylphosphonate, (1,1-dimethyl-2-propynyl)(methyl) 2-propenylphosphonate, (1,1-dimethyl-2-propynyl)(methyl) 2-butenylphosphonate, (1,1-dimethyl-2-propynyl)(2-propenyl) 2-propenylphosphonate, (3-butenyl)(1,1-dimethyl-2-propynyl) 3-butenylphosphonate, (2-propynyl)(2-propenyl) methylphosphonate, (3-butenyl)(2-propynyl) methylphosphonate, (1,1-dimethyl-2-propynyl)(2-propenyl) methylphosphonate, (3-butenyl)(1,1-dimethyl-2-propynyl) methylphosphonate, (2-propynyl)(2-propenyl) ethylphosphonate, (3-butenyl)(2-propynyl) ethylphosphonate, (1,1-dimethyl-2-propynyl)(2-propenyl) ethylphosphonate, and (3-butenyl)(1,1-dimethyl-2-propynyl) ethylphosphonate; and phosphates such as (methyl)(2-propenyl)(2-propynyl) phosphate, (ethyl)(2-propenyl)(2-propynyl) phosphate, (2-butenyl)(methyl)(2-propynyl) phosphate, (2-butenyl) (ethyl)(2-propynyl) phosphate, (1,1-dimethyl-2-propynyl) (methyl)(2-propenyl) phosphate, (1,1-dimethyl-2-propynyl) (ethyl)(2-propenyl) phosphate, (2-butenyl)(1,1-dimethyl-2-propynyl)(methyl) phosphate, and (2-butenyl)(ethyl)(1,1-dimethyl-2-propynyl) phosphate.

In order to more stably form a negative electrode film in the electrolyte solution, preferred among these are compounds containing an alkynyloxy group.

In order to improve the storage characteristics, particularly preferred are compounds such as 2-propynylmethyl carbonate, di-2-propynyl carbonate, 2-butyne-1,4-diol dimethyl dicarbonate, 2-propynyl acetate, 2-butyne-1,4-diol diacetate, methyl 2-propynyl oxalate, and di-2-propynyl oxalate.

One compound containing a triple bond may be used alone or two or more thereof may be used in any combination at any ratio. The compound containing a triple bond may be present in any amount that does not significantly impair the effects of the invention relative to the whole electrolyte solution of the invention. The compound is usually contained at a concentration of 0.01% by mass or more, preferably 0.05% by mass or more, more preferably 0.1% by mass or more, while usually 5% by mass or less, preferably 3% by mass or less, more preferably 1% by mass or less, relative to the electrolyte solution of the invention. The compound satisfying the above range can further improve the effects such as output characteristics, load characteristics, cycle characteristics, and high-temperature storage characteristics.

In order to effectively reduce burst or combustion of a battery in case of overcharge, for example, of an electrochemical device containing the electrolyte solution, the electrolyte solution of the invention may contain an overcharge inhibitor.

Examples of the overcharge inhibitor include aromatic compounds, including unsubstituted or alkyl-substituted terphenyl derivatives such as biphenyl, o-terphenyl, m-terphenyl, and p-terphenyl, partially hydrogenated products of unsubstituted or alkyl-substituted terphenyl derivatives, cyclohexylbenzene, t-butylbenzene, t-amylbenzene, diphenyl ether, dibenzofuran, diphenyl cyclohexane, 1,1,3-trimethyl-3-phenylindan, cyclopentylbenzene, cyclohexylbenzene, cumene, 1,3-diisopropylbenzene, 1,4-diisopropylbenzene, t-butylbenzene, t-amylbenzene, t-hexylbenzene, and anisole; partially fluorinated products of the aromatic compounds such as 2-fluorobiphenyl, 4-fluorobiphenyl, o-cyclohexylfluorobenzene, p-cyclohexylfluorobenzene, o-cyclohexylfluorobenzene, p-cyclohexylfluorobenzene, fluorobenzene, fluorotoluene, and benzotrifluoride; fluorine-containing anisole compounds such as 2,4-difluoroanisole, 2,5-difluoroanisole, 1,6-difluoroanisole, 2,6-difluoroanisole, and 3,5-difluoroanisole; aromatic acetates such as 3-propylphenyl acetate, 2-ethylphenyl acetate, benzylphenyl acetate, methylphenyl acetate, benzyl acetate, and phenethylphenyl acetate; aromatic carbonates such as diphenyl carbonate and methylphenyl carbonate, toluene derivatives such as toluene and xylene, and unsubstituted or alkyl-substituted biphenyl derivatives such as 2-methylbiphenyl, 3-methylbiphenyl, 4-methylbiphenyl, and o-cyclohexylbiphenyl. Preferred among these are aromatic compounds such as biphenyl, alkylbiphenyl, terphenyl, partially hydrogenated terphenyl, cyclohexylbenzene, t-butylbenzene, t-amylbenzene, diphenyl ether, and dibenzofuran, diphenyl cyclohexane, 1,1,3-trimethyl-3-phenylindan, 3-propylphenyl acetate, 2-ethylphenyl acetate, benzylphenyl acetate, methylphenyl acetate, benzyl acetate, diphenyl carbonate, and methylphenyl carbonate. These compounds may be used alone or in combination of two or more. In order to achieve good balance between the overcharge inhibiting characteristics and the high-temperature storage characteristics with a combination use of two or more thereof, preferred is a combination of cyclohexylbenzene and t-butylbenzene or t-amylbenzene, or a combination of at least one oxygen-free aromatic compound selected from biphenyl, alkylbiphenyl, terphenyl, partially hydrogenated terphenyl, cyclohexylbenzene, t-butylbenzene, t-amylbenzene, and the like and at least one oxygen-containing aromatic compound selected from diphenyl ether, dibenzofuran, and the like.

The electrolyte solution used in the invention may contain a carboxylic anhydride other than the compound (2). Preferred is a compound represented by the following formula (6). The carboxylic anhydride may be produced by any method which may be selected from known methods as appropriate.

[Chem. 92]

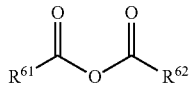

In the formula (6), $R^{61}$ and $R^{62}$ are each individually a hydrocarbon group having a carbon number of 1 or greater and 15 or smaller and optionally containing a substituent.

$R^{61}$ and $R^{62}$ each may be any monovalent hydrocarbon group. For example, each of them may be either an aliphatic hydrocarbon group or an aromatic hydrocarbon group, or may be a bond of an aliphatic hydrocarbon group and an aromatic hydrocarbon group. The aliphatic hydrocarbon group may be a saturated hydrocarbon group and may contain an unsaturated bond (carbon-carbon double bond or carbon-carbon triple bond). The aliphatic hydrocarbon group may be either acyclic or cyclic. In the case of an acyclic group, it may be either linear or branched. The group may be a bond of an acyclic group and a cyclic group. $R^{61}$ and $R^{62}$ may be the same as or different from each other.

When the hydrocarbon group for $R^{61}$ and $R^{62}$ contains a substituent, the substituent may be of any type as long as it is not beyond the scope of the invention. Examples thereof include halogen atoms such as a fluorine atom, a chlorine atom, a bromine atom, and an iodine atom. Preferred is a fluorine atom. Examples of the substituent other than the halogen atoms include substituents containing a functional group such as an ester group, a cyano group, a carbonyl group, or an ether group. Preferred are a cyano group and a carbonyl group. The hydrocarbon group for $R^{61}$ and $R^{62}$ may contain only one of these substituents or may contain two or more thereof. When two or more substituents are contained, these substituents may be the same as or different from each other.

The hydrocarbon group for $R^{61}$ and $R^{62}$ has a carbon number of usually 1 or greater, while usually 15 or smaller, preferably 12 or smaller, more preferably 10 or smaller, still more preferably 9 or smaller. When $R^1$ and $R^2$ bind to each other to form a divalent hydrocarbon group, the divalent hydrocarbon group has a carbon number of usually 1 or greater, while usually 15 or smaller, preferably 13 or smaller, more preferably 10 or smaller, still more preferably 8 or smaller. When the hydrocarbon group for $R^{61}$ and $R^{62}$ contains a substituent that contains a carbon atom, the carbon number of the whole $R^{61}$ or $R^{62}$ including the substituent preferably satisfies the above range.

Next, specific examples of the acid anhydride represented by the formula (6) are described. In the following examples, the term "analog" means an acid anhydride obtainable by replacing part of the structure of an acid anhydride mentioned as an example by another structure within the scope of the invention. Examples thereof include dimers, trimers, and tetramers each composed of a plurality of acid anhydrides, structural isomers such as those having a substituent that has the same carbon number but also has a branch, and those having a different site at which a substituent binds to the acid anhydride.

First, specific examples of an acid anhydride in which $R^{61}$ and $R^{62}$ are the same as each other are described.

Specific examples of an acid anhydride in which $R^{61}$ and $R^{62}$ are linear alkyl groups include acetic anhydride, propionic anhydride, butanoic anhydride, 2-methylpropionic anhydride, 2,2-dimethylpropionic anhydride, 2-methylbutanoic anhydride, 3-methylbutanoic anhydride, 2,2-dimethylbutanoic anhydride, 2,3-dimethylbutanoic anhydride, 3,3-dimethylbutanoic anhydride, 2,2,3-trimethylbutanoic anhydride, 2,3,3-trimethylbutanoic anhydride, 2,2,3,3-tetramethylbutanoic anhydride, and 2-ethylbutanoic anhydride, and analogs thereof.

Specific examples of an acid anhydride in which $R^{61}$ and $R^{62}$ are cyclic alkyl groups include cyclopropanecarboxylic anhydride, cyclopentanecarboxylic anhydride, and cyclohexanecarboxylic anhydride, and analogs thereof.

Specific examples of an acid anhydride in which $R^{61}$ and $R^{62}$ are alkenyl groups include acrylic anhydride, 2-methylacrylic anhydride, 3-methylacrylic anhydride, 2,3-dimethylacrylic anhydride, 3,3-dimethylacrylic anhydride, 2,3,3-trimethylacrylic anhydride, 2-phenylacrylic anhydride, 3-phenylacrylic anhydride, 2,3-diphenylacrylic anhydride, 3,3-diphenylacrylic anhydride, 3-butenoic anhydride, 2-methyl-3-butenoic anhydride, 2,2-dimethyl-3-butenoic anhydride, 3-methyl-3-butenoic anhydride, 2-methyl-3-methyl-3-butenoic anhydride, 2,2-dimethyl-3-methyl-3-butenoic anhydride, 3-pentenoic anhydride, 4-pentenoic anhydride, 2-cyclopentenecarboxylic anhydride, 3-cyclopentenecarboxylic anhydride, and 4-cyclopentenecarboxylic anhydride, and analogs thereof.

Specific examples of an acid anhydride in which $R^{61}$ and $R^{62}$ are alkynyl groups include propynoic anhydride, 3-phenylpropynoic anhydride, 2-butynoic anhydride, 2-penthynoic anhydride, 3-butynoic anhydride, 3-penthynoic anhydride, and 4-penthynoic anhydride, and analogs thereof.

Specific examples of an acid anhydride in which $R^{61}$ and $R^{62}$ are aryl groups include benzoic anhydride, 4-methylbenzoic anhydride, 4-ethylbenzoic anhydride, 4-tert-butylbenzoic anhydride, 2-methylbenzoic anhydride, 2,4,6-trimethylbenzoic anhydride, 1-naphthalenecarboxylic anhydride, and 2-naphthalenecarboxylic anhydride, and analogs thereof.

Examples of an acid anhydride substituted with a fluorine atom are mainly listed below as examples of the acid anhydride in which $R^{61}$ and $R^{62}$ are substituted with a halogen atom. Acid anhydrides obtainable by replacing any or all of the fluorine atoms thereof with a chlorine atom, a bromine atom, or an iodine atom are also included in the exemplary compounds.

Examples of an acid anhydride in which $R^{61}$ and $R^{62}$ are halogen-substituted linear alkyl groups include fluoroacetic anhydride, difluoroacetic anhydride, trifluoroacetic anhydride, 2-fluoropropionic anhydride, 2,2-difluoropropionic anhydride, 2,3-difluoropropionic anhydride, 2,2,3-trifluoropropionic anhydride, 2,3,3-trifluoropropionic anhydride, 2,2,3,3-tetrapropionic anhydride, 2,3,3,3-tetrapropionic anhydride, 3-fluoropropionic anhydride, 3,3-difluoropropionic anhydride, 3,3,3-trifluoropropionic anhydride, and perfluoropropionic anhydride, and analogs thereof.

Examples of an acid anhydride in which $R^{61}$ and $R^{62}$ are halogen-substituted cyclic alkyl groups include 2-fluorocyclopentanecarboxylic anhydride, 3-fluorocyclopentanecarboxylic anhydride, and 4-fluorocyclopentanecarboxylic anhydride, and analogs thereof.

Examples of an acid anhydride in which $R^{61}$ and $R^{62}$ are halogen-substituted alkenyl groups include 2-fluoroacrylic anhydride, 3-fluoroacrylic anhydride, 2,3-difluoroacrylic anhydride, 3,3-difluoroacrylic anhydride, 2,3,3-trifluoroacrylic anhydride, 2-(trifluoromethyl)acrylic anhydride, 3-(trifluoromethyl)acrylic anhydride, 2,3-bis(trifluoromethyl)acrylic anhydride, 2,3,3-tris(trifluoromethyl)acrylic anhydride, 2-(4-fluorophenyl)acrylic anhydride, 3-(4-fluorophenyl)acrylic anhydride, 2,3-bis(4-fluorophenyl)acrylic anhydride, 3,3-bis(4-fluorophenyl)acrylic anhydride, 2-fluoro-3-butenoic anhydride, 2,2-difluoro-3-butenoic anhydride, 3-fluoro-2-butenoic anhydride, 4-fluoro-3-butenoic anhydride, 3,4-difluoro-3-butenoic anhydride, and 3,3,4-trifluoro-3-butenoic anhydride, and analogs thereof.

Examples of an acid anhydride in which $R^{61}$ and $R^{62}$ are halogen-substituted alkynyl groups include 3-fluoro-2-propynoic anhydride, 3-(4-fluorophenyl)-2-propynoic anhydride, 3-(2,3,4,5,6-pentafluorophenyl)-2-propynoic anhydride, 4-fluoro-2-butynoic anhydride, 4,4-difluoro-2-butynoic anhydride, and 4,4,4-trifluoro-2-butynoic anhydride, and analogs thereof.

Examples of an acid anhydride in which $R^{61}$ and $R^{62}$ are halogen-substituted aryl groups include 4-fluorobenzoic anhydride, 2,3,4,5,6-pentafluorobenzoic anhydride, and 4-trifluoromethylbenzoic anhydride, and analogs thereof.

Examples of an acid anhydride in which $R^{61}$ and $R^{62}$ each contains a substituent containing a functional group such as an ester, a nitrile, a ketone, an ether, or the like include methoxyformic anhydride, ethoxyformic anhydride, methyloxalic anhydride, ethyloxalic anhydride, 2-cyanoacetic anhydride, 2-oxopropionic anhydride, 3-oxobutanoic anhydride, 4-acetylbenzoic anhydride, methoxyacetic anhydride, and 4-methoxybenzoic anhydride, and analogs thereof.

Then, specific examples of an acid anhydride in which $R^{61}$ and $R^{62}$ are different from each other are described below.

$R^{61}$ and $R^{62}$ may be in any combination of those mentioned as examples above and analogs thereof. The following gives representative examples.

Examples of a combination of linear alkyl groups include acetic propionic anhydride, acetic butanoic anhydride, butanoic propionic anhydride, and acetic 2-methylpropionic anhydride.

Examples of a combination of a linear alkyl group and a cyclic alkyl group include acetic cyclopentanoic anhydride, acetic cyclohexanoic anhydride, and cyclopentanoic propionic anhydride.

Examples of a combination of a linear alkyl group and an alkenyl group include acetic acrylic anhydride, acetic 3-methylacrylic anhydride, acetic 3-butenoic anhydride, and acrylic propionic anhydride.

Examples of a combination of a linear alkyl group and an alkynyl group include acetic propynoic anhydride, acetic 2-butynoic anhydride, acetic 3-butynoic anhydride, acetic 3-phenyl propynoic anhydride, and propionic propynoic anhydride.

Examples of a combination of a linear alkyl group and an aryl group include acetic benzoic anhydride, acetic 4-methylbenzoic anhydride, acetic 1-naphthalenecarboxylic anhydride, and benzoic propionic anhydride.

Examples of a combination of a linear alkyl group and a hydrocarbon group containing a functional group include acetic fluoroacetic anhydride, acetic trifluoroacetic anhydride, acetic 4-fluorobenzoic anhydride, fluoroacetic propionic anhydride, acetic alkyloxalic anhydride, acetic 2-cyanoacetic anhydride, acetic 2-oxopropionic anhydride, acetic methoxyacetic anhydride, and methoxyacetic propionic anhydride.

Examples of a combination of cyclic alkyl groups include cyclopentanoic cyclohexanoic anhydride.

Examples of a combination of a cyclic alkyl group and an alkenyl group include acrylic cyclopentanoic anhydride, 3-methylacrylic cyclopentanoic anhydride, 3-butenoic cyclopentanoic anhydride, and acrylic cyclohexanoic anhydride.

Examples of a combination of a cyclic alkyl group and an alkynyl group include propynoic cyclopentanoic anhydride, 2-butynoic cyclopentanoic anhydride, and propynoic cyclohexanoic anhydride.

Examples of a combination of a cyclic alkyl group and an aryl group include benzoic cyclopentanoic anhydride, 4-methylbenzoic cyclopentanoic anhydride, and benzoic cyclohexanoic anhydride.

Examples of a combination of a cyclic alkyl group and a hydrocarbon group containing a functional group include fluoroacetic cyclopentanoic anhydride, cyclopentanoic trifluoroacetic anhydride, cyclopentanoic 2-cyanoacetic anhydride, cyclopentanoic methoxyacetic anhydride, and cyclohexanoic fluoroacetic anhydride.

Examples of a combination of alkenyl groups include acrylic 2-methylacrylic anhydride, acrylic 3-methylacrylic anhydride, acrylic 3-butenoic anhydride, and 2-methylacrylic 3-methylacrylic anhydride.

Examples of a combination of an alkenyl group and an alkynyl group include acrylic propynoic anhydride, acrylic 2-butynoic anhydride, and 2-methylacrylic propynoic anhydride.

Examples of a combination of an alkenyl group and an aryl group include acrylic benzoic anhydride, acrylic 4-methylbenzoic anhydride, and 2-methylacrylic benzoic anhydride.

Examples of a combination of an alkenyl group and a hydrocarbon group containing a functional group include acrylic fluoroacetic anhydride, acrylic trifluoroacetic anhydride, acrylic 2-cyanoacetic anhydride, acrylic methoxyacetic anhydride, and 2-methylacrylic fluoroacetic anhydride.

Examples of a combination of alkynyl groups include propynoic 2-butynoic anhydride, propynoic 3-butynoic anhydride, and 2-butynoic 3-butynoic anhydride.

Examples of a combination of an alkynyl group and an aryl group include benzoic propynoic anhydride, 4-methylbenzoic propynoic anhydride, and benzoic 2-butynoic anhydride.

Examples of a combination of an alkynyl group and a hydrocarbon group containing a functional group include propynoic fluoroacetic anhydride, propynoic trifluoroacetic anhydride, propynoic 2-cyanoacetic anhydride, propynoic methoxyacetic anhydride, and 2-butynoic fluoroacetic anhydride.

Examples of a combination of aryl groups include benzoic 4-methylbenzoic anhydride, benzoic 1-naphthalenecarboxylic anhydride, and 4-methylbenzoic 1-naphthalenecarboxylic anhydride.

Examples of a combination of an aryl group and a hydrocarbon group containing a functional group include benzoic fluoroacetic anhydride, benzoic trifluoroacetic anhydride, benzoic 2-cyanoacetic anhydride, benzoic methoxyacetic anhydride, and 4-methylbenzoic fluoroacetic anhydride.

Examples of a combination of hydrocarbon groups each containing a functional group include fluoroacetic trifluoroacetic anhydride, fluoroacetic 2-cyanoacetic anhydride, fluoroacetic methoxyacetic anhydride, and trifluoroacetic 2-cyanoacetic anhydride.

Preferred among the acid anhydrides having an acyclic structure are acetic anhydride, propionic anhydride, 2-methylpropionic anhydride, cyclopentanecarboxylic anhydride, cyclohexanecarboxylic anhydride, acrylic anhydride, 2-methylacrylic anhydride, 3-methylacrylic anhydride, 2,3-dimethylacrylic anhydride, 3,3-dimethylacrylic anhydride, 3-butenoic anhydride, 2-methyl-3-butenoic anhydride, propynoic anhydride, 2-butynoic anhydride, benzoic anhydride, 2-methylbenzoic anhydride, 4-methylbenzoic anhydride, 4-tert-butylbenzoic anhydride, trifluoroacetic anhydride, 3,3,3-trifluoropropionic anhydride, 2-(trifluoromethyl) acrylic anhydride, 2-(4-fluorophenyl)acrylic anhydride, 4-fluorobenzoic anhydride, 2,3,4,5,6-pentafluorobenzoic anhydride, methoxyformic anhydride, and ethoxyformic anhydride. More preferred are acrylic anhydride, 2-methylacrylic anhydride, 3-methylacrylic anhydride, benzoic anhydride, 2-methylbenzoic anhydride, 4-methylbenzoic anhydride, 4-tert-butylbenzoic anhydride, 4-fluorobenzoic anhydride, 2,3,4,5,6-pentafluorobenzoic anhydride, methoxyformic anhydride, and ethoxyformic anhydride.

These compounds are preferred because they can appropriately form a bond with lithium oxalate to provide a film having excellent durability, thereby improving especially the charge and discharge rate characteristics after a durability test, input and output characteristics, and impedance characteristics.

The carboxylic anhydride may have any molecular weight that does not significantly impair the effects of the invention. The molecular weight is usually 90 or higher, preferably 95 or higher, while usually 300 or lower, preferably 200 or lower. The carboxylic anhydride having a molecular weight within the above range can reduce an increase in viscosity of an electrolyte solution and can give a reasonable film density, appropriately improving the durability.

The carboxylic anhydride may be formed by any production method which may be selected from known methods. One of the carboxylic anhydrides described above alone may be contained in the non-aqueous electrolyte solution of the invention, or two or more thereof may be contained in any combination at any ratio.

The carboxylic anhydride may be contained in any amount that does not significantly impair the effects of the invention relative to the electrolyte solution of the invention. The carboxylic anhydride is usually contained at a concentration of 0.01% by mass or more, preferably 0.1% by mass or more, while usually 5% by mass or less, preferably 3% by mass or less, relative to the electrolyte solution of the invention. The carboxylic anhydride in an amount within the above range can easily achieve an effect of improving the cycle characteristics and have good reactivity, easily improving the battery characteristics.

The electrolyte solution of the invention may further contain a known different aid. Examples of the different aid include carbonate compounds such as erythritan carbonate, spiro-bis-dimethylene carbonate, and methoxyethyl-methyl carbonate; spiro compounds such as 2,4,8,10-tetraoxaspiro[5.5]undecane and 3,9-divinyl-2,4,8,10-tetraoxaspiro[5.5]undecane; sulfur-containing compounds such as ethylene sulfite, methyl fluorosulfonate, ethyl fluorosulfonate, methyl methanesulfonate, ethyl methanesulfonate, busulfan, sulfolene, ethylene sulfate, vinylene sulfate, diphenyl sulfone, N,N-dimethylmethanesulfonamide, N,N-diethylmethanesulfonamide, acetamide, N-methyl formamide, N,N-dimethyl formamide, N,N-dimethyl acetamide, methyl vinyl sulfonate, ethyl vinyl sulfonate, allyl vinyl sulfonate, propargyl vinyl sulfonate, methyl allyl sulfonate, ethyl allyl sulfonate, allyl allyl sulfonate, propargyl allyl sulfonate, 1,2-bis(vinylsulfonyloxy)ethane, propanedisulfonic anhydride, sulfobutyric anhydride, sulfobenzoic anhydride, sulfopropionic anhydride, ethanedisulfonic anhydride, methylene methanedisulfonate, 2-propynyl methanesulfonate, pentene sulfite, pentafluorophenyl methanesulfonate, propylene sulfate, propylene sulfite, propane sultone, butylene sulfite, butane-2,3-diyl dimethanesulfonate, 2-butyne-1,4-diyl dimethanesulfonate, 2-phenyl bicyclohexyl, 2-butyne-1,4-diyl diformate, 2-propynyl vinyl sulfonate, bis(2-vinylsulfonylethyl)ether, 5-vinyl-hexahydro-1,3,2-benzodioxathiol-2-oxide, 2-propynyl 2-(methanesulfonyloxy)propionate, 5,5-dimethyl-1,2-oxathiolan-4-one 2,2-dioxide, 3-sulfo-propionic anhydride, trimethylene methanedisulfonate, 2-methyl tetrahydrofuran, trimethylene methanedisulfonate, tetramethylene sulfoxide, dimethylene methanedisulfonate, difluoroethyl methyl sulfone, divinyl sulfone, 1,2-bis(vinylsulfonyl)ethane, methyl ethylenebisphosphonate, ethyl ethylenebisphosphonate, and ethylene sulfate; nitrogen-containing compounds such as 1-methyl-2-pyrrolidinone, 1-methyl-2-piperidone, 3-methyl-2-oxazolidinone, 1,3-dimethyl-2-imidazolidinone, N-methylsuccinimide, nitromethane, nitroethane, thiophene 1-oxide, and ethylene diamine; phosphorus-containing compounds such as trimethyl phosphite, triethyl phosphite, triphenyl phosphite, trimethyl phosphate, triethyl phosphate, triphenyl phosphate, dimethyl methyl phosphonate, diethyl ethyl phosphonate, dimethyl vinyl phosphonate, diethyl vinyl phosphonate, ethyl diethyl phosphonoacetate, methyl dimethyl phosphinate, ethyl diethyl phosphinate, trimethylphosphine oxide, triethylphosphine oxide, bis(2,2-difluoroethyl) 2,2,2-trifluoroethyl phosphate, bis(2,2,3,3-tetrafluoropropyl)2,2,2-trifluoroethyl phosphate, bis(2,2,2-trifluoroethyl)methyl phosphate, bis(2,2,2-trifluoroethyl) ethyl phosphate, bis(2,2,2-trifluoroethyl)2,2-difluoroethyl phosphate, bis(2,2,2-trifluoroethyl)2,2,3,3-tetrafluoropropyl phosphate, tributyl phosphate, tris(2,2,2-trifluoroethyl) phosphate, tris(1,1,1,3,3,3-hexafluoropropan-2-yl) phosphate, trioctyl phosphate, 2-phenylphenyldimethyl phosphate, 2-phenylphenyldiethyl phosphate, (2,2,2-trifluoroethyl)(2,2,3,3-tetrafluoropropyl)methyl phosphate, phosphoric acid triester, methyl methylenebisphosphonate, ethyl methylenebisphosphonte, methyl 2-(dimethoxyphosphoryl)acetate, methyl 2-(dimethylphosphoryl)acetate, methyl 2-(diethoxyphosphoryl)acetate, methyl 2-(diethylphosphoryl)acetate, methyl butylenebisphosphonate, ethyl butylenebisphosphonate, 2-propynyl 2-(dimethoxyphosphoryl)acetate, 2-propynyl 2-(dimethylphosphoryl)acetate, 2-propynyl 2-(diethoxyphosphoryl)acetate, 2-propynyl 2-(diethylphosphoryl)acetate, tris(trimethylsilyl)phosphate, tris(trimethylsilyl)phosphite, tris(triethylsilyl)phosphate, and tris(triethylsilyl)phosphite; hydrocarbon compounds such as heptane, octane, nonane, decane, cycloheptane, methyl formate, methyl 2-propynyl oxalate, 2-propynyl methacrylate, dimethyl malonate, malonic acid ester, pentane, benzene, furan, naphthalene, 2,5,8,11-tetraoxadodecane, 2,5,8,11,14-pentaoxapentadecane, 3-pentanone, 2-phenyl bicyclohexyl, 3-allyl succinic anhydride, ethoxymethoxyethane, trimethoxymethane, and cyclohexane; fluorine-containing aromatic compounds such as fluorobenzene, difluorobenzene, hexafluorobenzene, benzotrifluoride, monofluorobenzene, 1-fluoro-2-cyclohexylbenzene, 1-fluoro-4-tert-butylbenzene, 1-fluoro-3-cyclohexylbenzene, 1-fluoro-2-cyclohexylbenzene, and fluorinated biphenyl; silane compounds such as tris(trimethylsilyl) borate, tris(trimethoxysilyl) borate, tris(trimethylsilyl) phosphate, tris(trimethoxysilyl) phosphate, dimethoxyaluminoxytrimethoxysilane, diethoxyaluminoxytriethoxysilane, dipropoxyaluminoxytriethoxysilane, dibutoxyaluminoxytrimethoxysilane, dibutoxyaluminoxytriethoxysilane, titanium tetrakis(trimethylsiloxide), titanium tetrakis(triethylsiloxide)1, tris(trimethylsilyl) phosphite, trimethylsilyl polyphosphate, and tetramethylsilane; and oxygen-containing compounds such as dimethyl oxalate, dioxolane, dioxane, dimethyl ketone, diethyl ketone, diethyl oxalate, di(2-propynyl)oxalate, dimethyl succinate, di(2-propynyl) glutarate, 2-propynyl formate, ethyl formate, glyme, ethyl monoglyme, ethylmethyl oxalate, and ethyl formate. One of these compounds may be used alone or two or more thereof may be used in combination. These aids can improve the capacity retention characteristics and the cycle characteristics after high-temperature storage.

Preferred among these as the different aid are phosphorus-containing compounds, especially preferred is tris(trimethylsilyl)phosphate.

The different aid may be present in any amount that does not significantly impair the effects of the invention. The amount of the different aid is preferably 0.01% by mass or more and 5% by mass or less of 100% by mass of the electrolyte solution. The different aid in an amount within this range can easily sufficiently exhibit the effects thereof and can easily avoid a situation with impairment of battery characteristics such as high-load discharge characteristics. The amount of the different aid is more preferably 0.1% by mass or more, still more preferably 0.2% by mass or more, while more preferably 3% by mass or less, still more preferably 1% by mass or less.

The electrolyte solution of the invention may further contain as an additive any of a cyclic carboxylate, an acyclic carboxylate, an ether compound, a nitrogen-containing compound, a boron-containing compound, an organosilicon-containing compound, a fireproof agent (flame retardant), a surfactant, an additive for increasing the permittivity, an improver for cycle characteristics and rate characteristics, and a sulfone-based compound to the extent that the effects of the invention are not impaired.

Examples of the cyclic carboxylate include those having a carbon number of 3 to 12 in total in the structural formula. Specific examples thereof include gamma-butyrolactone, gamma-valerolactone, gamma-caprolactone, epsilon-caprolactone, and 3-methyl-γ-butyrolactone. In order to improve the characteristics of an electrochemical device owing to improvement in the degree of dissociation of lithium ions, particularly preferred is gamma-butyrolactone.

In general, the cyclic carboxylate as an additive is preferably present in an amount of 0.1% by mass or more, more preferably 1% by mass or more, of 100% by mass of the solvent. The cyclic carboxylate in an amount within this range can easily improve the electric conductivity of the electrolyte solution, improving the large-current discharge characteristics of an electrochemical device. The amount of the cyclic carboxylate is also preferably 10% by mass or less, more preferably 5% by mass or less. Such an upper limit may allow the electrolyte solution to have a viscosity within an appropriate range, may make it possible to avoid a reduction in the electric conductivity, may reduce an increase in the resistance of the negative electrode, and may allow an electrochemical device to have large-current discharge characteristics within a favorable range.

The cyclic carboxylate to be suitably used may also be a fluorinated cyclic carboxylate (fluorine-containing lactone). Examples of the fluorine-containing lactone include fluorine-containing lactones represented by the following formula (C):

[Chem. 93]

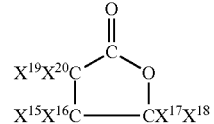

(C)

wherein $X^{15}$ to $X^{20}$ are the same as or different from each other, and are each —H, —F, —Cl, —CH$_3$, or a fluorinated alkyl group; and at least one selected from $X^{15}$ to $X^{20}$ is a fluorinated alkyl group.

Examples of the fluorinated alkyl group for $X^{15}$ to $X^{20}$ include —CFH$_2$, —CF$_2$H, —CF$_3$, —CH$_2$CF$_3$, —CF$_2$CF$_3$, —CH$_2$CF$_2$CF$_3$, and —CF(CF$_3$)$_2$. In order to achieve high oxidation resistance and an effect of improving the safety, —CH$_2$CF$_3$ and —CH$_2$CF$_2$CF$_3$ are preferred.

One of $X^{15}$ to $X^{20}$ or a plurality thereof may be replaced by —H, —F, —Cl, —CH$_3$, or a fluorinated alkyl group only when at least one selected from $X^{15}$ to $X^{20}$ is a fluorinated alkyl group. In order to give good solubility of an electrolyte salt, the number of substituents is preferably 1 to 3, more preferably 1 or 2.

The substitution of the fluorinated alkyl group may be at any of the above sites. In order to give a good synthesizing yield, the substitution site is preferably $X^{17}$ and/or $X^{18}$. In particular, $X^{17}$ or $X^{18}$ is preferably a fluorinated alkyl group, especially —CH$_2$CF$_3$ or —CH$_2$CF$_2$CF$_3$. The substituent for $X^{15}$ to $X^{20}$ other than the fluorinated alkyl group is —H, —F, —Cl, or CH$_3$. In order to give good solubility of an electrolyte salt, —H is preferred.

In addition to those represented by the above formula, the fluorine-containing lactone may also be a fluorine-containing lactone represented by the following formula (D):

[Chem. 94]

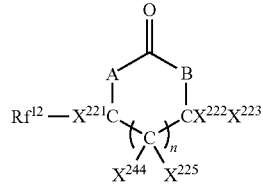

(D)

wherein one of A or B is $CX^{226}X^{227}$ (where $X^{226}$ and $X^{227}$ are the same as or different from each other, and are each —H, —F, —Cl, —CF$_3$, —CH$_3$, or an alkylene group in which a hydrogen atom is optionally replaced by a halogen atom and which optionally contains a hetero atom in the chain) and the other is an oxygen atom; $Rf^{12}$ is a fluorinated alkyl group or fluorinated alkoxy group optionally containing an ether bond; $X^{221}$ and $X^{222}$ are the same as or different from each other, and are each —H, —F, —Cl, —CF$_3$, or CH$_3$; $X^{223}$ to $X^{225}$ are the same as or different from each other, and are each —H, —F, —Cl, or an alkyl group in which a hydrogen atom is optionally replaced by a halogen atom and which optionally contains a hetero atom in the chain; and n=0 or 1.

A preferred example of the fluorine-containing lactone represented by the formula (D) is a 5-membered ring structure represented by the following formula (E):

[Chem. 95]

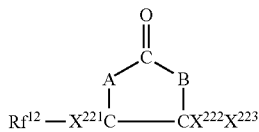

(E)

(wherein A, B, $Rf^{12}$, $X^{221}$, $X^{222}$, and $X^{223}$ are defined as in the formula (D)) because it can be easily synthesized and can have good chemical stability. Further, in relation to the combination of A and B, fluorine-containing lactones represented by the following formula (F):

[Chem. 96]

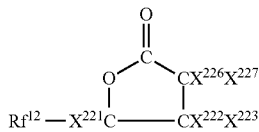

(F)

(wherein $Rf^{12}$, $X^{221}$, $X^{222}$, $X^{223}$, $X^{226}$, and $X^{227}$ are defined as in the formula (D)) and fluorine-containing lactones represented by the following formula (G):

[Chem. 97]

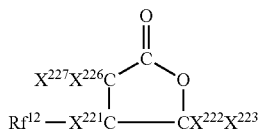

(G)

(wherein $Rf^{12}$, $X^{221}$, $X^{222}$, $X^{223}$, $X^{226}$, and $X^{227}$ are defined as in the formula (D)) may be mentioned.

In order to particularly give excellent characteristics such as high permittivity and high withstand voltage, and to improve the characteristics of the electrolyte solution in the invention, for example, to give good solubility of an electrolyte salt and to reduce the internal resistance well, those represented by the following formulae:

[Chem. 98]

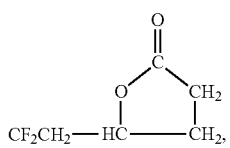

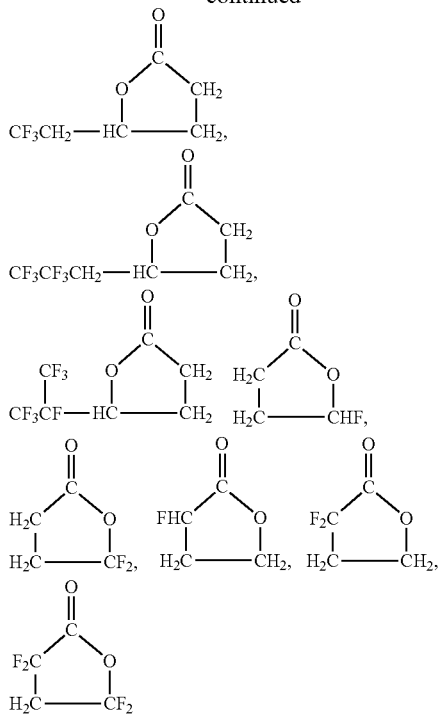

may be mentioned.

The presence of a fluorinated cyclic carboxylate can lead to, for example, effects of improving the ion conductivity, improving the safety, and improving the stability at high temperature.

Examples of the acyclic carboxylate include those having a carbon number of 3 to 7 in total in the structural formula thereof. Specific examples thereof include methyl acetate, ethyl acetate, n-propyl acetate, isopropyl acetate, n-butyl acetate, isobutyl acetate, t-butyl acetate, methyl propionate, ethyl propionate, n-propyl propionate, isobutyl propionate, n-butyl propionate, methyl butyrate, isobutyl propionate, t-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

In order to improve the ion conductivity owing to viscosity reduction, preferred among these are methyl acetate, ethyl acetate, n-propyl acetate, n-butyl acetate, methyl propionate, ethyl propionate, n-propyl propionate, isopropyl propionate, methyl butyrate, and ethyl butyrate.

The ether compound is preferably a C2-C10 acyclic ether or a C3-C6 cyclic ether.

Examples of the C2-C10 acyclic ether include dimethyl ether, diethyl ether, di-n-butyl ether, dimethoxymethane, methoxyethoxymethane, diethoxymethane, dimethoxyethane, methoxyethoxyethane, diethoxyethane, ethylene glycol di-n-propyl ether, ethylene glycol di-n-butyl ether, diethylene glycol, diethylene glycol dimethyl ether, pentaethylene glycol, triethylene glycol dimethyl ether, triethylene glycol, tetraethylene glycol, tetraethylene glycol dimethyl ether, and diisopropyl ether.

Further, the ether compound may also suitably be a fluorinated ether.

An example of the fluorinated ether is a fluorinated ether (I) represented by the following formula (I):

$$Rf^3—O—Rf^4 \qquad (I)$$

(wherein $Rf^3$ and $Rf^4$ are the same as or different from each other, and are each a C1-C10 alkyl group or a C1-C10 fluorinated alkyl group; and at least one selected from $Rf^3$ and $Rf^4$ is a fluorinated alkyl group). The presence of the fluorinated ether (I) allows the electrolyte solution to have improved incombustibility as well as improved stability and safety at high temperature under high voltage.

In the formula (I), at least one selected from $Rf^3$ and $Rf^4$ is a C1-C10 fluorinated alkyl group. In order to allow the electrolyte solution to have further improved incombustibility and further improved stability and safety at high temperature under high voltage, both $Rf^3$ and $Rf^4$ are preferably C1-C10 fluorinated alkyl groups. In this case, $Rf^3$ and $Rf^4$ may be the same as or different from each other.

Particularly preferably, $Rf^3$ and $Rf^4$ are the same as or different from each other, and $Rf^3$ is a C3-C6 fluorinated alkyl group and $Rf^4$ is a C2-C6 fluorinated alkyl group.

If the sum of the carbon numbers of $Rf^3$ and $Rf^4$ is too small, the fluorinated ether may have too low a boiling point. Too large a carbon number of $Rf^3$ or $Rf^4$ may cause low solubility of an electrolyte salt, may start to adversely affect the miscibility with other solvents, and may cause high viscosity, resulting in poor rate characteristics. In order to achieve an excellent boiling point and rate characteristics, advantageously, the carbon number of $Rf^3$ is 3 or 4 and the carbon number of $Rf^4$ is 2 or 3.

The fluorinated ether (I) preferably has a fluorine content of 40 to 75% by mass. The fluorinated ether (I) having a fluorine content within this range may lead to particularly excellent balance between the non-flammability and the miscibility. The above range is also preferred for good oxidation resistance and safety.

The lower limit of the fluorine content is more preferably 45% by mass, still more preferably 50% by mass, particularly preferably 55% by mass. The upper limit thereof is more preferably 70% by mass, still more preferably 66% by mass.

The fluorine content of the fluorinated ether (I) is a value calculated based on the structural formula of the fluorinated ether (I) by the following formula:

$$\{(\text{Number of fluorine atoms} \times 19)/(\text{Molecular weight of fluorinated ether(I)})\} \times 100(\%).$$

Examples of $Rf^3$ include $CF_3CF_2CH_2—$, $CF_3CFHCF_2—$, $HCF_2CF_2CF_2—$, $HCF_2CF_2CH_2—$, $CF_3CF_2CH_2CH_2—$, $CF_3CFHCF_2CH_2—$, $HCF_2CF_2CF_2CF_2—$, $HCF_2CF_2CF_2CH_2—$, $HCF_2CF_2CH_2CH_2—$, and $HCF_2CF(CF_3)CH_2—$. Examples of $Rf^4$ include $—CH_2CF_2CF_3$, $—CF_2CFHCF_3$, $—CF_2CF_2CF_2H$, $—CH_2CF_2CF_2H$, $—CH_2CH_2CF_2CF_3$, $—CH_2CF_2CFHCF_3$, $—CF_2CF_2CF_2CF_2H$, $—CH_2CF_2CF_2CF_3$, $—CH_2CH_2CF_2CF_2H$, $—CH_2CF(CF_3)CF_2H$, $—CF_2CF_2H$, $—CH_2CF_2H$, and $—CF_2CH_3$.

Specific examples of the fluorinated ether (I) include $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $C_6F_{13}OCH_3$, $C_6F_{13}OC_2H_5$, $C_8F_{17}OCH_3$, $C_8F_{17}OC_2H_5$, $CF_3CFHCF_2CH(CH_3)OCF_2CFHCF_3$, $HCF_2CF_2OCH(C_2H_5)_2$, $HCF_2CF_2OC_4H_9$, $HCF_2CF_2OCH_2CH(C_2H_5)_2$, and $HCF_2CF_2OCH_2CH(CH_3)_2$.

In particular, those having $HCF_2—$ or $CF_3CFH—$ at one or each end can provide a fluorinated ether (I) having excellent polarizability and a high boiling point. The boiling point of the fluorinated ether (I) is preferably 67° C. to 120° C., more preferably 80° C. or higher, still more preferably 90° C. or higher.

Such a fluorinated ether (I) may include one or two or more of $CF_3CH_2OCF_2CFHCF_3$, $CF_3CF_2CH_2OCF_2CFHCF_3$, $HCF_2CF_2CH_2OCF_2CFHCF_3$, $HCF_2CF_2CH_2OCH_2CF_2CF_2H$, $CF_3CFHCF_2CH_2OCF_2CFHCF_3$, $HCF_2CF_2CH_2OCF_2CF_2H$, $CF_3CF_2CH_2OCF_2CF_2H$, and the like.

Advantageously, in order to achieve a high boiling point and good miscibility with other solvents and to give good solubility of an electrolyte salt, the fluorinated ether (I) preferably include at least one selected from the group consisting of $HCF_2CF_2CH_2OCF_2CFHCF_3$ (boiling point: 106° C.), $CF_3CF_2CH_2OCF_2CFHCF_3$ (boiling point: 82° C.), $HCF_2CF_2CH_2OCF_2CF_2H$ (boiling point: 92° C.), and $CF_3CF_2CH_2OCF_2CF_2H$ (boiling point: 68° C.), more preferably at least one selected from the group consisting of $HCF_2CF_2CH_2OCF_2CFHCF_3$ (boiling point: 106° C.), and $HCF_2CF_2CH_2OCF_2CF_2H$ (boiling point: 92° C.).

Examples of the C3-C6 cyclic ether include 1,2-dioxane, 1,3-dioxane, 2-methyl-1,3-dioxane, 4-methyl-1,3-dioxane, 1,4-dioxane, metaformaldehyde, 2-methyl-1,3-dioxolane, 1,3-dioxolane, 4-methyl-1,3-dioxolane, 2-(trifluoroethyl)dioxolane, 2,2,-bis(trifluoromethyl)-1,3-dioxolane, and fluorinated compounds thereof. In order to achieve a high ability to solvate with lithium ions and improve the degree of ion dissociation, preferred are dimethoxymethane, diethoxymethane, ethoxymethoxymethane, ethylene glycol n-propyl ether, ethylene glycol di-n-butyl ether, diethylene glycol dimethyl ether, and crown ethers. In order to achieve low viscosity and to give a high ion conductivity, particularly preferred are dimethoxymethane, diethoxymethane, and ethoxymethoxymethane.

Examples of the nitrogen-containing compound include nitrile, fluorine-containing nitrile, carboxylic acid amide, fluorine-containing carboxylic acid amide, sulfonic acid amide, fluorine-containing sulfonic acid amide, acetamide, and formamide. Also, 1-methyl-2-pyrrolidinone, 1-methyl-2-piperidone, 3-methyl-2-oxazilidinone, 1,3-dimethyl-2-imidazolidinone, and N-methylsuccinimide may be used. The nitrile compounds represented by the formulae (1a), (1b), and (1c) are not included in the above nitrogen-containing compounds.

Examples of the boron-containing compound include borates such as trimethyl borate and triethyl borate, boric acid ethers, and alkyl borates.

Examples of the organosilicon-containing compound include $(CH_3)_4—Si$, $(CH_3)_3—Si—Si(CH_3)_3$, and silicone oil.

Examples of the fireproof agent (flame retardant) include organophosphates and phosphazene-based compounds. Examples of the organophosphates include fluorine-containing alkyl phosphates, non-fluorine-containing alkyl phosphates, and aryl phosphates. In order to achieve a flame retardant effect even in a small amount, fluorine-containing alkyl phosphates are particularly preferred.

Examples of the phosphazene-based compounds include methoxypentafluorocyclotriphosphazene, phenoxypentafluorocyclotriphosphazene, dimethylaminopentafluorocyclotriphosphazene, diethylaminopentafluorocyclotriphosphazene, ethoxypentafluorocyclotriphosphazene, and ethoxyheptafluorocyclotetraphosphazene.

Specific examples of the fluorine-containing alkyl phosphates include fluorine-containing dialkyl phosphates disclosed in JP H11-233141 A, cyclic alkyl phosphates disclosed in JP H11-283669 A, and fluorine-containing trialkyl phosphates.

Preferred examples of the fireproof agent (flame retardant) include $(CH_3O)_3P=O$, $(CF_3CH_2O)_3P=O$, $(HCF_2CH_2O)_3P=O$, $(CF_3CF_2CH_2)_3P=O$, and $(HCF_2CF_2CH_2)_3P=O$.

The surfactant may be any of cationic surfactants, anionic surfactants, nonionic surfactants, and amphoteric surfactants. In order to give good cycle characteristics and rate characteristics, the surfactant is preferably one containing a fluorine atom.

Preferred examples of such a surfactant containing a fluorine atom include fluorine-containing carboxylic acid salts represented by the following formula (30):

   (30)

(wherein $Rf^5$ is a C3-C10 fluorine-containing alkyl group optionally containing an ether bond; $M^+$ is $Li^+$, $Na^+$, $K^+$, or $NHR'_3{}^+$, wherein R's are the same as or different from each other, and are each H or a C1-C3 alkyl group), and fluorine-containing sulfonic acid salts represented by the following formula (40):

   (40)

(wherein $Rf^6$ is a C3-C10 fluorine-containing alkyl group optionally containing an ether bond; $M^+$ is $Li^+$, $Na^+$, $K^+$, or $NHR'_3{}^+$, wherein R's are the same as or different from each other, and are each H or a C1-C3 alkyl group).

In order to reduce the surface tension of the electrolyte solution without impairing the charge and discharge cycle characteristics, the surfactant is preferably present in an amount of 0.01 to 2% by mass of the electrolyte solution.

Examples of the additive for increasing the permittivity include sulfolane, methylsulfolane, γ-butyrolactone, and γ-valerolactone.

Examples of the improver for cycle characteristics and rate characteristics include methyl acetate, ethyl acetate, tetrahydrofuran, and 1,4-dioxane.

The electrolyte solution of the invention may be combined with a polymer material and thereby formed into a gel-like (plasticized), gel electrolyte solution.

Examples of such a polymer material include conventionally known polyethylene oxide and polypropylene oxide, and modified products thereof (see JP H08-222270 A, JP 2002-100405 A); polyacrylate-based polymers, polyacrylonitrile, and fluororesins such as polyvinylidene fluoride and vinylidene fluoride-hexafluoropropylene copolymers (see JP H04-506726 T, JP H08-507407 T, JP H10-294131 A); and composites of any of these fluororesins and any hydrocarbon resin (see JP H11-35765 A, JP H11-86630 A) In particular, polyvinylidene fluoride or a vinylidene fluoride-hexafluoropropylene copolymer is preferably used as a polymer material for a gel electrolyte.

The electrolyte solution of the invention may also contain an ion conductive compound disclosed in Japanese Patent Application No. 2004-301934.

This ion conductive compound is an amorphous fluorine-containing polyether compound having a fluorine-containing group at a side chain and is represented by the following formula (1-1):

   (1-1)

wherein D is represented by the following formula (2-1):

   (2-1)

[wherein D1 is an ether unit containing a fluorine-containing ether group at a side chain and is represented by the following formula (2a):

   (2a)

(wherein Rf is a fluorine-containing ether group optionally containing a crosslinkable functional group; and $R^{10}$ is a group or a bond that links Rf and the main chain);

FAE is an ether unit containing a fluorinated alkyl group at a side chain and is represented by the following formula (2b):

   (2b)

(wherein Rfa is a hydrogen atom or a fluorinated alkyl group optionally containing a crosslinkable functional group; and $R^{11}$ is a group or a bond that links Rfa and the main chain);

AE is an ether unit represented by the following formula (2c)

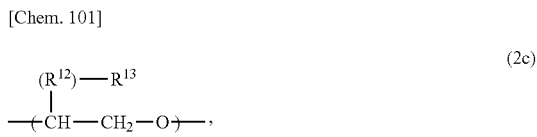   (2c)

(wherein $R^{13}$ is a hydrogen atom, an alkyl group optionally containing a crosslinkable functional group, an aliphatic cyclic hydrocarbon group optionally containing a crosslinkable functional group, or an aromatic hydrocarbon group optionally containing a crosslinkable functional group; and $R^{12}$ is a group or a bond that links $R^{13}$ and the main chain);

Y is a unit containing at least one selected from the following formulae (2d-1) to (2d-3):

   (2d-1)

   (2d-2)

   (2d-3)

n is an integer of 0 to 200;
m is an integer of 0 to 200;
p is an integer of 0 to 10000;
q is an integer of 1 to 100;
n+m is not 0; and the bonding order of D1, FAE, AE, and Y is not specified]; and A and B are the same as or different from each other, and are each a hydrogen atom, an alkyl group optionally containing a fluorine atom and/or a crosslinkable functional group, a phenyl group optionally containing a fluorine atom and/or a crosslinkable functional group, a —COOH group, —OR (where R is a hydrogen atom or an alkyl group optionally containing a fluorine atom and/or a crosslinkable functional group), an ester group, or a carbonate group, and when an end of D is an oxygen atom, A and B are each none of a —COOH group, —OR, an ester group, and a carbonate group.

The electrolyte solution of the invention may contain a sulfone-based compound. Preferred as the sulfone-based compound are a C3-C6 cyclic sulfone and a C2-C6 acyclic sulfone. The number of sulfonyl groups in one molecule is preferably 1 or 2.

Examples of the cyclic sulfone include monosulfone compounds such as trimethylene sulfones, tetramethylene sulfones, and hexamethylene sulfones; disulfone compounds such as trimethylene disulfones, tetramethylene disulfones, and hexamethylene disulfones. In order to give good permittivity and viscosity, more preferred among these are tetramethylene sulfones, tetramethylene disulfones, hexamethylene sulfones, and hexamethylene disulfones, particularly preferred are tetramethylene sulfones (sulfolanes).

The sulfolanes are preferably sulfolane and/or sulfolane derivatives (hereinafter, also abbreviated as "sulfolanes" including sulfolane). The sulfolane derivatives are preferably those in which one or more hydrogen atoms binding to any carbon atom constituting the sulfolane ring is replaced by a fluorine atom or an alkyl group.

In order to achieve high ion conductivity and high input and output, preferred among these are 2-methylsulfolane, 3-methylsulfolane, 2-fluorosulfolane, 3-fluorosulfolane, 2,2-difluorosulfolane, 2,3-difluorosulfolane, 2,4-difluorosulfolane, 2,5-difluorosulfolane, 3,4-difluorosulfolane, 2-fluoro-3-methylsulfolane, 2-fluoro-2-methylsulfolane, 3-fluoro-3-methylsulfolane, 3-fluoro-2-methylsulfolane, 4-fluoro-3-methylsulfolane, 4-fluoro-2-methylsulfolane, 5-fluoro-3-methylsulfolane, 5-fluoro-2-methylsulfolane, 2-fluoromethylsulfolane, 3-fluoromethylsulfolane, 2-difluoromethylsulfolane, 3-difluoromethylsulfolane, 2-trifluoromethylsulfolane, 3-trifluoromethylsulfolane, 2-fluoro-3-(trifluoromethyl)sulfolane, 3-fluoro-3-(trifluoromethyl)sulfolane, 4-fluoro-3-(trifluoromethyl)sulfolane, 3-sulfolene, 5-fluoro-3-(trifluoromethyl)sulfolane, and the like.

Examples of the acyclic sulfone include dimethyl sulfone, ethyl methyl sulfone, diethyl sulfone, n-propyl methyl sulfone, n-propyl ethyl sulfone, di-n-propyl sulfone, isopropyl methyl sulfone, isopropyl ethyl sulfone, diisopropyl sulfone, n-butyl methyl sulfone, n-butyl ethyl sulfone, t-butyl methyl sulfone, t-butyl ethyl sulfone, monofluoromethyl methyl sulfone, difluoromethyl methyl sulfone, trifluoromethyl methyl sulfone, monofluoroethyl methyl sulfone, difluoroethyl methyl sulfone, trifluoroethyl methyl sulfone, pentafluoroethyl methyl sulfone, ethyl monofluoromethyl sulfone, ethyl difluoromethyl sulfone, ethyl trifluoromethyl sulfone, perfluoroethyl methyl sulfone, ethyl trifluoroethyl sulfone, ethyl pentafluoroethyl sulfone, di(trifluoroethyl)sulfone, perfluorodiethyl sulfone, fluoromethyl-n-propyl sulfone, difluoromethyl-n-propyl sulfone, trifluoromethyl-n-propyl sulfone, fluoromethyl isopropyl sulfone, difluoromethyl isopropyl sulfone, trifluoromethyl isopropyl sulfone, trifluoroethyl-n-propyl sulfone, trifluoroethyl isopropyl sulfone, pentafluoroethyl-n-propyl sulfone, pentafluoroethyl isopropyl sulfone, trifluoroethyl-n-butyl sulfone, trifluoroethyl-t-butyl sulfone, pentafluoroethyl-n-butyl sulfone, and pentafluoroethyl-t-butyl sulfone.

In order to achieve high ion conductivity and high input and output, preferred among these are dimethyl sulfone, ethyl methyl sulfone, diethyl sulfone, n-propyl methyl sulfone, isopropyl methyl sulfone, n-butyl methyl sulfone, t-butyl methyl sulfone, monofluoromethyl methyl sulfone, difluoromethyl methyl sulfone, trifluoromethyl methyl sulfone, monofluoroethyl methyl sulfone, difluoroethyl methyl sulfone, trifluoroethyl methyl sulfone, pentafluoroethyl methyl sulfone, ethyl monofluoromethyl sulfone, ethyl difluoromethyl sulfone, ethyl trifluoromethyl sulfone, ethyl trifluoroethyl sulfone, ethyl pentafluoroethyl sulfone, trifluoromethyl-n-propyl sulfone, trifluoromethyl isopropyl sulfone, trifluoroethyl-n-butyl sulfone, trifluoroethyl-t-butyl sulfone, trifluoromethyl-n-butyl sulfone, trifluoromethyl-t-butyl sulfone, and the like.

The sulfone-based compound may be present in any amount that does not significantly impair the effects of the invention. The amount is usually 0.3% by volume or more, preferably 0.5% by volume or more, more preferably 1% by volume or more, while usually 40% by volume or less, preferably 35% by volume or less, more preferably 30% by volume or less, in 100% by volume of the solvent. The sulfone-based compound in an amount within the above range can easily achieve an effect of improving the cycle characteristics and the durability such as storage characteristics, can lead to an appropriate range of the viscosity of a non-aqueous electrolyte solution, can eliminate a reduction in electric conductivity, and can lead to appropriate ranges of the input and output characteristics and charge and discharge rate characteristics of a non-aqueous electrolyte secondary battery.

In order to improve the output characteristics, the electrolyte solution of the disclosure also preferably contains as an additive a compound (7) that is at least one selected from the group consisting of a lithium fluorophosphate other than $LiPF_6$ and a lithium salt containing a S=O group.

When the compound (7) is used as an additive, the above described electrolyte salt is preferably a compound other than the compound (7).

Examples of the lithium fluorophosphate include lithium monofluorophosphate ($LiPO_3F$) and lithium difluorophosphate ($LiPO_2F_2$).

Examples of the lithium salt containing a S=O group include lithium monofluorosulfonate ($FSO_3Li$), lithium methyl sulfate ($CH_3OSO_3Li$), lithium ethyl sulfate ($C_2H_5OSO_3Li$), and lithium 2,2,2-trifluoroethyl sulfate.

Preferred among these as the compound (7) are $LiPO_2F_2$, $FSO_3Li$, and $C_2H_5OSO_3Li$.

The compound (7) is preferably present in an amount of 0.001 to 20% by mass, more preferably 0.01 to 15% by mass, still more preferably 0.1 to 10% by mass, particularly preferably 0.1 to 7% by mass, relative to the electrolyte solution.

The electrolyte solution of the invention may further contain a different additive, if necessary. Examples of the different additive include metal oxides and glass.

The electrolyte solution of the invention preferably contains 5 to 200 ppm of hydrogen fluoride (HF). The presence of HF can promote formation of a film of the aforementioned additive. Too small an amount of HF tends to impair the ability to form a film on the negative electrode, impairing the characteristics of an electrochemical device. Too large an amount of HF tends to impair the oxidation resistance of the electrolyte solution due to the influence by HF. The electrolyte solution of the invention, even when containing HF in an amount within the above range, causes no reduction in capacity recovery of an electrochemical device after high-temperature storage.

The amount of HF is more preferably 10 ppm or more, still more preferably 20 ppm or more. The amount of HF is also more preferably 100 ppm or less, still more preferably 80 ppm or less, particularly preferably 50 ppm or less.

The amount of HF can be determined by neutralization titration.

The electrolyte solution of the invention is preferably prepared by any method using the aforementioned components.

The electrolyte solution of the invention can be suitably applied to electrochemical devices such as lithium ion secondary batteries, lithium ion capacitors, hybrid capacitors, and electric double layer capacitors. Hereinafter, a non-aqueous electrolyte battery including the electrolyte solution of the invention is described.

The non-aqueous electrolyte battery can have a known structure, typically including positive and positive electrodes that can occlude and release ions (e.g., lithium ions) and the electrolyte solution of the invention. Such an electrochemical device including the electrolyte solution of the invention is also one aspect of the invention.

Examples of the electrochemical devices include lithium ion secondary batteries, lithium ion capacitors, capacitors such as hybrid capacitors and electric double-layer capacitors, radical batteries, solar cells, in particular dye-sensitized solar cells, lithium ion primary batteries, fuel cells, various electrochemical sensors, electrochromic elements, electrochemical switching elements, aluminum electrolytic capacitors, and tantalum electrolytic capacitors. Preferred are lithium ion secondary batteries, lithium ion capacitors, and electric double-layer capacitors.

A module including the electrochemical device is also one aspect of the invention.

The invention also relates to a lithium ion secondary battery including the electrolyte solution of the invention.

The lithium ion secondary battery preferably includes a positive electrode, a negative electrode, and the above electrolyte solution.

<Positive Electrode>

The positive electrode includes a positive electrode active material layer containing a positive electrode active material and a current collector.

The positive electrode active material may be any material that can electrochemically occlude and release lithium ions. Examples thereof include lithium-containing transition metal complex oxides, lithium-containing transition metal phosphoric acid compounds, sulfides, and conductive polymers. Preferred among these as the positive electrode active material are lithium-containing transition metal complex oxides and lithium-containing transition metal phosphoric acid compounds. Particularly preferred is a lithium-containing transition metal complex oxide that generates high voltage.

The transition metal of the lithium-containing transition metal complex oxide is preferably V, Ti, Cr, Mn, Fe, Co, Ni, Cu, or the like. Specific examples thereof include lithium-cobalt complex oxides such as $LiCoO_2$, lithium-nickel complex oxides such as $LiNiO_2$, lithium-manganese complex oxides such as $LiMnO_2$, $LiMn_2O_4$, and $Li_2MnO_4$, and those obtained by substituting some of transition metal atoms as main components of these lithium transition metal complex oxides with another element such as Na, K, B, F, Al, Ti, V, Cr, Mn, Fe, Co, Li, Ni, Cu, Zn, Mg, Ga, Zr, Si, Nb, Mo, Sn, or W. Specific examples of those obtained by substitution include $LiNi_{0.5}Mn_{0.5}O_2$, $LiNi_{0.85}Co_{0.10}Al_{0.05}O_2$, $LiNi_{0.5}Co_{0.2}Mn_{0.3}O_2$, $LiNi_{0.6}Co_{0.2}Mn_{0.2}O_2$, $LiNi_{0.33}Co_{0.33}Mn_{0.33}O_2$, $LiNi_{0.45}Co_{0.10}Al_{0.45}O_2$, $LiMn_{1.8}Al_{0.2}O_4$, and $LiMn_{1.5}Ni_{0.5}O_4$.

The lithium-containing transition metal complex oxide is preferably any of $LiMn_{1.5}Ni_{0.5}O_4$, $LiNi_{0.5}Co_{0.2}Mn_{0.3}O_2$, and $LiNi_{0.6}Co_{0.2}Mn_{0.2}O_2$ each of which has a high energy density even at high voltage.

The transition metal of the lithium-containing transition metal phosphoric acid compound is preferably V, Ti, Cr, Mn, Fe, Co, Ni, Cu, or the like. Specific examples thereof include iron phosphates such as $LiFePO_4$, $Li_3Fe_2(PO_4)_3$, and $LiFeP_2O_7$, cobalt phosphates such as $LiCoPO_4$, and those obtained by substituting some of transition metal atoms as main components of these lithium transition metal phosphoric acid compounds with another element such as Al, Ti, V, Cr, Mn, Fe, Co, Li, Ni, Cu, Zn, Mg, Ga, Zr, Nb, or Si.

Examples of the lithium-containing transition metal complex oxide include lithium-manganese spinel complex oxides represented by the formula: $Li_aMn_{2-b}M^1_bO_4$ (wherein $0.9 \leq a$; $0 \leq b \leq 1.5$; and $M^1$ is at least one metal selected from the group consisting of Fe, Co, Ni, Cu, Zn, Al, Sn, Cr, V, Ti, Mg, Ca, Sr, B, Ga, In, Si, and Ge), lithium-nickel complex oxides represented by the formula: $LiNi_{1-c}M^2_cO_2$ (wherein $0 \leq c \leq 0.5$; and $M^2$ is at least one metal selected from the group consisting of Fe, Co, Mn, Cu, Zn, Al, Sn, Cr, V, Ti, Mg, Ca, Sr, B, Ga, In, Si, and Ge), and lithium-cobalt complex oxides represented by the formula: $LiCo_{1-d}M^3_dO_2$ (wherein $0 \leq d \leq 0.5$; and $M^3$ is at least one metal selected from the group consisting of Fe, Ni, Mn, Cu, Zn, Al, Sn, Cr, V, Ti, Mg, Ca, Sr, B, Ga, In, Si, and Ge).

In order to provide a high-power lithium ion secondary battery having a high energy density, preferred is $LiCoO_2$, $LiMnO_2$, $LiNiO_2$, $LiMn_2O_4$, $LiNi_{0.8}Co_{0.15}Al_{0.05}O_2$, or $LiNi_{1/3}Co_{1/3}Mn_{1/3}O_2$.

Other examples of the positive electrode active material include $LiFePO_4$, $LiNi_{0.8}Co_{0.2}O_2$, $Li_{1.2}Fe_{0.4}Mn_{0.4}O_2$, $LiNi_{0.5}Mn_{0.5}O_2$, and $LiV_3O_6$.

Examples of the sulfides include compounds having a 2D lamellar structure such as $TiS_2$ and $MoS_2$, and chevrel compounds having a strong 3D skeletal structure such as those represented by the formula: $Me_xMo_6S_8$ (wherein Me is a transition metal such as Pb, Ag, and Cu). Examples thereof also include simple sulfur and organolithium sulfides represented by $LiS_x$.

Examples of the conductive polymers include p-doped conductive polymers and n-doped conductive polymers. Examples of the conductive polymers include polyacetylene-based polymers, polyphenylene-based polymers, heterocyclic polymers, ionic polymers, ladder-shaped polymers, and network polymers.

In order to improve the continuous charge characteristics, the positive electrode active material preferably contains lithium phosphate. Lithium phosphate may be used in any manner, and is preferably used in admixture with the positive electrode active material. The lower limit of the amount of lithium phosphate used is preferably 0.1% by mass or more, more preferably 0.3% by mass or more, still more preferably 0.5% by mass or more, relative to the sum of the amounts of the positive electrode active material and lithium phosphate. The upper limit thereof is preferably 10% by mass or less, more preferably 8% by mass or less, still more preferably 5% by mass or less.

To a surface of the positive electrode active material may be attached a substance having a composition different from the positive electrode active material. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

Such a substance may be attached to a surface of the positive electrode active material by, for example, a method of dissolving or suspending the substance in a solvent, impregnating the solution or suspension into the positive electrode active material, and drying the impregnated material; a method of dissolving or suspending a precursor of the substance in a solvent, impregnating the solution or suspension into the positive electrode active material, and heating the material and the precursor to cause a reaction therebetween; or a method of adding the substance to a precursor of the positive electrode active material and simultaneously sintering the materials. In the case of attaching carbon, for example, a carbonaceous material in the form of activated carbon may be mechanically attached to the surface afterward.

For the amount of the substance attached to the surface in terms of the mass relative to the amount of the positive electrode active material, the lower limit thereof is preferably 0.1 ppm or more, more preferably 1 ppm or more, still more preferably 10 ppm or more, while the upper limit thereof is preferably 20% or less, more preferably 10% or less, still more preferably 5% or less. The substance attached to the surface can reduce oxidation of the electrolyte solution on the surface of the positive electrode active material, improving the battery life. Too small an amount of the substance may fail to sufficiently provide this effect. Too large an amount thereof may hinder the entrance and exit of lithium ions, increasing the resistance.

Particles of the positive electrode active material may have any shape conventionally used, such as a bulky shape, a polyhedral shape, a spherical shape, an ellipsoidal shape, a plate shape, a needle shape, or a pillar shape. The primary particles may agglomerate to form secondary particles.

The positive electrode active material has a tap density of preferably 0.5 g/cm$^3$ or higher, more preferably 0.8 g/cm$^3$ or higher, still more preferably 1.0 g/cm$^3$ or higher. The positive electrode active material having a tap density below the lower limit may cause an increased amount of a dispersion medium required and increased amounts of a conductive material and a binder required in formation of the positive electrode active material layer, as well as limitation on the packing fraction of the positive electrode active material in the positive electrode active material layer, resulting in limitation on the battery capacity. A complex oxide powder having a high tap density enables formation of a positive electrode active material layer with a high density. The tap density is preferably as high as possible and has no upper limit, in general. Still, too high a tap density may cause diffusion of lithium ions in the positive electrode active material layer with the electrolyte solution serving as a diffusion medium to function as a rate-determining step, easily impairing the load characteristics. Thus, the upper limit of the tap density is preferably 4.0 g/cm$^3$ or lower, more preferably 3.7 g/cm$^3$ or lower, still more preferably 3.5 g/cm$^3$ or lower.

In the invention, the tap density is determined as a powder packing density (tap density) g/cm$^3$ when 5 to 10 g of the positive electrode active material powder is packed into a 10-ml glass graduated cylinder and the cylinder is tapped 200 times with a stroke of about 20 mm.

The particles of the positive electrode active material have a median size d50 (or a secondary particle size when the primary particles agglomerate to form secondary particles) of preferably 0.3 µm or greater, more preferably 0.5 µm or greater, still more preferably 0.8 µm or greater, most preferably 1.0 µm or greater, while preferably 30 µm or smaller, more preferably 27 µm or smaller, still more preferably 25 µm or smaller, most preferably 22 µm or smaller. The particles having a median size below the lower limit may fail to provide a product with a high tap density. The particles having a median size greater than the upper limit may cause prolonged diffusion of lithium in the particles, impairing the battery performance and generating streaks in formation of the positive electrode for a battery, i.e., when the active material and components such as a conductive material and a binder are formed into slurry by adding a solvent and the slurry is applied in the form of a film, for example. Mixing two or more positive electrode active materials having different median sizes d50 can further improve the easiness of packing in formation of the positive electrode.

In the invention, the median size d50 is determined using a known laser diffraction/scattering particle size distribution analyzer. In the case of using LA-920 (Horiba, Ltd.) as the particle size distribution analyzer, the dispersion medium used in the measurement is a 0.1% by mass sodium hexametaphosphate aqueous solution and the measurement refractive index is set to 1.24 after 5-minute ultrasonic dispersion.

When the primary particles agglomerate to form secondary particles, the average primary particle size of the positive electrode active material is preferably 0.05 µm or greater, more preferably 0.1 µm or greater, still more preferably 0.2 µm or greater. The upper limit thereof is preferably 5 µm or smaller, more preferably 4 µm or smaller, still more preferably 3 µm or smaller, most preferably 2 µm or smaller. The primary particles having an average primary particle size greater than the upper limit may have difficulty in forming spherical secondary particles, adversely affecting the powder packing. Further, such primary particles may have a greatly reduced specific surface area, highly possibly impairing the battery performance such as output characteristics. In contrast, the primary particles having an average primary particle size below the lower limit may usually be insufficiently grown crystals, causing poor charge and discharge reversibility, for example.

In the invention, the primary particle size is measured by scanning electron microscopic (SEM) observation. Specifically, the primary particle size is determined as follows. A photograph at a magnification of 10000× is first taken. Any 50 primary particles are selected and the maximum length between the left and right boundary lines of each primary particle is measured along the horizontal line. Then, the average value of the maximum lengths is calculated, which is defined as the primary particle size.

The positive electrode active material has a BET specific surface area of preferably 0.1 m$^2$/g or larger, more preferably 0.2 m$^2$/g or larger, still more preferably 0.3 m$^2$/g or larger. The upper limit thereof is preferably 50 m$^2$/g or smaller, more preferably 40 m$^2$/g or smaller, still more preferably 30 m$^2$/g or smaller. The positive electrode active material having a BET specific surface area smaller than the above range may easily impair the battery performance. The positive electrode active material having a BET specific surface area larger than the above range may less easily have an increased tap density, easily causing a difficulty in applying the material in formation of the positive electrode active material layer.

In the invention, the BET specific surface area is defined by a value determined by single point BET nitrogen adsorption utilizing a gas flow method using a surface area analyzer (e.g., fully automatic surface area measurement device, Ohkura Riken Co., Ltd.), a sample pre-dried in nitrogen stream at 150° C. for 30 minutes, and a nitrogen-helium gas mixture with the nitrogen pressure relative to the atmospheric pressure being accurately adjusted to 0.3.

When the lithium ion secondary battery of the invention is used as a large-size lithium ion secondary battery for hybrid vehicles or distributed generation, it needs to achieve high output. Thus, the particles of the positive electrode active material preferably mainly composed of secondary particles.

The particles of the positive electrode active material preferably include 0.5 to 7.0% by volume of fine particles having an average secondary particle size of 40 μm or smaller and having an average primary particle size of 1 μm or smaller. The presence of fine particles having an average primary particle size of 1 μm or smaller enlarges the contact area with the electrolyte solution and enables more rapid diffusion of lithium ions between the electrode and the electrolyte solution, improving the output performance of the battery.

The positive electrode active material may be produced by any usual method of producing an inorganic compound. In particular, a spherical or ellipsoidal active material can be produced by various methods. For example, a material substance of transition metal is dissolved or crushed and dispersed in a solvent such as water, and the pH of the solution or dispersion is adjusted under stirring to form a spherical precursor. The precursor is recovered and, if necessary, dried. Then, a Li source such as LiOH, $Li_2CO_3$, or $LiNO_3$ is added thereto and the mixture is sintered at high temperature, thereby providing an active material.

In production of the positive electrode, the aforementioned positive electrode active materials may be used alone or in any combination of two or more thereof having different compositions at any ratio. Preferred examples of the combination in this case include a combination of $LiCoO_2$ and $LiMn_2O_4$ in which part of Mn may optionally be replaced by a different transition metal (e.g., $LiNi_{0.33}Co_{0.33}Mn_{0.33}O_2$), and a combination with $LiCoO_2$ in which part of Co may optionally be replaced by a different transition metal.

In order to achieve a high battery capacity, the amount of the positive electrode active material is preferably 50 to 99.5% by mass, more preferably 80 to 99% by mass, of the positive electrode mixture. The amount of the positive electrode active material in the positive electrode active material layer is preferably 80% by mass or more, more preferably 82% by mass or more, particularly preferably 84% by mass or more. The upper limit thereof is preferably 99% by mass or less, more preferably 98% by mass or less. Too small an amount of the positive electrode active material in the positive electrode active material layer may cause an insufficient electric capacity. In contrast, too large an amount thereof may cause insufficient strength of the positive electrode.

The positive electrode mixture preferably further contains a binder, a thickening agent, and a conductive material.

The binder may be any material that is safe against a solvent to be used in production of the electrode and the electrolyte solution. Examples thereof include resin polymers such as polyethylene, polypropylene, polyethylene terephthalate, polymethyl methacrylate, aromatic polyamide, chitosan, alginic acid, polyacrylic acid, polyimide, cellulose, and nitro cellulose; rubbery polymers such as SBR (styrene-butadiene rubber), isoprene rubber, butadiene rubber, fluoroelastomers, NBR (acrylonitrile-butadiene rubber), and ethylene-propylene rubber; styrene-butadiene-styrene block copolymers and hydrogenated products thereof; thermoplastic elastomeric polymers such as EPDM (ethylene-propylene-diene terpolymers), styrene-ethylene-butadiene-styrene copolymers, and styrene-isoprene-styrene block copolymers and hydrogenated products thereof; soft resin polymers such as syndiotactic-1,2-polybutadiene, polyvinyl acetate, ethylene-vinyl acetate copolymers, and propylene-α-olefin copolymers; fluoropolymers such as polyvinylidene fluoride, polytetrafluoroethylene, vinylidene fluoride copolymer, and tetrafluoroethylene-ethylene copolymers; and polymer compositions having ion conductivity of alkali metal ions (especially, lithium ions). These may be used alone or in any combination of two or more at any ratio.

The amount of the binder, which is expressed as the proportion of the binder in the positive electrode active material layer, is usually 0.1% by mass or more, preferably 1% by mass or more, more preferably 1.5% by mass or more. The proportion is also usually 80% by mass or less, preferably 60% by mass or less, still more preferably 40% by mass or less, most preferably 10% by mass or less. Too low a proportion of the binder may fail to sufficiently hold the positive electrode active material and cause insufficient mechanical strength of the positive electrode, impairing the battery performance such as cycle characteristics. In contrast, too high a proportion thereof may cause reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, polyvinylpyrrolidone, and salts thereof. These agents may be used alone or in any combination of two or more at any ratio.

The proportion of the thickening agent relative to the active material is usually 0.1% by mass or higher, preferably 0.2% by mass or higher, more preferably 0.3% by mass or higher, while usually 5% by mass or lower, preferably 3% by mass or lower, more preferably 2% by mass or lower. The thickening agent at a proportion lower than the above range may cause significantly poor easiness of application. The thickening agent at a proportion higher than the above range may cause a low proportion of the active material in the positive electrode active material layer, resulting in a low capacity of the battery and high resistance between the positive electrode active materials.

The conductive material may be any known conductive material. Specific examples thereof include metal materials such as copper and nickel, and carbon materials such as graphite, including natural graphite and artificial graphite, carbon black, including acetylene black, Ketjen black, channel black, furnace black, lamp black, and thermal black, and amorphous carbon, including needle coke, carbon nanotube, fullerene, and VGCF. These materials may be used alone or in any combination of two or more at any ratio. The conductive material is used in an amount of usually 0.01% by mass or more, preferably 0.1% by mass or more, more preferably 1% by mass or more, while usually 50% by mass or less, preferably 30% by mass or less, more preferably 15% by mass or less, in the positive electrode active material layer. The conductive material in an amount less than the above range may cause insufficient conductivity. In contrast, the conductive material in an amount more than the above range may cause a low battery capacity.

The solvent for forming slurry may be any solvent that can dissolve or disperse therein the positive electrode active material, the conductive material, and the binder, as well as a thickening agent used as appropriate. The solvent may be either an aqueous solvent or an organic solvent. Examples of the aqueous medium include water and solvent mixtures of an alcohol and water. Examples of the organic medium include aliphatic hydrocarbons such as hexane; aromatic hydrocarbons such as benzene, toluene, xylene, and methyl naphthalene; heterocyclic compounds such as quinoline and pyridine; ketones such as acetone, methyl ethyl ketone, and cyclohexanone; esters such as methyl acetate and methyl acrylate; amines such as diethylene triamine and N,N-dimethylaminopropylamine; ethers such as diethyl ether, propylene oxide, and tetrahydrofuran (THF); amides such as N-methylpyrrolidone (NMP), dimethyl formamide, and dimethyl acetamide; and aprotic polar solvents such as hexamethyl phospharamide and dimethyl sulfoxide.

Examples of the material of the current collector for a positive electrode include metal materials such as aluminum, titanium, tantalum, stainless steel, and nickel, and alloys thereof; and carbon materials such as carbon cloth and carbon paper. Preferred is any metal material, especially aluminum or an alloy thereof.

In the case of a metal material, the current collector may be in the form of metal foil, metal cylinder, metal coil, metal plate, metal film, expanded metal, punched metal, metal foam, or the like. In the case of a carbon material, it may be in the form of carbon plate, carbon film, carbon cylinder, or the like. Preferred among these is a metal film. The film may be in the form of mesh, as appropriate. The film may have any thickness, and the thickness is usually 1 µm or greater, preferably 3 µm or greater, more preferably 5 µm or greater, while usually 1 mm or smaller, preferably 100 µm or smaller, more preferably 50 µm or smaller. The film having a thickness smaller than the above range may have insufficient strength as a current collector. In contrast, the film having a thickness greater than the above range may have poor handleability.

In order to reduce the electric contact resistance between the current collector and the positive electrode active material layer, the current collector also preferably has a conductive aid applied on the surface thereof. Examples of the conductive aid include carbon and noble metals such as gold, platinum, and silver.

The ratio between the thicknesses of the current collector and the positive electrode active material layer may be any value, and the ratio {(thickness of positive electrode active material layer on one side immediately before injection of electrolyte solution)/(thickness of current collector)} is preferably 20 or lower, more preferably 15 or lower, most preferably 10 or lower. The ratio is also preferably 0.5 or higher, more preferably 0.8 or higher, most preferably 1 or higher. The current collector and the positive electrode active material layer showing a ratio higher than the above range may cause the current collector to generate heat due to Joule heating during high-current-density charge and discharge. The current collector and the positive electrode active material layer showing a ratio lower than the above range may cause an increased ratio by volume of the current collector to the positive electrode active material, reducing the battery capacity.

The positive electrode may be produced by a usual method. An example of the production method is a method in which the positive electrode active material is mixed with the aforementioned binder, thickening agent, conductive material, solvent, and other components to form a slurry-like positive electrode mixture, and then this mixture is applied to a current collector, dried, and pressed so as to be densified.

The densification may be achieved using a manual press or a roll press, for example. The density of the positive electrode active material layer is preferably 1.5 g/cm$^3$ or higher, more preferably 2 g/cm$^3$ or higher, still more preferably 2.2 g/cm$^3$ or higher, while preferably 5 g/cm$^3$ or lower, more preferably 4.5 g/cm$^3$ or lower, still more preferably 4 g/cm$^3$ or lower. The positive electrode active material layer having a density higher than the above range may cause low permeability of the electrolyte solution toward the vicinity of the interface between the current collector and the active material, and poor charge and discharge characteristics particularly at a high current density, failing to provide high output. The positive electrode active material layer having a density lower than the above range may cause poor conductivity between the active materials and increase the battery resistance, failing to provide high output.

In order to improve the stability at high output and high temperature in the case of using the electrolyte solution of the invention, the area of the positive electrode active material layer is preferably large relative to the outer surface area of an external case of the battery. Specifically, the total area of the positive electrode is preferably 15 times or more, more preferably 40 times or more, greater than the surface area of the external case of the secondary battery. For closed, square-shaped cases, the outer surface area of an external case of the battery herein means the total area calculated from the dimensions of length, width, and thickness of the case portion into which a power-generating element is packed except for a protruding portion of a terminal. For closed, cylinder-like cases, the outer surface area of an external case of the battery herein means the geometric surface area of an approximated cylinder of the case portion into which a power-generating element is packed except for a protruding portion of a terminal. The total area of the positive electrode herein means the geometric surface area of the positive electrode mixture layer opposite to a mixture layer including the negative electrode active material. For structures including a current collector foil and positive electrode mixture layers on both sides of the current collector, the total area of the positive electrode is the sum of the areas calculated on the respective sides.

The positive electrode plate may have any thickness. In order to achieve a high capacity and high output, the lower limit of the thickness of the mixture layer on one side of the current collector excluding the thickness of the base metal foil is preferably 10 µm or greater, more preferably 20 µm or greater, while preferably 500 µm or smaller, more preferably 450 µm or smaller.

To a surface of the positive electrode plate may be attached a substance having a composition different from the positive electrode plate. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; carbonates such as lithium carbonate, calcium carbonate, and magnesium carbonate; and carbon.

<Negative Electrode>

The negative electrode includes a negative electrode active material layer containing a negative electrode active material and a current collector.

The negative electrode material may be any one that can electrochemically occlude and release lithium ions. Specific examples thereof include carbon materials, alloyed materials, lithium-containing metal complex oxide materials, and conductive polymers. These may be used alone or two or more thereof may be used in any combination.

Examples of the negative electrode active material include carbonaceous materials that can occlude and release lithium such as pyrolysates of organic matter under various pyrolysis conditions, artificial graphite, and natural graphite; metal oxide materials that can occlude and release lithium such as tin oxide and silicon oxide; lithium metals; various lithium alloys; and lithium-containing metal complex oxide materials. Two or more of these negative electrode active materials may be used in admixture with each other.

The carbonaceous material that can occlude and release lithium is preferably artificial graphite produced by high-temperature treatment of easily graphitizable pitch from various materials, purified natural graphite, or a material obtained by surface treatment on such graphite with pitch or other organic matter and then carbonization of the surface-treated graphite. In order to achieve a good balance between the initial irreversible capacity and the high-current-density charge and discharge characteristics, the carbonaceous material is more preferably selected from carbonaceous materials obtained by heat-treating natural graphite, artificial graphite, artificial carbonaceous substances, or artificial graphite substances at 400° C. to 3200° C. once or more; carbonaceous materials which allow the negative electrode active material layer to include at least two or more carbonaceous matters having different crystallinities and/or have an interface between the carbonaceous matters having the different crystallinities; and carbonaceous materials which allow the negative electrode active material layer to have an interface between at least two or more carbonaceous matters having different orientations. These carbonaceous materials may be used alone or in any combination of two or more at any ratio.

Examples of the carbonaceous materials obtained by heat-treating artificial carbonaceous substances or artificial graphite substances at 400° C. to 3200° C. once or more include coal-based coke, petroleum-based coke, coal-based pitch, petroleum-based pitch, and those prepared by oxidizing these pitches; needle coke, pitch coke, and carbon materials prepared by partially graphitizing these cokes; pyrolysates of organic matter such as furnace black, acetylene black, and pitch-based carbon fibers; carbonizable organic matter and carbides thereof; and solutions prepared by dissolving carbonizable organic matter in a low-molecular-weight organic solvent such as benzene, toluene, xylene, quinoline, or n-hexane, and carbides thereof.

The metal material (excluding lithium-titanium complex oxides) to be used as the negative electrode active material may be any compound that can occlude and release lithium, and examples thereof include simple lithium, simple metals and alloys that constitute lithium alloys, and oxides, carbides, nitrides, silicides, sulfides, and phosphides thereof. The simple metals and alloys constituting lithium alloys are preferably materials containing any of metal and semi-metal elements in Groups 13 and 14, more preferably simple metal of aluminum, silicon, and tin (hereinafter, referred to as "specific metal elements"), and alloys and compounds containing any of these atoms. These materials may be used alone or in combination of two or more at any ratio.

Examples of the negative electrode active material containing at least one atom selected from the specific metal elements include simple metal of any one specific metal element, alloys of two or more specific metal elements, alloys of one or two or more specific metal elements and one or two or more other metal elements, compounds containing one or two or more specific metal elements, and composite compounds such as oxides, carbides, nitrides, silicides, sulfides, and phosphides of the compounds. Such a simple metal, alloy, or metal compound used as the negative electrode active material can lead to a high-capacity battery.

Examples thereof further include compounds in which any of the above composite compounds are complexly bonded with several elements such as simple metals, alloys, and nonmetal elements. Specifically, in the case of silicon or tin, for example, an alloy of this element and a metal that does not serve as a negative electrode may be used. In the case of tin, for example, a composite compound including a combination of 5 or 6 elements, including tin, a metal (excluding silicon) that serves as a negative electrode, a metal that does not serve as a negative electrode, and a nonmetal element, may be used.

Specific examples thereof include simple Si, $SiB_4$, $SiB_6$, $Mg_2Si$, $Ni_2Si$, $TiSi_2$, $MoSi_2$, $CoSi_2$, $NiSi_2$, $CaSi_2$, $CrSi_2$, $Cu_5Si$, $FeSi_2$, $MnSi_2$, $NbSi_2$, $TaSi_2$, $VSi_2$, $WSi_2$, $ZnSi_2$, SiC, $Si_3N_4$, $Si_2N_2O$, $SiO_v$ (0<v≤2), LiSiO, simple tin, $SnSiO_3$, LiSnO, $Mg_2Sn$, and $SnO_w$ (0<w≤2).

Examples thereof further include composite materials of Si or Sn used as a first constitutional element, and second and third constitutional elements. The second constitutional element is at least one selected from cobalt, iron, magnesium, titanium, vanadium, chromium, manganese, nickel, copper, zinc, gallium, and zirconium, for example. The third constitutional element is at least one selected from boron, carbon, aluminum, and phosphorus, for example.

In order to achieve a high battery capacity and excellent battery characteristics, the metal material is preferably simple silicon or tin (which may contain trace impurities), SiOv (0<v≤2), SnOw (0≤w≤2), a Si—Co—C composite material, a Si—Ni—C composite material, a Sn—Co—C composite material, or a Sn—Ni—C composite material.

The lithium-containing metal complex oxide material to be used as the negative electrode active material may be any material that can occlude and release lithium. In order to achieve good high-current-density charge and discharge characteristics, materials containing titanium and lithium are preferred, lithium-containing metal complex oxide materials containing titanium are more preferred, and complex oxides of lithium and titanium (hereinafter, abbreviated as "lithium titanium complex oxides") are still more preferred. In other words, use of a spinel-structured lithium titanium complex oxide in the negative electrode active material for an electrolyte battery is particularly preferred because this can markedly reduce the output resistance.

Preferred examples of the lithium titanium complex oxides include compounds represented by the following formula:

$$Li_xTi_yM_zO_4$$

wherein M is at least one element selected from the group consisting of Na, K, Co, Al, Fe, Ti, Mg, Cr, Ga, Cu, Zn, and Nb.

In order to achieve a good balance of the battery performance, particularly preferred among the above compositions are those satisfying any of the following:
(i) $1.2 \leq x \leq 1.4$, $1.5 \leq y \leq 1.7$, $z=0$
(ii) $0.9 \leq x \leq 1.1$, $1.9 \leq y \leq 2.1$, $z=0$
(iii) $0.7 \leq x \leq 0.9$, $2.1 \leq y \leq 2.3$, $z=0$.

Particularly preferred representative composition of the compound is $Li_{4/3}Ti_{5/3}O_4$ corresponding to the composition (i), $Li_1Ti_2O_4$ corresponding to the composition (ii), and $Li_{4/5}Ti_{11/5}O_4$ corresponding to the composition (iii). Preferred examples of the structure satisfying $Z \neq 0$ include $Li_{4/3}Ti_{4/3}Al_{1/3}O_4$.

The negative electrode mixture preferably further contains a binder, a thickening agent, and a conductive material.

Examples of the binder include the same binders as those mentioned for the positive electrode. The proportion of the binder is preferably 0.1% by mass or more, more preferably 0.5% by mass or more, particularly preferably 0.6% by mass or more, while preferably 20% by mass or less, more preferably 15% by mass or less, still more preferably 10% by mass or less, particularly preferably 8% by mass or less, relative to the negative electrode active material. The binder at a proportion relative to the negative electrode active material higher than the above range may lead to an increased proportion of the binder which fails to contribute to the battery capacity, causing a low battery capacity. The binder at a proportion lower than the above range may cause lowered strength of the negative electrode.

In particular, in the case of using a rubbery polymer typified by SBR as a main component, the proportion of the binder is usually 0.1% by mass or more, preferably 0.5% by mass or more, more preferably 0.6% by mass or more, while usually 5% by mass or less, preferably 3% by mass or less, more preferably 2% by mass or less, relative to the negative electrode active material. In the case of using a fluoropolymer typified by polyvinylidene fluoride as a main component, the proportion of the binder is usually 1% by mass or more, preferably 2% by mass or more, more preferably 3% by mass or more, while usually 15% by mass or less, preferably 10% by mass or less, more preferably 8% by mass or less, relative to the negative electrode active material.

Examples of the thickening agent include the same thickening agents as those mentioned for the positive electrode. The proportion of the thickening agent is usually 0.1% by mass or higher, preferably 0.5% by mass or higher, still more preferably 0.6% by mass or higher, while usually 5% by mass or lower, preferably 3% by mass or lower, still more preferably 2% by mass or lower, relative to the negative electrode active material. The thickening agent at a proportion relative to the negative electrode active material lower than the above range may cause significantly poor easiness of application. The thickening agent at a proportion higher than the above range may cause a small proportion of the negative electrode active material in the negative electrode active material layer, resulting in a low capacity of the battery and high resistance between the negative electrode active materials.

Examples of the conductive material of the negative electrode include metal materials such as copper and nickel; and carbon materials such as graphite and carbon black.

The solvent for forming slurry may be any solvent that can dissolve or disperse the negative electrode active material and the binder, as well as a thickening agent and a conductive material used as appropriate. The solvent may be either an aqueous solvent or an organic solvent.

Examples of the aqueous solvent include water and alcohols. Examples of the organic solvent include N-methylpyrrolidone (NMP), dimethyl formamide, dimethyl acetamide, methyl ethyl ketone, cyclohexanone, methyl acetate, methyl acrylate, diethyl triamine, N,N-dimethyl aminopropyl amine, tetrahydrofuran (THF), toluene, acetone, diethyl ether, dimethyl acetamide, hexamethyl phospharamide, dimethyl sulfoxide, benzene, xylene, quinoline, pyridine, methyl naphthalene, and hexane.

Examples of the material of the current collector for a negative electrode include copper, nickel, and stainless steel. In order to easily process the material into a film and to minimize the cost, copper foil is preferred.

The current collector usually has a thickness of 1 μm or greater, preferably 5 μm or greater, while usually 100 μm or smaller, preferably 50 μm or smaller. Too thick a negative electrode current collector may cause an excessive reduction in capacity of the whole battery, while too thin a current collector may be difficult to handle.

The negative electrode may be produced by a usual method. An example of the production method is a method in which the negative electrode material is mixed with the aforementioned binder, thickening agent, conductive material, solvent, and other components to form a slurry-like mixture, and then this mixture is applied to a current collector, dried, and pressed so as to be densified. In the case of using an alloyed material, a thin film layer containing the above negative electrode active material (negative electrode active material layer) may be produced by vapor deposition, sputtering, plating, or the like.

The electrode formed from the negative electrode active material may have any structure. The negative electrode active material existing on the current collector preferably has a density of 1 $g \cdot cm^{-3}$ or higher, more preferably 1.2 $g \cdot cm^{-3}$ or higher, particularly preferably 1.3 $g \cdot cm^{-3}$ or higher, while preferably 2.2 $g \cdot cm^{-3}$ or lower, more preferably 2.1 $g \cdot cm^{-3}$ or lower, still more preferably 2.0 $g \cdot cm^{-3}$ or lower, particularly preferably 1.9 $g \cdot cm^{-3}$ or lower. The negative electrode active material existing on the current collector having a density higher than the above range may cause destruction of the negative electrode active material particles, resulting in a high initial irreversible capacity and poor high-current-density charge and discharge characteristics due to reduction in permeability of the electrolyte solution toward the vicinity of the interface between the current collector and the negative electrode active material. The negative electrode active material having a density below the above range may cause poor conductivity between the negative electrode active materials, high battery resistance, and a low capacity per unit volume.

The thickness of the negative electrode plate is a design matter in accordance with the positive electrode plate to be used, and may be any value. The thickness of the mixture layer excluding the thickness of the base metal foil is usually 15 μm or greater, preferably 20 μm or greater, more preferably 30 μm or greater, while usually 300 μm or smaller, preferably 280 μm or smaller, more preferably 250 μm or smaller.

To a surface of the negative electrode plate may be attached a substance having a composition different from the negative electrode plate. Examples of the substance attached to the surface include oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; and carbonates such as lithium carbonate, calcium carbonate, and magnesium carbonate.

<Separator>

The lithium ion secondary battery of the invention preferably further includes a separator.

The separator may be formed from any known material and may have any known shape as long as the resulting separator is stable to the electrolyte solution and is excellent in a liquid-retaining ability. The separator is preferably in the form of a porous sheet or a nonwoven fabric which is formed from a material stable to the electrolyte solution of the invention, such as resin, glass fiber, or inorganic matter, and which has an excellent liquid-retaining ability.

Examples of the material of a resin or glass-fiber separator include polyolefins such as polyethylene and polypropylene, aromatic polyamide, polytetrafluoroethylene, polyether sulfone, and glass filters. These materials may be used alone or in any combination of two or more at any ratio, for example, in the form of a polypropylene/polyethylene bilayer film or a polypropylene/polyethylene/polypropylene trilayer film. In order to achieve good permeability of the electrolyte solution and a good shut-down effect, the separator is preferably a porous sheet or a nonwoven fabric formed from a polyolefin such as polyethylene or polypropylene.

The separator may have any thickness, and the thickness is usually 1 μm or greater, preferably 5 μm or greater, more preferably 8 μm or greater, while usually 50 μm or smaller, preferably 40 μm or smaller, more preferably 30 μm or smaller. The separator thinner than the above range may have poor insulation and mechanical strength. The separator thicker than the above range may cause not only poor battery performance such as poor rate characteristics but also a low energy density of the whole electrolyte battery.

The separator which is a porous one such as a porous sheet or a nonwoven fabric may have any porosity. The porosity is usually 20% or higher, preferably 35% or higher, more preferably 45% or higher, while usually 90% or lower, preferably 85% or lower, more preferably 75% or lower. The separator having a porosity lower than the above range tends to have high film resistance, causing poor rate characteristics. The separator having a porosity higher than the above range tends to have low mechanical strength, causing poor insulation.

The separator may also have any average pore size. The average pore size is usually 0.5 μm or smaller, preferably 0.2 μm or smaller, while usually 0.05 μm or larger. The separator having an average pore size larger than the above range may easily cause short circuits. The separator having an average pore size smaller than the above range may have high film resistance, causing poor rate characteristics.

Examples of the inorganic matter include oxides such as alumina and silicon dioxide, nitrides such as aluminum nitride and silicon nitride, and sulfates such as barium sulfate and calcium sulfate, each in the form of particles or fibers.

The separator is in the form of a thin film such as a nonwoven fabric, a woven fabric, or a microporous film. The thin film favorably has a pore size of 0.01 to 1 μm and a thickness of 5 to 50 μm. Instead of the above separate thin film, the separator may have a structure in which a composite porous layer containing particles of the above inorganic matter is disposed on a surface of one or each of the positive and negative electrodes using a resin binder. For example, alumina particles having a 90% particle size of smaller than 1 μm may be applied to the respective surfaces of the positive electrode with fluororesin used as a binder to form a porous layer.

<Battery Design>

The electrode group may be either a laminate structure including the above positive and negative electrode plates with the above separator in between, or a wound structure including the above positive and negative electrode plates in spiral with the above separator in between. The proportion of the volume of the electrode group in the battery internal volume (hereinafter, referred to as an electrode group proportion) is usually 40% or higher, preferably 50% or higher, while usually 90% or lower, preferably 80% or lower.

The electrode group proportion lower than the above range may cause a low battery capacity. The electrode group proportion higher than the above range may cause small void space in the battery. Thus, if the battery temperature rises to high temperature and thereby the components swell and the liquid fraction of the electrolyte solution exhibits high vapor pressure to raise the internal pressure, the battery characteristics such as charge and discharge repeatability and high-temperature storageability may be impaired and a gas-releasing valve for releasing the internal pressure toward the outside may be actuated.

The current collecting structure may be any structure. In order to more effectively improve the high-current-density charge and discharge performance by the electrolyte solution of the invention, the current collecting structure is preferably a structure which reduces the resistances at wiring portions and jointing portions. Such reduction in internal resistance can particularly favorably lead to the effects achieved with the electrolyte solution of the invention.

In an electrode group having the laminate structure, the metal core portions of the respective electrode layers are preferably bundled and welded to a terminal. If an electrode has a large area, the internal resistance is high. Thus, multiple terminals may preferably be disposed in the electrode so as to reduce the resistance. In an electrode group having the wound structure, multiple lead structures may be disposed on each of the positive electrode and the negative electrode and bundled to a terminal. This can reduce the internal resistance.

The external case may be made of any material that is stable to an electrolyte solution to be used. Specific examples thereof include metals such as nickel-plated steel plates, stainless steel, aluminum and aluminum alloys, and magnesium alloys, and a layered film (laminate film) of resin and aluminum foil. In order to reduce the weight, a metal such as aluminum or an aluminum alloy or a laminate film is favorably used.

An external case made of metal may have a sealed-up structure formed by welding the metal by laser welding, resistance welding, or ultrasonic welding, or a caulking structure using the metal with a resin gasket in between. An external case made of a laminate film may have a sealed-up structure formed by hot-melting resin layers. In order to improve the sealability, a resin which is different from the resin of the laminate film may be disposed between the resin layers. Especially, in the case of forming a sealed-up structure by hot-melting the resin layers with current collecting terminals in between, metal and resin are to be bonded. Thus, the resin to be disposed between the resin layers is favorably a resin having a polar group or a modified resin having a polar group introduced therein.

The lithium ion secondary battery of the invention may have any shape, such as a cylindrical shape, a square shape, a laminate shape, a coin shape, or a large-size shape. The shapes and the structures of the positive electrode, the negative electrode, and the separator may be changed in accordance with the shape of the battery.

A module including the lithium ion secondary battery of the invention is also one aspect of the invention.

In a preferred embodiment, the lithium ion secondary battery includes a positive electrode, a negative electrode, and the aforementioned electrolyte solution, the positive electrode including a positive electrode current collector and a positive electrode active material layer containing a positive electrode active material, the positive electrode active material containing Mn. The lithium ion secondary battery including a positive electrode active material layer that contains a positive electrode active material containing Mn can have much better high-temperature storage characteristics.

In order to provide a high-power lithium ion secondary battery having a high energy density, preferred as the positive electrode active material containing Mn are $LiMn_{1.5}Ni_{0.5}O_4$, $LiNi_{0.5}Co_{0.2}Mn_{0.3}O_2$, and $LiNi_{0.6}Co_{0.2}Mn_{0.2}O_2$.

The amount of the positive electrode active material in the positive electrode active material layer is preferably 80% by mass or more, more preferably 82% by mass or more, particularly preferably 84% by mass or more. The upper limit of the amount thereof is preferably 99% by mass or less, more preferably 98% by mass or less. Too small an amount of the positive electrode active material in the positive electrode active material layer may lead to an insufficient electric capacity. In contrast, too large an amount thereof may lead to insufficient strength of the positive electrode.

The positive electrode active material layer may further contain a conductive material, a thickening agent, and a binder.

The binder may be any material that is safe against a solvent to be used in production of electrodes and the electrolyte solution. Examples thereof include polyvinylidene fluoride, polytetrafluoroethylene, polyethylene, polypropylene, SBR (styrene-butadiene rubber), isoprene rubber, butadiene rubber, ethylene-acrylic acid copolymers, ethylene-methacrylic acid copolymers, polyethylene terephthalate, polymethyl methacrylate, polyimide, aromatic polyamide, cellulose, nitro cellulose, NBR (acrylonitrile-butadiene rubber), fluoroelastomer, ethylene-propylene rubber, styrene-butadiene-styrene block copolymers and hydrogenated products thereof, EPDM (ethylene-propylene-diene terpolymers), styrene-ethylene-butadiene-ethylene copolymers, styrene-isoprene-styrene block copolymers and hydrogenated products thereof, syndiotactic-1,2-polybutadiene, polyvinyl acetate, ethylene-vinyl acetate copolymers, propylene-α-olefin copolymers, fluorinated polyvinylidene fluoride, tetrafluoroethylene-ethylene copolymers, and polymer compositions having ion conductivity of alkali metal ions (especially, lithium ions). These substances may be used alone or in any combination of two or more at any ratio.

The amount of the binder, which is expressed as the proportion of the binder in the positive electrode active material layer, is usually 0.1% by mass or more, preferably 1% by mass or more, more preferably 1.5% by mass or more. The proportion is also usually 80% by mass or less, preferably 60% by mass or less, still more preferably 40% by mass or less, most preferably 10% by mass or less. Too low a proportion of the binder may fail to sufficiently hold the positive electrode active material and cause insufficient mechanical strength of the positive electrode, impairing the battery performance such as cycle characteristics. In contrast, too high a proportion thereof may cause reduction in battery capacity and conductivity.

Examples of the thickening agent include carboxymethyl cellulose, methyl cellulose, hydroxymethyl cellulose, ethyl cellulose, polyvinyl alcohol, oxidized starch, monostarch phosphate, casein, and salts thereof. These agents may be used alone or in any combination of two or more at any ratio.

The proportion of the thickening agent relative to the active material is usually 0.1% by mass or higher, preferably 0.2% by mass or higher, more preferably 0.3% by mass or higher, while usually 5% by mass or lower, preferably 3% by mass or lower, more preferably 2% by mass or lower. The thickening agent at a proportion lower than the above range may cause significantly poor easiness of application. The thickening agent at a proportion higher than the above range may cause a low proportion of the active material in the positive electrode active material layer, resulting in a low capacity of the battery and high resistance between the positive electrode active materials.

The conductive material may be any known conductive material. Specific examples thereof include metal materials such as copper and nickel, and carbon materials such as graphite, including natural graphite and artificial graphite, carbon black, including acetylene black, and amorphous carbon, including needle coke. These materials may be used alone or in any combination of two or more at any ratio. The conductive material is used in an amount of usually 0.01% by mass or more, preferably 0.1% by mass or more, more preferably 1% by mass or more, while usually 50% by mass or less, preferably 30% by mass or less, more preferably 15% by mass or less, in the positive electrode active material layer. The conductive material in an amount less than the above range may cause insufficient conductivity. In contrast, conductive material in an amount more than the above range may cause a low battery capacity.

In order to further improve the high-temperature storage characteristics, the positive electrode current collector is preferably formed from a valve metal or an alloy thereof. Examples of the valve metal include aluminum, titanium, tantalum, and chromium. The positive electrode current collector is more preferably formed from aluminum or an alloy of aluminum.

In order to further improve the high-temperature storage characteristics of the lithium ion secondary battery, a portion in contact with the electrolyte solution among portions electrically coupled with the positive electrode current collector is also preferably formed from a valve metal or an alloy thereof. In particular, the external case of the battery and a portion that is electrically coupled with the positive electrode current collector and is in contact with the non-aqueous electrolyte solution among components accommodated in the external case of the battery, such as leads and a safety valve, are preferably formed from a valve metal or an alloy thereof. Stainless steel coated with a valve metal or an alloy thereof may also be used.

The positive electrode may be produced by the aforementioned method. An example of the production method is a method in which the positive electrode active material is mixed with the aforementioned binder, thickening agent, conductive material, solvent, and other components to form a slurry-like positive electrode mixture, and then this mixture is applied to a positive electrode current collector, dried, and pressed so as to be densified.

The structure of the negative electrode is as described above.

The electric double-layer capacitor may include a positive electrode, a negative electrode, and the aforementioned electrolyte solution.

At least one selected from the positive electrode and the negative electrode is a polarizable electrode in the electric double-layer capacitor. Examples of the polarizable electrode and a non-polarizable electrode include the following electrodes specifically disclosed in JP H09-7896 A.

The polarizable electrode mainly containing activated carbon to be used in the invention preferably contains inactivated carbon having a large specific surface area and a conductive material, such as carbon black, providing electronic conductivity. The polarizable electrode may be formed by a variety of methods. For example, a polarizable electrode including activated carbon and carbon black can be produced by mixing activated carbon powder, carbon black, and phenolic resin, press-molding the mixture, and then sintering and activating the mixture in an inert gas atmosphere and water vapor atmosphere. Preferably, this polarizable electrode is bonded to a current collector using a conductive adhesive, for example.

Alternatively, a polarizable electrode can also be formed by kneading activated carbon powder, carbon black, and a binder in the presence of an alcohol, forming the mixture into a sheet, and then drying the sheet. The binder to be used may be polytetrafluoroethylene, for example. Alternatively, a polarizable electrode integrated with a current collector can be produced by mixing activated carbon powder, carbon black, a binder, and a solvent to form slurry, applying this slurry to metal foil of a current collector, and then drying the slurry.

The electric double-layer capacitor may have polarizable electrodes mainly containing activated carbon as the respective electrodes. Still, the electric double-layer capacitor may have a structure in which a non-polarizable electrode is used on one side. Examples of such a structure include a structure in which a positive electrode mainly containing an electrode active material such as a metal oxide is combined with a polarizable negative electrode mainly containing activated carbon; and a structure in which a negative electrode mainly containing a carbon material that can reversibly occlude and release lithium ions or a negative electrode of lithium metal or lithium alloy is combined with a polarizable positive electrode mainly containing activated carbon.

In place of or in combination with activated carbon, any carbonaceous material may be used, such as carbon black, graphite, expanded graphite, porous carbon, carbon nanotube, carbon nanohorn, and Ketjenblack.

The non-polarizable electrode is preferably an electrode mainly containing a carbon material that can reversibly occlude and release lithium ions, with this carbon material made to occlude lithium ions in advance. In this case, the electrolyte used is a lithium salt. The electric double-layer capacitor having such a structure can achieve a much higher withstand voltage exceeding 4 V.

The solvent used in preparation of the slurry in production of electrodes is preferably one that dissolves a binder. In accordance with the type of a binder, the solvent is appropriately selected from N-methylpyrrolidone, dimethyl formamide, toluene, xylene, isophorone, methyl ethyl ketone, ethyl acetate, methyl acetate, dimethyl phthalate, ethanol, methanol, butanol, and water.

Examples of the activated carbon used for the polarizable electrode include phenol resin-type activated carbon, coconut shell-type activated carbon, and petroleum coke-type activated carbon. In order to achieve a large capacity, petroleum coke-type activated carbon or phenol resin-type activated carbon is preferably used. Examples of methods of activating the activated carbon include steam activation and molten KOH activation. In order to achieve a larger capacity, activated carbon prepared by molten KOH activation is preferably used.

Preferred examples of the conductive agent used for the polarizable electrode include carbon black, Ketjenblack, acetylene black, natural graphite, artificial graphite, metal fiber, conductive titanium oxide, and ruthenium oxide. In order to achieve good conductivity (i.e., low internal resistance), and because too large an amount thereof may lead to a decreased capacity of the product, the amount of the conductive agent such as carbon black used for the polarizable electrode is preferably 1 to 50% by mass in the sum of the amounts of the activated carbon and the conductive agent.

In order to provide an electric double-layer capacitor having a large capacity and low internal resistance, the activated carbon used for the polarizable electrode preferably has an average particle size of 20 μm or smaller and a specific surface area of 1500 to 3000 $m^2/g$. Preferred examples of the carbon material for providing an electrode mainly containing a carbon material that can reversibly occlude and release lithium ions include natural graphite, artificial graphite, graphitized mesocarbon microsphere, graphitized whisker, vapor-grown carbon fiber, sintered furfuryl alcohol resin, and sintered novolak resin.

The current collector may be any chemically and electrochemically corrosion-resistant one. Preferred examples of the current collector used for the polarizable electrode mainly containing activated carbon include stainless steel, aluminum, titanium, and tantalum. Particularly preferred materials in terms of the characteristics and cost of the resulting electric double-layer capacitor are stainless steel and aluminum. Preferred examples of the current collector used for the electrode mainly containing a carbon material that can reversibly occlude and release lithium ions include stainless steel, copper, and nickel.

Examples of methods of allowing the carbon material that can reversibly occlude and release lithium ions to occlude lithium ions in advance include: (1) a method of mixing powdery lithium to a carbon material that can reversibly occlude and release lithium ions; (2) a method of placing lithium foil on an electrode including a carbon material that can reversibly occlude and release lithium ions and a binder so as to bring the lithium foil to be in electrical contact with the electrode, immersing this electrode in an electrolyte solution containing a lithium salt dissolved therein so as to ionize the lithium, and allowing the carbon material to take in the lithium ions; and (3) a method of placing an electrode including a carbon material that can reversibly occlude and release lithium ions and a binder on the minus side and placing a lithium metal on the plus side, immersing the electrodes in a non-aqueous electrolyte solution containing a lithium salt as an electrolyte, and supplying a current so that the carbon material is allowed to electrochemically take in the ionized lithium.

Examples of known electric double-layer capacitors include wound electric double-layer capacitors, laminated electric double-layer capacitors, and coin-type electric double-layer capacitors. The electric double-layer capacitor may also be any of these types.

For example, a wound electric double-layer capacitor may be assembled as follows. A positive electrode and a negative electrode each of which includes a laminate (electrode) of a current collector and an electrode layer are wound with a separator in between to provide a wound element. This wound element is put into a case made of aluminum, for example. The case is filled with an electrolyte solution, preferably a non-aqueous electrolyte solution, and then sealed with a rubber sealant.

A separator formed from a conventionally known material and having a conventionally known structure may be used. Examples thereof include polyethylene porous membranes, polytetrafluoroethylene, and nonwoven fabric of polypropylene fiber, glass fiber, or cellulose fiber.

In accordance with any known method, the electric double-layer capacitor may be prepared in the form of a laminated electric double-layer capacitor in which sheet-like positive and negative electrodes are stacked with an electrolyte solution and a separator in between or a coin-type electric double-layer capacitor in which positive and negative electrodes are fixed in a coin shape by a gasket with an electrolyte solution and a separator in between.

The electrolyte solution of the invention is useful as an electrolyte solution for large-size lithium ion secondary batteries for hybrid vehicles or distributed generation, and for electric double-layer capacitors.

EXAMPLES

The invention is described with reference to examples, but the invention is not intended to be limited by these examples.

Synthesis Example 1

Production of bis(4,4,5,5,5-pentafluoro-2-pentenyl)oxalate

A reaction container purged with nitrogen was charged with oxalyl dichloride (2.0 g, 15.8 mmol) and 30 mL of methylene chloride. Thereto was added dropwise 4,4,5,5,5-pentafluoro-2-penten-1-ol (5.5 g, 31.5 mmol, (E) isomer:(Z) isomer=1:1) at 0° C., followed by dropwise addition of a solution of pyridine (3.0 g, 37.8 mmol) in 10 mL of methylene chloride. This solution was stirred at room temperature for five hours. The reaction solution was filtered through celite and the residue was washed with methylene chloride. The resulting filtrate was washed with 1N hydrochloric acid, then with water, dried, and concentrated, whereby the target bis(4,4,5,5,5-pentafluoro-2-pentenyl)oxalate (4.0 g, 9.8 mmol, yield: 62%, mixture of (E), (E) isomer:(E), (Z) isomer:(Z), (Z) isomer) was obtained.

Synthesis Example 2

Production of bis(2-fluoro-2-propenyl)oxalate

A reaction container purged with nitrogen was charged with oxalyl dichloride (2.0 g, 15.8 mmol) and 30 mL of methylene chloride. Thereto was added dropwise 2-fluoro-2-propen-1-ol (2.4 g, 31.5 mmol) at 0° C., followed by dropwise addition of a solution of pyridine (3.0 g, 37.8 mmol) in 10 mL of methylene chloride. This solution was stirred at room temperature for five hours. The reaction solution was filtered through celite and the residue was washed with methylene chloride. The resulting filtrate was washed with 1N hydrochloric acid, then with water, dried, and concentrated, whereby the target bis(2-fluoro-2-propenyl)oxalate (2.1 g, 10.2 mmol, yield: 64%) was obtained.

Synthesis Example 3

Production of bis(4,4,4-trifluoro-2-butenyl)oxalate

A reaction container purged with nitrogen was charged with oxalyl dichloride (2.0 g, 15.8 mmol) and 30 mL of methylene chloride. Thereto was added dropwise 4,4,4-trifluoro-2-buten-1-ol (4.0 g, 31.5 mmol, (E) isomer:(Z) isomer=1:1) at 0° C., followed by dropwise addition of a solution of pyridine (3.0 g, 37.8 mmol) in 10 mL of methylene chloride. This solution was stirred at room temperature for five hours. The reaction solution was filtered through celite and the residue was washed with methylene chloride. The resulting filtrate was washed with 1N hydrochloric acid, then with water, dried, and concentrated, whereby the target bis(4,4,4-trifluoro-2-butenyl)oxalate (3.6 g, 11.8 mmol, yield: 74%, mixture of (E), (E) isomer:(E), (Z) isomer:(Z), (Z) isomer) was obtained.

Synthesis Example 4

Production of 4,4,5,5,5-pentafluoro-2-pentenyl methyl oxalate

A reaction container purged with nitrogen was charged with methyloxalyl chloride (2.0 g, 16.3 mmol) and 30 mL of methylene chloride. Thereto was added dropwise 4,4,5,5,5-pentafluoro-2-penten-1-ol (2.9 g, 16.3 mmol, (E) isomer:(Z) isomer=1:1) at 0° C., followed by dropwise addition of a solution of pyridine (1.6 g, 19.6 mmol) in 10 mL of methylene chloride. This solution was stirred at room temperature for five hours. The reaction solution was filtered through celite and the residue was washed with methylene chloride. The resulting filtrate was washed with 1N hydrochloric acid, then with water, dried, and concentrated, whereby the target 4,4,5,5,5-pentafluoro-2-pentenyl methyl oxalate (3.7 g, 14.1 mmol, yield: 87%, mixture of (E) isomer:(Z) isomer) was obtained.

Synthesis Example 5

Production of methyl 2-fluoro-2-propenyl oxalate

A reaction container purged with nitrogen was charged with methyloxalyl chloride (2.0 g, 16.3 mmol) and 30 mL of methylene chloride. Thereto was added dropwise 2-fluoro-2-propen-1-ol (1.2 g, 16.3 mmol) at 0° C., followed by dropwise addition of a solution of pyridine (1.6 g, 19.6 mmol) in 10 mL of methylene chloride. This solution was stirred at room temperature for five hours. The reaction solution was filtered through celite and the residue was washed with methylene chloride. The resulting filtrate was washed with 1N hydrochloric acid, then with water, dried, and concentrated, whereby the target methyl 2-fluoro-2-propenyl oxalate (2.0 g, 12.3 mmol, yield: 76%) was obtained.

Synthesis Example 6

Production of 4,4,4-trifluoro-2-butenyl methyl oxalate

A reaction container purged with nitrogen was charged with methyloxalyl chloride (2.0 g, 16.3 mmol) and 30 mL of methylene chloride. Thereto was added dropwise 4,4,4-trifluoro-2-buten-1-ol (2.1 g, 16.3 mmol, (E) isomer:(Z) isomer=1:1) at 0° C., followed by dropwise addition of a solution of pyridine (1.6 g, 19.6 mmol) in 10 mL of methylene chloride. This solution was stirred at room temperature for five hours. The reaction solution was filtered through celite and the residue was washed with methylene chloride. The resulting filtrate was washed with 1N hydrochloric acid, then with water, dried, and concentrated, whereby the target 4,4,4-trifluoro-2-butenyl methyl oxalate (2.2 g, 10.6 mmol, yield: 65%, mixture of (E) isomer:(Z) isomer) was obtained.

Synthesis Example 7

Production of 2,2,3,3,3-pentafluoropropyl phenyl oxalate

A 30-mL flask was charged with 1 g (5.42 mmol) of phenyl oxalyl chloride and 10 mL of carbon tetrachloride. Thereto was added 825 mg (5.50 mmol) of 2,2,3,3,3-pentafluoro-1-propanol. Then, 550 mg (5.50 mmol) of triethylamine was added dropwise under ice cooling and stirring. After completion of the dropwise addition, the reaction temperature was returned to room temperature and the system was further stirred overnight. Then, the reaction was completed. After completion of the reaction, the reaction solution was mixed with 5 mL of carbon tetrachloride and the mixture was washed with a 10% HCl aqueous solution (10 mL), pure water (10 mL), and saturated saline water (10 mL). An organic layer was collected and concentrated under reduced pressure, whereby 686 mg of the target 2,2,3,3,3-pentafluoropropyl phenyl oxalate was obtained at a yield of 51%.

Synthesis Example 8

Production of 2,2,2-trifluoroethyl phenyl oxalate

A 30-mL flask was charged with 1 g (5.42 mmol) of phenyl oxalyl chloride and 10 mL of carbon tetrachloride. Thereto was added 550 mg (5.50 mmol) of 2,2,2-trifluoroethanol. Then, 550 mg (5.50 mmol) of triethylamine was added dropwise under ice cooling and stirring. After completion of the dropwise addition, the reaction temperature was returned to room temperature and the system was further stirred overnight. Then, the reaction was completed. After completion of the reaction, the reaction solution was mixed with 5 mL of carbon tetrachloride and the mixture was washed with a 10% HCl aqueous solution (10 mL), pure water (10 mL), and saturated saline water (10 mL). An organic layer was collected and concentrated under reduced pressure, whereby 726 mg of the target 2,2,2-trifluoroethyl phenyl oxalate was obtained at a yield of 45%.

Preparation of Electrolyte Solution

Examples 1 to 8

$LiPF_6$ was added to a mixture of ethylene carbonate (EC) and ethyl methyl carbonate (EMC) (volume ratio=30:70) such that the concentration was 1.0 mol/L, whereby a fundamental electrolyte solution was prepared. This electrolyte solution was mixed with bis(4,4,5,5,5-pentafluoro-2-pentenyl)oxalate in an amount shown in Table 1, whereby a non-aqueous electrolyte solution was obtained. Each amount of the compound added shown in the tables indicates the proportion relative to the electrolyte solution finally obtained.

Example 9

A non-aqueous electrolyte solution was obtained as in Example 4, except that bis(2-fluoro-2-propenyl)oxalate was added instead of bis(4,4,5,5,5-pentafluoro-2-pentenyl)oxalate.

Example 10

A non-aqueous electrolyte solution was obtained as in Example 4, except that bis(4,4,4-trifluoro-2-butenyl)oxalate was added instead of bis(4,4,5,5,5-pentafluoro-2-pentenyl)oxalate.

Example 11

A non-aqueous electrolyte solution was obtained as in Example 4, except that methyl 4,4,5,5,5-pentafluoro-2-pentenyl oxalate was added instead of bis(4,4,5,5,5-pentafluoro-2-pentenyl)oxalate.

Example 12

A non-aqueous electrolyte solution was obtained as in Example 4, except that methyl 2-fluoro-2-propenyl oxalate was added instead of bis(4,4,5,5,5-pentafluoro-2-pentenyl)oxalate.

Example 13

A non-aqueous electrolyte solution was obtained as in Example 4, except that 4,4,4-trifluoro-2-butenyl methyl oxalate was added instead of bis(4,4,5,5,5-pentafluoro-2-pentenyl)oxalate.

Example 14

A non-aqueous electrolyte solution was obtained as in Example 4, except that 2,2,3,3,3-pentafluoropropyl phenyl oxalate was added instead of bis(4,4,5,5,5-pentafluoro-2-pentenyl)oxalate.

Example 15

A non-aqueous electrolyte solution was obtained as in Example 4, except that 2,2,2-trifluoroethyl phenyl oxalate was added instead of bis(4,4,5,5,5-pentafluoro-2-pentenyl)oxalate.

Example 16

$LiPF_6$ was added to a mixture of ethylene carbonate (EC) and dimethyl carbonate (DMC) (volume ratio=30:70) such that the concentration was 1.0 mol/L. This electrolyte solution was further mixed with bis(4,4,5,5,5-pentafluoro-2-pentenyl)oxalate in an amount shown in Table 1, whereby a non-aqueous electrolyte solution was obtained.

Example 17

$LiPF_6$ was added to a mixture of ethylene carbonate (EC) and ethyl propionate (EP) (volume ratio=30:70) such that the concentration was 1.0 mol/L. This electrolyte solution was further mixed with bis(4,4,5,5,5-pentafluoro-2-pentenyl)oxalate in an amount shown in Table 1, whereby a non-aqueous electrolyte solution was obtained.

Comparative Example 1

A non-aqueous electrolyte solution was obtained as in Example 1, except that bis(4,4,5,5-pentafluoro-2-pentenyl)oxalate was not added.

Comparative Example 2

A non-aqueous electrolyte solution was obtained as in Example 4, except that diethyl oxalate was added instead of bis(4,4,5,5-pentafluoro-2-pentenyl)oxalate.

(Production of Aluminum Laminate-Type Lithium Ion Secondary Battery)
[Production of Positive Electrode]

First, 90% by mass of $Li(Ni_{1/3}Mn_{1/3}Co_{1/3})O_2$ serving as a positive electrode active material, 5% by mass of acetylene black serving as a conductive material, and 5% by mass of polyvinylidene fluoride (PVdF) serving as a binding agent were mixed in a N-methylpyrrolidone solvent to form slurry. The resulting slurry was applied to one surface of 15-μm-thick aluminum foil with a conductive aid applied thereto in advance, and dried. The workpiece was then roll-pressed using a press and cut to provide a piece including an active material layer having a width of 50 mm and a length of 30 mm and an uncoated portion having a width of 5 mm and a length of 9 mm. This piece was used as a positive electrode.

[Production of Negative Electrode]

First, 98 parts by mass of a carbonaceous material (graphite) was mixed with 1 part by mass of an aqueous dispersion of sodium carboxymethyl cellulose (concentration of sodium carboxymethyl cellulose: 1% by mass) and 1 part by mass of an aqueous dispersion of styrene-butadiene rubber (concentration of styrene-butadiene rubber: 50% by mass) respectively serving as a thickening agent and a binder. The components were mixed using a disperser to form slurry. The resulting slurry was applied to 10-μm-thick copper foil and dried. The workpiece was rolled using a press and cut to provide a piece including an active material layer having a width of 52 mm and a length of 32 mm and an uncoated portion having a width of 5 mm and a length of 9 mm. This piece was used as a negative electrode.

[Production of Aluminum Laminate Cell]

The above positive electrode and negative electrode were placed to face each other with a 20-μm-thick porous polyethylene film (separator) in between. The non-aqueous electrolyte solution prepared above was filled thereinto and the non-aqueous electrolyte solution was made to sufficiently permeate into the components such as the separator. The workpiece was then sealed, pre-charged, and aged, whereby a lithium ion secondary battery was produced.

(Analysis of Battery Characteristics)
[Evaluation of Initial Characteristics]

The lithium ion secondary battery produced above in a state of being sandwiched and pressed between plates was charged to 4.2 V at a constant current corresponding to 0.2 C at 25° C., and then discharged to 3.0 V at a constant current of 0.2 C. This cycle was performed twice so that the battery was stabilized. In the third cycle, the battery was charged to 4.2 V at a constant current of 0.2 C, then charged at a constant voltage of 4.2 V until the current value reached 0.05 C, followed by discharge to 3.0 V at a constant current of 0.2 C. In the fourth cycle, the battery was charged to 4.2 V at a constant current of 0.2 C, then charged at a constant voltage of 4.2 V until the current value reached 0.05 C, followed by discharge to 3.0 V at a constant current of 0.2 C. Thereby, the initial discharge capacity was determined. The battery was then charged to 4.2 V at a constant current of 0.2 C and charged to a current value of 0.05 C at a constant voltage of 4.2 V. Here, 1 C means the current value at which the reference capacity of the battery is discharged in one hour. For example, 5 C means five times this current value, 0.1 C means 1/10 of this current value, and 0.2 C means 1/5 of this current value.

[High-Temperature Storage Test]

The battery after the evaluation of initial characteristics was subjected to high-temperature storage at 85° C. for 36 hours. The battery was then discharged to 3 V at 0.5 C and at 25° C. The residual capacity after high-temperature storage was determined and the capacity retention (%) was determined by the following formula.

(Residual capacity)/(Initial discharge capacity)×100=Capacity retention(%)

The results are shown in Table 1.

[High-Temperature Cycle Test]

The lithium ion secondary battery produced above in a state of being sandwiched and pressurized between plates was subjected to constant current/constant voltage charge (hereinafter, referred to as CC/CV charge) (0.1 C cut off) to 4.2 V at a current corresponding to 1 C and at 60° C., and then discharged to 3 V at a constant current of 1 C. This was counted as one cycle, and the discharge capacity at the third cycle was used to determine the initial discharge capacity. Here, 1 C means the current value at which the reference capacity of the battery is discharged in one hour. For example, 0.2 C means 1/5 of this current value. The cycles were again performed, and the discharge capacity after the 200th cycle was determined. The ratio of the discharge capacity after the 200th cycle to the initial discharge capacity was determined. This value was defined as the cycle capacity retention (%).

(Discharge capacity after 200th cycle)/(Initial discharge capacity)×100=Capacity retention(%)

The results are shown in Table 1.

Preparation of Electrolyte Solution

Example 18

$LiPF_6$ was added to a mixture of ethylene carbonate (EC) and ethyl methyl carbonate (EMC) (volume ratio=30:70) such that the concentration was 1.2 mol/L, whereby a fundamental electrolyte solution was prepared. This electrolyte solution was mixed with bis(4,4,5,5-pentafluoro-2-pentenyl)oxalate and vinylene carbonate (VC) in amounts shown in Table 2, whereby a non-aqueous electrolyte solution was obtained.

Example 19

A non-aqueous electrolyte solution was obtained as in Example 18, except that lithium bis(oxalato)borate (LiBOB) in an amount shown in Table 2 was added instead of VC.

Example 20

A non-aqueous electrolyte solution was obtained as in Example 18, except that lithium difluorophosphate ($LiPO_2F_2$) in an amount shown in Table 2 was added instead of VC.

Example 21

A non-aqueous electrolyte solution was obtained as in Example 18, except that lithium fluorosulfonate (FSO$_3$Li) in an amount shown in Table 2 was added instead of VC.

Example 22

A non-aqueous electrolyte solution was obtained as in Example 18, except that lithium ethyl sulfate (C$_2$H$_5$OSO$_3$Li) in an amount shown in Table 2 was added instead of VC.

Example 23

A non-aqueous electrolyte solution was obtained as in Example 18, except that fluoroethylene carbonate (FEC) in an amount shown in Table 2 was added instead of VC.

Example 24

A non-aqueous electrolyte solution was obtained as in Example 18, except that 4-(2,2,3,3,3-pentafluoro-propyl)-[1,3]dioxolan-2-one (CF$_3$CF$_2$CH$_2$-EC) in an amount shown in Table 2 was added instead of VC.

Example 25

A non-aqueous electrolyte solution was obtained as in Example 18, except that bis(2-fluoro-2-propenyl)oxalate was added instead of bis(4,4,5,5,5-pentafluoro-2-pentenyl)oxalate.

Example 26

A non-aqueous electrolyte solution was obtained as in Example 18, except that methyl 4,4,5,5,5-pentafluoro-2-pentenyl oxalate was added instead of bis(4,4,5,5,5-pentafluoro-2-pentenyl)oxalate.

Example 27

A non-aqueous electrolyte solution was obtained as in Example 18, except that 2,2,3,3,3-pentafluoropropylphenyl oxalate was added instead of bis(4,4,5,5,5-pentafluoro-2-pentenyl)oxalate.

Comparative Example 3

A non-aqueous electrolyte solution was obtained as in Example 18, except that bis(4,4,5,5,5-pentafluoro-2-pentenyl)oxalate and VC were not added.

Comparative Example 4

A non-aqueous electrolyte solution was obtained as in Example 18, except that diethyl oxalate was added instead of bis(4,4,5,5,5-pentafluoro-2-pentenyl)oxalate.

Comparative Example 5

A non-aqueous electrolyte solution was obtained as in Example 18, except that di(2-propynyl)oxalate was added instead of bis(4,4,5,5,5-pentafluoro-2-pentenyl)oxalate and vinylene carbonate (VC) was added in an amount shown in Table 2.

Comparative Example 6

A non-aqueous electrolyte solution was obtained as in Example 20, except that di(2-propenyl)oxalate was added instead of bis(4,4,5,5,5-pentafluoro-2-pentenyl)oxalate.

(Production of Aluminum Laminate-Type Lithium Ion Secondary Battery)

A lithium ion secondary battery was produced as in Example 1, except that the non-aqueous electrolyte solution of one of Examples 18 to 27 and Comparative Examples 3 to 6 was used.

(Analysis of Battery Characteristics)

[Evaluation of Initial Characteristics]

The lithium secondary battery produced above in a state of being sandwiched and pressed between plates was charged to 4.2 V at a constant current corresponding to 0.2 C at 25° C., and then discharged to 3.0 V at a constant current of 0.2 C. This cycle was performed twice so that the battery was stabilized. In the third cycle, the battery was charged to 4.2 V at a constant current of 0.2 C, then charged at a constant voltage of 4.2 V until the current value reached 0.05 C, followed by discharge to 3.0 V at a constant current of 0.2 C. In the fourth cycle, the battery was charged to 4.2 V at a constant current of 0.2 C, then charged at a constant voltage of 4.2 V until the current value reached 0.05 C, followed by discharge to 3.0 V at a constant current of 0.2 C. Thereby, the initial discharge capacity was determined. The battery was then charged to 4.2 V at a constant current of 0.2 C and charged to a current value of 0.05 C at a constant voltage of 4.2 V, and the initial resistance was measured.

[High-Temperature Storage Test]

The battery after the evaluation of initial characteristics was subjected to high-temperature storage at 85° C. for 36 hours. Thereafter, the battery was sufficiently cooled down, and the volume thereof was measured by the Archimedes' method. Based on the volume change before and after the storage, the amount of gas generated was determined. The battery was then discharged to 3 V at 0.5 C and at 25° C. The residual capacity after the high-temperature storage was measured and the capacity retention (%) was determined by the following formula. The battery was charged to 4.2 V at a constant current of 0.2 C, then charged at a constant voltage of 4.2 V until the current value reached 0.05 C, followed by discharge to 3.0 V at 0.5 C. The battery was then charged to 4.2 V at a constant current of 0.2 C and charged at a constant voltage of 4.2 V until the current value reached 0.05 C. The resistance after the storage was measured and the resistance increase (%) after storage was determined by the following formulas.

(Residual capacity)/(Initial discharge capacity)×100=Capacity retention(%)

(Resistance(Ω) after storage)/(Initial resistance (Ω))×100=Resistance increase(%) after storage.

The results are shown in Table 2.

[High-Temperature Cycle Test]

The lithium ion secondary battery produced above in a state of being sandwiched and pressurized between plates was subjected to constant current/constant voltage charge (hereinafter, referred to as CC/CV charge) (0.1 C cut off) to 4.2 V at a current corresponding to 1 C and at 60° C., and then discharged to 3 V at a constant current of 1 C. This was counted as one cycle, and the discharge capacity at the third cycle was used to determine the initial discharge capacity. Here, 1 C means the current value at which the reference capacity of the battery is discharged in one hour. For example, 0.2 C means ⅕ of this current value. The cycles were again performed, and the discharge capacity after the 200th cycle was determined. The ratio of the discharge capacity after the 200th cycle to the initial discharge capacity was determined. This value was defined as the cycle capacity retention (%).

(Discharge capacity after 200th cycle)/(Initial discharge capacity)×100=Capacity retention(%)

The results are shown in Table 2.

Preparation of Electrolyte Solution

Example 28

LiPF$_6$ was added to a mixture of trifluoropropylene carbonate and methyl 2,2,2-trifluoroethyl carbonate (volume ratio=30:70) such that the concentration was 1.0 mol/L, whereby a fundamental electrolyte solution was prepared. This electrolyte solution was mixed with bis(4,4,5,5,5-pentafluoro-2-pentenyl)oxalate in an amount shown in Table 3, whereby a non-aqueous electrolyte solution was obtained.

Example 29

LiPF$_6$ was added to a mixture of trifluoropropylene carbonate and methyl difluoroacetate (volume ratio=30:70) such that the concentration was 1.0 mol/L, whereby a fundamental electrolyte solution was prepared. This electrolyte solution was mixed with bis(4,4,5,5,5-pentafluoro-2-pentenyl)oxalate in an amount shown in Table 3, whereby a non-aqueous electrolyte solution was obtained.

Example 30

LiPF$_6$ was added to a mixture of fluoroethylene carbonate (FEC) and methyl 2,2,2-trifluoroethyl carbonate (volume ratio=30:70) such that the concentration was 1.0 mol/L, whereby a fundamental electrolyte solution was prepared. This electrolyte solution was mixed with bis(4,4,5,5,5-pentafluoro-2-pentenyl)oxalate in an amount shown in Table 3, whereby a non-aqueous electrolyte solution was obtained.

Example 31

LiPF$_6$ was added to a mixture of fluoroethylene carbonate (FEC) and methyl difluoroacetate (volume ratio=30:70) such that the concentration was 1.0 mol/L, whereby a fundamental electrolyte solution was prepared. This electrolyte solution was mixed with bis(4,4,5,5,5-pentafluoro-2-pentenyl)oxalate in an amount shown in Table 3, whereby a non-aqueous electrolyte solution was obtained.

Example 32

LiPF$_6$ was added to a mixture of fluoroethylene carbonate (FEC) and methyl 3,3,3-trifluoropropionate (volume ratio=30:70) such that the concentration was 1.0 mol/L, whereby a fundamental electrolyte solution was prepared. This electrolyte solution was mixed with bis(4,4,5,5,5-pentafluoro-2-pentenyl)oxalate in an amount shown in Table 3, whereby a non-aqueous electrolyte solution was obtained.

Example 33

A non-aqueous electrolyte solution was obtained as in Example 31, except that bis(2-fluoro-2-propenyl)oxalate was added instead of bis(4,4,5,5,5-pentafluoro-2-pentenyl)oxalate.

Example 34

A non-aqueous electrolyte solution was obtained as in Example 31, except that bis(4,4,4-trifluoro-2-butenyl)oxalate was added instead of bis(4,4,5,5,5-pentafluoro-2-pentenyl)oxalate.

Example 35

A non-aqueous electrolyte solution was obtained as in Example 31, except that methyl 4,4,5,5,5-pentafluoro-2-pentenyl oxalate was added instead of bis(4,4,5,5,5-pentafluoro-2-pentenyl)oxalate.

Example 36

A non-aqueous electrolyte solution was obtained as in Example 31, except that methyl 2-fluoro-2-propenyl oxalate was added instead of bis(4,4,5,5,5-pentafluoro-2-pentenyl)oxalate.

Example 37

A non-aqueous electrolyte solution was obtained as in Example 31, except that 4,4,4-trifluoro-2-butenyl methyl oxalate was added instead of bis(4,4,5,5,5-pentafluoro-2-pentenyl)oxalate.

Example 38

A non-aqueous electrolyte solution was obtained as in Example 31, except that 2,2,3,3,3-pentafluoropropyl phenyl oxalate was added instead of bis(4,4,5,5,5-pentafluoro-2-pentenyl)oxalate.

Comparative Example 7

A non-aqueous electrolyte solution was obtained as in Example 28, except that bis(4,4,5,5,5-pentafluoro-2-pentenyl)oxalate was not added.

Comparative Example 8

A non-aqueous electrolyte solution was obtained as in Example 29, except that bis(4,4,5,5,5-pentafluoro-2-pentenyl)oxalate was not added.

Comparative Example 9

A non-aqueous electrolyte solution was obtained as in Example 30, except that bis(4,4,5,5,5-pentafluoro-2-pentenyl)oxalate was not added.

Comparative Example 10

A non-aqueous electrolyte solution was obtained as in Example 31, except that bis(4,4,5,5,5-pentafluoro-2-pentenyl)oxalate was not added.

Comparative Example 11

A non-aqueous electrolyte solution was obtained as in Example 32, except that bis(4,4,5,5,5-pentafluoro-2-pentenyl)oxalate was not added.

(Production of Aluminum Laminate-Type Lithium Ion Secondary Battery)

A lithium ion secondary battery was produced as in Example 1, except that the non-aqueous electrolyte solution of one of Examples 28 to 38 and Comparative Examples 7 to 11 was used.

(Analysis of Battery Characteristics)

[High-Temperature Cycle Characteristic Test]

The lithium ion secondary battery produced above in a state of being sandwiched and pressurized between plates was subjected to constant current/constant voltage charge (hereinafter, referred to as CC/CV charge) (0.1 C cut off) to 4.35 V at a current corresponding to 1 C and at 60° C., and then discharged to 3 V at a constant current of 1 C. This was counted as one cycle, and the discharge capacity at the third cycle was used to determine the initial discharge capacity. Here, 1 C means the current value at which the reference capacity of the battery is discharged in one hour. For example, 0.2 C means ⅕ of this current value. The cycles were again performed, and the discharge capacity after the 200th cycle was determined. The ratio of the discharge capacity after the 200th cycle to the initial discharge capacity was determined. This value was defined as the cycle capacity retention (%).

(Discharge capacity after 200th cycle)/(Initial discharge capacity)×100=Capacity retention(%)

The results are shown in Table 3.

TABLE 1

| | Type of solvent | Compound (I) added | | Results of high-temperature storage test | Results of high-temperature cycle test |
|---|---|---|---|---|---|
| | | Type | Amount (mass %) | Capacity retention after storage (%) | Cycle capacity retention (%) |
| Example 1 | EC/EMC | 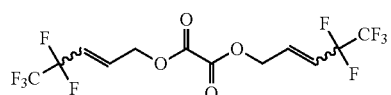 | 0.001 | 84.9 | 89.4 |
| Example 2 | | | 0.01 | 86.5 | 92.9 |
| Example 3 | | | 0.1 | 87.4 | 93.8 |
| Example 4 | | | 1.0 | 87.7 | 94.1 |
| Example 5 | | | 3.0 | 87.9 | 93.7 |
| Example 6 | | | 5.0 | 87.0 | 93.0 |
| Example 7 | | | 10 | 85.9 | 92.7 |
| Example 8 | | | 15 | 84.7 | 89.1 |
| Example 9 | | 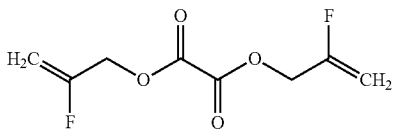 | 1.0 | 86.9 | 93.9 |
| Example 10 | | 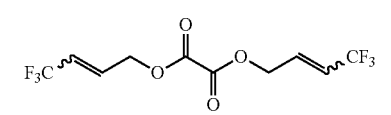 [SMILES: O=C(OCC=CC(F)(F)F)C(=O)OCC=CC(F)(F)F] | 1.0 | 86.8 | 93.8 |
| Example 11 | | 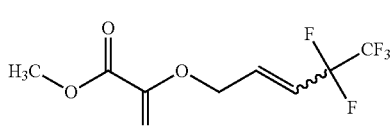 | 1.0 | 86.5 | 93.6 |
| Example 12 | | 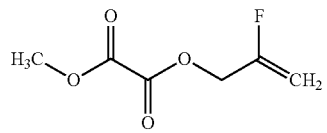 | 1.0 | 86.4 | 93.4 |
| Example 13 | | 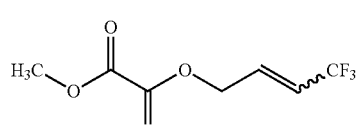 | 1.0 | 86.2 | 93.0 |
| Example 14 | | 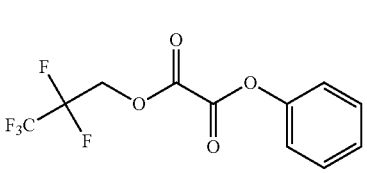 [SMILES: O=C(OCC(F)(F)C(F)(F)F)C(=O)Oc1ccccc1] | 1.0 | 85.9 | 92.9 |

TABLE 1-continued

| | Type of solvent | Compound (I) added Type | Amount (mass %) | Results of high-temperature storage test Capacity retention after storage (%) | Results of high-temperature cycle test Cycle capacity retention (%) |
|---|---|---|---|---|---|
| Example 15 | | 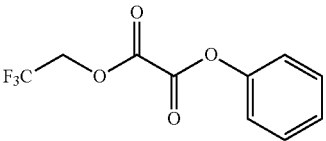 [SMILES: O=C(OCC(F)(F)F)C(=O)Oc1ccccc1] | 1.0 | 85.8 | 92.7 |
| Example 16 | EC/DMC | 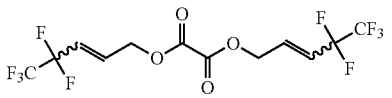 [SMILES: O=C(OCC=CC(F)(F)C(F)(F)F)C(=O)OCC=CC(F)(F)C(F)(F)F] | 1.0 | 87.2 | 93.7 |
| Example 17 | EC/EP | 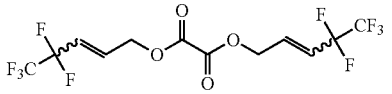 [SMILES: O=C(OCC=CC(F)(F)C(F)(F)F)C(=O)OCC=CC(F)(F)C(F)(F)F] | 1.0 | 87.0 | 92.5 |
| Comparative Example 1 | EC/EMC | None | — | 79.1 | 84.2 |
| Comparative Example 2 | | Diethyl oxalate | 1.0 | 83.4 | 87.5 |

TABLE 2

| | Type of solvent | Compound (I) added Type | Amount (mass %) | Compound (II) added Type | Amount (mass %) | Capacity retention after storage (%) | Resistance increase after storage (relative to value of Comparative Example 1 taken as 1) | Gas increase (relative to value of Comparative Example 1 taken as 1) | Cycle capacity retention (%) |
|---|---|---|---|---|---|---|---|---|---|
| Example 18 | EC/EMC | 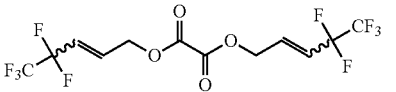 [SMILES: O=C(OCC=CC(F)(F)C(F)(F)F)C(=O)OCC=CC(F)(F)C(F)(F)F] | 1.0 | VC | 0.5 | 89.1 | 0.75 | 0.87 | 95.0 |
| Example 19 | | | | LiBOB | 0.5 | 88.7 | 0.76 | 0.89 | 94.0 |
| Example 20 | | | | LiPO2F2 | 1.0 | 88.8 | 0.72 | 0.84 | 94.2 |
| Example 21 | | | | FSO3Li | 3.0 | 88.7 | 0.71 | 0.86 | 94.3 |
| Example 22 | | | | C2H5OSO3Li | 1.0 | 88.6 | 0.73 | 0.83 | 94.5 |
| Example 23 | | | | FEC | 5.0 | 89.0 | 0.74 | 0.85 | 95.2 |
| Example 24 | | | | CF3CF2CF2-EC | 0.5 | 89.2 | 0.70 | 0.80 | 95.3 |
| Example 25 | | 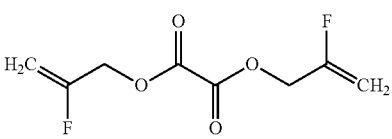 | 1.0 | VC | 0.5 | 88.9 | 0.76 | 0.86 | 94.0 |

TABLE 2-continued

| | | Compound (I) added | | Compound (II) added | | Results of evaluating high-temperature storage characteristics | | | Results of evaluating high-temperature cycle characteristics |
|---|---|---|---|---|---|---|---|---|---|
| | Type of solvent | Type | Amount (mass %) | Type | Amount (mass %) | Capacity retention after storage (%) | Resistance increase after storage (relative to value of Comparative Example 1 taken as 1) | Gas increase (relative to value of Comparative Example 1 taken as 1) | Cycle capacity retention (%) |
| Example 26 | | [H$_3$C–O–C(=O)–C(=O)–O–CH$_2$–CH=CH–CF$_2$–CF$_3$] | 1.0 | VC | 0.5 | 88.7 | 0.74 | 0.89 | 93.9 |
| Example 27 | | [F$_3$C–CF$_2$–CH$_2$–O–C(=O)–C(=O)–O–C$_6$H$_5$] | 1.0 | VC | 0.5 | 88.6 | 0.73 | 0.90 | 93.6 |
| Comparative Example 3 | EC/EMC | None | — | None | — | 79.3 | 1 | 1 | 84.5 |
| Comparative Example 4 | | Diethyl oxalate | 1.0 | VC | 0.5 | 83.9 | 0.97 | 1.68 | 88.0 |
| Comparative Example 5 | | [HC≡C–CH$_2$–O–C(=O)–C(=O)–O–CH$_2$–C≡CH] | 1.0 | VC | 3.0 | 84.5 | 1.25 | 1.60 | 89.0 |
| Comparative Example 6 | | [H$_2$C=CH–CH$_2$–O–C(=O)–C(=O)–O–CH$_2$–CH=CH$_2$] | 1.0 | LiPO2F2 | 1.0 | 84.3 | 0.94 | 1.57 | 88.8 |

TABLE 3

| | | Compound (I) added | | | Results of evaluating Cycle characteristics |
|---|---|---|---|---|---|
| | Type of solvent | Type | | Amount (mass %) | Cycle capacity retention (%) |
| Example 28 | Trifluoropropylene carbonate/methyl 2,2,2-trifluoroethyl carbonate | [F$_3$C–CF$_2$–CH=CH–CH$_2$–O–C(=O)–C(=O)–O–CH$_2$–CH=CH–CF$_2$–CF$_3$] | | 1.0 | 88.1 |
| Example 29 | Trifluoropropylene carbonate/methyl difluoroacetate | | | | 87.6 |
| Example 30 | FEC/methyl 2,2,2-trifluoroethyl carbonate | | | | 87.7 |
| Example 31 | FEC/methyl difluoroacetate | | | | 87.9 |
| Example 32 | FEC/methyl 3,3,3-trifluoropropionate | | | | 87.6 |

TABLE 3-continued

| | | Compound (I) added | | Results of evaluating Cycle characteristics |
|---|---|---|---|---|
| | Type of solvent | Type | Amount (mass %) | Cycle capacity retention (%) |
| Example 33 | FEC/ methyl difluoroacetate | [structure: H2C=CF-CH2-O-C(=O)-C(=O)-O-CH2-CF=CH2] | 1.0 | 87.5 |
| Example 34 | | [structure: F3C-CH=CH-CH2-O-C(=O)-C(=O)-O-CH2-CH=CH-CF3] | 1.0 | 87.4 |
| Example 35 | | [structure: H3C-O-C(=O)-C(=O)-O-CH2-CH=CF-CF3] | 1.0 | 87.2 |
| Example 36 | | [structure: H3C-O-C(=O)-C(=O)-O-CH2-CF=CH2] | 1.0 | 87.0 |
| Example 37 | | [structure: H3C-O-C(=O)-C(=O)-O-CH2-CH=CH-CF3] | 1.0 | 86.9 |
| Example 38 | | [structure: F3C-CF2-CH2-O-C(=O)-C(=O)-O-phenyl] | 1.0 | 86.5 |
| Comparative Example 7 | Trifluoropropylene carbonate/ methyl 2,2,2-trifluoroethyl carbonate | None | — | 80.7 |
| Comparative Example 8 | Trifluoropropylene carbonate/ methyl difluoroacetate | None | — | 80.0 |
| Comparative Example 9 | FEC/ methyl 2,2,2-trifluoroethyl carbonate | None | — | 80.1 |
| Comparative Example 10 | FEC/ methyl difluoroacetate | None | — | 79.6 |
| Comparative Example 11 | FEC/ methyl 3,3,3-trifluoropropionate | None | — | 79.5 |

The invention claimed is:

1. An electrolyte solution comprising at least one selected from the group consisting of a compound represented by the following formula (1-1), a compound represented by the following formula (1-2), and a compound represented by the following formula (1-3), the formula (1-1) being:

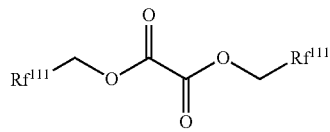

wherein $Rf^{111}$s are the same as or different from each other and are each a C2-C4 fluorinated alkenyl group, the formula (1-2) being:

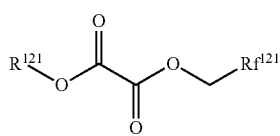

wherein $R^{121}$ is a C1-C4 alkyl group; and $Rf^{121}$ is a C2-C4 fluorinated alkenyl group, the formula (1-3) being:

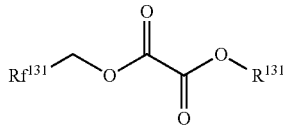

wherein $Rf^{131}$ is a C1-C3 fluorinated alkyl group; and $R^{131}$ is a C6-C12 aryl group free from a fluorine atom.

2. An electrochemical device comprising the electrolyte solution according to claim 1.

3. A lithium ion secondary battery comprising the electrolyte solution according to claim 1.

4. A module comprising the electrochemical device according to claim 2.

5. A compound represented by the following formula (1-1):

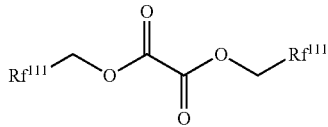

wherein $Rf^{111}$'s are the same as or different from each other and are each a C2-C4 fluorinated alkenyl group.

6. A compound represented by the following formula (1-2):

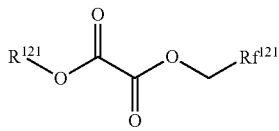

wherein $R^{121}$ is a C1-C4 alkyl group; and $Rf^{121}$ is a C2-C4 fluorinated alkenyl group.

7. A compound represented by the following formula (1-3):

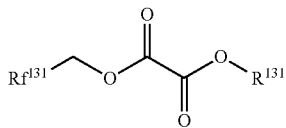

wherein $Rf^{131}$ is a C1-C3 fluorinated alkyl group; and $R^{131}$ is a C6-C12 aryl group free from a fluorine atom.

8. A module comprising the lithium ion secondary battery according to claim 3.

* * * * *